United States Patent
Cai et al.

(10) Patent No.: US 12,421,543 B2
(45) Date of Patent: Sep. 23, 2025

(54) OSCILLATING AMPLIFICATION REACTION FOR NUCLEIC ACIDS

(71) Applicant: Mesa Biotech LLC, Carlsbad, CA (US)

(72) Inventors: Hong Cai, Los Alamos, NM (US); Nathan J. Cobb, Durham, NC (US)

(73) Assignee: MESA BIOTECH LLC, Carlsbad, CA (US)

( * ) Notice: Subject to any disclaimer, the term of this patent is extended or adjusted under 35 U.S.C. 154(b) by 0 days.

(21) Appl. No.: 18/656,534

(22) Filed: May 6, 2024

(65) Prior Publication Data

US 2024/0287595 A1    Aug. 29, 2024

Related U.S. Application Data

(63) Continuation of application No. 17/696,027, filed on Mar. 16, 2022, which is a continuation of application No. 16/377,749, filed on Apr. 8, 2019, now Pat. No. 11,293,058, which is a continuation of application No. 15/247,728, filed on Aug. 25, 2016, now Pat. No. 10,316,358, which is a continuation of application No. 14/113,200, filed as application No. PCT/US2012/034589 on Apr. 20, 2012, now Pat. No. 9,428,781.

(60) Provisional application No. 61/477,437, filed on Apr. 20, 2011, provisional application No. 61/477,357, filed on Apr. 20, 2011.

(51) Int. Cl.
| | | |
|---|---|---|
| *C12Q 1/68* | (2018.01) | |
| *B01L 3/00* | (2006.01) | |
| *C12P 19/34* | (2006.01) | |
| *C12Q 1/6844* | (2018.01) | |
| *C12Q 1/686* | (2018.01) | |

(52) U.S. Cl.
CPC ........ *C12Q 1/686* (2013.01); *B01L 3/502723* (2013.01); *C12P 19/34* (2013.01); *C12Q 1/6844* (2013.01)

(58) Field of Classification Search
None
See application file for complete search history.

(56) References Cited

U.S. PATENT DOCUMENTS

| | | |
|---|---|---|
| 3,667,607 A | 6/1972 | Brandt |
| 4,235,601 A | 11/1980 | Deutsch et al. |
| 4,663,277 A | 5/1987 | Wang |
| 4,683,105 A | 7/1987 | Hager |
| 4,683,195 A | 7/1987 | Mullis et al. |
| 4,683,202 A | 7/1987 | Mullis |
| 4,800,159 A | 1/1989 | Mullis et al. |
| 4,960,691 A | 10/1990 | Gordon et al. |
| 5,225,163 A | 7/1993 | Andrews |
| 5,354,538 A | 10/1994 | Bunce et al. |
| 5,514,785 A | 5/1996 | Van Ness et al. |
| 5,516,664 A | 5/1996 | Hyman |
| 5,578,467 A | 11/1996 | Schuster et al. |
| 5,618,494 A | 4/1997 | Bunce et al. |
| 5,716,819 A | 2/1998 | Chatterjee |
| 5,736,188 A | 4/1998 | Alcock et al. |
| 5,741,647 A | 4/1998 | Tam |
| 5,922,617 A | 7/1999 | Wang et al. |
| 6,007,999 A | 12/1999 | Clark |
| 6,037,127 A | 3/2000 | Ebersole et al. |
| 6,083,502 A | 7/2000 | Pastan et al. |
| 6,146,589 A | 11/2000 | Chandler |
| 6,190,612 B1 | 2/2001 | Berger et al. |
| 6,214,587 B1 | 4/2001 | Dattagupta et al. |
| 6,261,779 B1 | 7/2001 | Barbera-Guillem et al. |
| 6,300,069 B1 | 10/2001 | Missel et al. |
| 6,335,205 B1 | 1/2002 | Bausback |
| 6,468,749 B1 | 10/2002 | Ulanovsky et al. |
| 6,471,916 B1 | 10/2002 | Noblett |
| 6,555,349 B1 | 4/2003 | O'Donnell |
| 6,743,399 B1 | 6/2004 | Weigl et al. |
| 7,094,536 B2 | 8/2006 | Kurn |
| 7,159,618 B2 | 1/2007 | Broyer et al. |
| 7,186,508 B2 | 3/2007 | Lee et al. |
| 7,195,872 B2 | 3/2007 | Agrawal et al. |
| 7,273,590 B2 | 9/2007 | Yao et al. |
| 8,173,078 B2 | 5/2012 | Yao et al. |
| 8,980,561 B1 | 3/2015 | Cai et al. |
| 9,207,236 B2 | 12/2015 | Cary |

(Continued)

FOREIGN PATENT DOCUMENTS

| | | |
|---|---|---|
| CN | 1254844 A | 5/2000 |
| CN | 1654214 A | 8/2005 |

(Continued)

OTHER PUBLICATIONS

Ralser et al. (Biochem Biophys Res Comm, 2006, vol. 347, p. 747-751) (Year: 2006).*
Al Soud et al. (J Clin Micro, 2000, vol. 38, No. 12, p. 4463-4470) (Year: 2000).*
Little et al. (Clin Chem, 1999, 45:6, 777-784) (Year: 1999).*
Giordano et al. (Anal Biochem, 2001, 291:124-132) (Year: 2001).*
Erill et al. (J of Micromech and Microeng, 2004, 14:1558-1568) (Year: 2004).*

(Continued)

*Primary Examiner* — Stephanie K Mummert

(57) ABSTRACT

One embodiment of the present invention provides for a method for amplifying a template of nucleic acid target sequence contained in a sample. The method includes contacting the sample with an amplification reaction mixture containing a primer complementary to the template of nucleic acid target sequence. A temperature of the reaction is oscillated between an upper temperature and a lower temperature wherein the change in temperature is no greater than about 20° C. during a plurality of temperature cycles. The template of nucleic acid target sequence is amplified.

24 Claims, 27 Drawing Sheets
Specification includes a Sequence Listing.

(56) References Cited

U.S. PATENT DOCUMENTS

| | | | |
|---|---|---|---|
| 9,354,199 B2 | 5/2016 | Selden et al. | |
| 9,428,781 B2 * | 8/2016 | Cai | B01L 3/502723 |
| 9,944,922 B2 | 4/2018 | Cary | |
| 10,316,358 B2 * | 6/2019 | Cai | B01L 3/502723 |
| 11,293,058 B2 * | 4/2022 | Cai | B01L 3/502723 |
| 2001/0019825 A1 | 9/2001 | Lee et al. | |
| 2002/0028475 A1 | 3/2002 | Ligler et al. | |
| 2002/0058252 A1 | 5/2002 | Ananiev | |
| 2002/0076825 A1 | 6/2002 | Cheng et al. | |
| 2002/0127574 A1 | 9/2002 | Mirkin et al. | |
| 2002/0172969 A1 | 11/2002 | Burns et al. | |
| 2002/0177135 A1 | 11/2002 | Doung et al. | |
| 2002/0179445 A1 | 12/2002 | Alajoki et al. | |
| 2002/0192839 A1 | 12/2002 | Mink et al. | |
| 2003/0003514 A1 | 1/2003 | Kovalenko | |
| 2003/0008308 A1 | 1/2003 | Enzelberger et al. | |
| 2003/0044862 A1 | 3/2003 | Giaccia et al. | |
| 2003/0054176 A1 | 3/2003 | Pantano et al. | |
| 2003/0064364 A1 | 4/2003 | Lockhart et al. | |
| 2003/0100128 A1 | 5/2003 | Kenjyou et al. | |
| 2003/0170686 A1 | 9/2003 | Hoet et al. | |
| 2003/0190608 A1 | 10/2003 | Blackburn | |
| 2004/0029177 A1 | 2/2004 | Nadaoka et al. | |
| 2004/0053256 A1 | 3/2004 | Lee et al. | |
| 2004/0058378 A1 | 3/2004 | Kong et al. | |
| 2004/0086897 A1 | 5/2004 | Mirkin et al. | |
| 2004/0110167 A1 | 6/2004 | Gerdes et al. | |
| 2004/0119167 A1 | 6/2004 | Suk | |
| 2004/0152122 A1 * | 8/2004 | Hwang | C12P 19/34 435/91.2 |
| 2004/0209309 A1 | 10/2004 | Muldoon et al. | |
| 2005/0014192 A1 | 1/2005 | Kurn | |
| 2005/0032729 A1 | 2/2005 | Shyamala | |
| 2005/0032730 A1 | 2/2005 | Von Der Mulbe et al. | |
| 2005/0042627 A1 | 2/2005 | Chakrabarti et al. | |
| 2005/0047972 A1 | 3/2005 | Lauks et al. | |
| 2005/0079492 A1 | 4/2005 | Burgess, Jr. et al. | |
| 2005/0112780 A1 | 5/2005 | Song | |
| 2005/0136443 A1 | 6/2005 | Shigemori | |
| 2005/0221281 A1 | 10/2005 | Ho | |
| 2005/0227275 A1 | 10/2005 | Jung et al. | |
| 2005/0243321 A1 | 11/2005 | Cohen et al. | |
| 2005/0250141 A1 | 11/2005 | Lambert et al. | |
| 2006/0024813 A1 | 2/2006 | Warthoe | |
| 2006/0041058 A1 | 2/2006 | Yin et al. | |
| 2006/0127886 A1 | 6/2006 | Kaylor et al. | |
| 2006/0154286 A1 | 7/2006 | Kong et al. | |
| 2006/0160078 A1 | 7/2006 | Cardy et al. | |
| 2006/0169078 A1 | 8/2006 | Hiraiwa | |
| 2006/0177873 A1 | 8/2006 | Dowd et al. | |
| 2006/0239859 A1 | 10/2006 | Ohman et al. | |
| 2006/0246601 A1 | 11/2006 | Song et al. | |
| 2006/0286570 A1 | 12/2006 | Rowlen et al. | |
| 2007/0015166 A1 | 1/2007 | Nilsen | |
| 2007/0020768 A1 | 1/2007 | Rundstrom et al. | |
| 2007/0039835 A1 | 2/2007 | Rossier et al. | |
| 2007/0231798 A1 | 10/2007 | Collins | |
| 2008/0124720 A1 | 5/2008 | Sowerby et al. | |
| 2008/0145835 A1 | 6/2008 | Alajem et al. | |
| 2008/0207892 A1 | 8/2008 | Iwaki et al. | |
| 2008/0280285 A1 | 11/2008 | Chen et al. | |
| 2009/0047673 A1 | 2/2009 | Cary | |
| 2009/0053106 A1 | 2/2009 | Wu et al. | |
| 2009/0086357 A1 | 4/2009 | Ehrlich | |
| 2009/0130719 A1 | 5/2009 | Handique | |
| 2009/0136719 A1 | 5/2009 | Kawamura et al. | |
| 2009/0181411 A1 | 7/2009 | Battrell et al. | |
| 2009/0186357 A1 | 7/2009 | Mauk et al. | |
| 2009/0246782 A1 | 10/2009 | Kelso et al. | |
| 2010/0203532 A1 | 8/2010 | Makrigiorgos | |
| 2010/0248273 A1 | 9/2010 | Campbell et al. | |
| 2010/0276005 A1 | 11/2010 | Allain et al. | |
| 2011/0039261 A1 | 2/2011 | Hillebrand et al. | |
| 2011/0117540 A1 | 5/2011 | Cary | |
| 2011/0160090 A1 | 6/2011 | Cary | |
| 2014/0045191 A1 | 2/2014 | DeJohn et al. | |
| 2014/0141484 A1 | 5/2014 | Campbell et al. | |
| 2015/0184255 A1 | 7/2015 | Cai et al. | |
| 2016/0083716 A1 | 3/2016 | Cary | |
| 2016/0222442 A1 | 8/2016 | Cary | |
| 2016/0310948 A1 | 10/2016 | Nowakowski et al. | |
| 2016/0362725 A1 | 12/2016 | Cai et al. | |
| 2017/0160271 A1 | 6/2017 | Cary | |
| 2017/0233794 A1 | 8/2017 | Cai et al. | |
| 2018/0304260 A1 | 10/2018 | Thomas et al. | |

FOREIGN PATENT DOCUMENTS

| | | |
|---|---|---|
| CN | 1954214 A | 4/2007 |
| CN | 101400993 A | 4/2009 |
| EP | 0805215 A2 | 11/1997 |
| EP | 1972938 A1 | 9/2008 |
| GB | 2261284 A | 5/1993 |
| JP | H05240872 A | 9/1993 |
| JP | 2001518614 A | 10/2001 |
| JP | 2005185972 A | 7/2005 |
| JP | 2005532827 A | 11/2005 |
| JP | 2006185972 A | 7/2006 |
| JP | 2006520190 A | 9/2006 |
| JP | 2007503958 A | 3/2007 |
| JP | 2007503968 A | 3/2007 |
| JP | 2008521432 A | 6/2008 |
| JP | 2009100761 A | 5/2009 |
| WO | WO-9423055 A1 | 10/1994 |
| WO | WO-9703207 A1 | 1/1997 |
| WO | WO-0029112 A1 | 5/2000 |
| WO | WO-2004007078 A1 | 1/2004 |
| WO | WO-2004090555 A1 | 10/2004 |
| WO | WO-2004092342 A2 | 10/2004 |
| WO | WO-2005098439 A2 | 10/2005 |
| WO | WO-2006059911 A1 | 6/2006 |
| WO | WO-2006098804 A2 | 9/2006 |
| WO | WO-2006122311 A2 | 11/2006 |
| WO | WO-2007030505 A1 | 3/2007 |
| WO | WO-2007083388 A1 | 7/2007 |
| WO | WO-2008105814 A2 | 9/2008 |
| WO | WO-2009103843 A2 | 8/2009 |
| WO | WO-2009137055 A1 | 11/2009 |
| WO | WO-2009137059 A1 | 11/2009 |
| WO | WO-2010037012 A2 | 4/2010 |
| WO | WO-2010105074 A1 | 9/2010 |
| WO | WO-2011087813 A2 | 7/2011 |
| WO | WO-2012083189 A2 | 6/2012 |
| WO | WO-2012145725 A2 | 10/2012 |
| WO | WO-2012145730 A2 | 10/2012 |

OTHER PUBLICATIONS

Shaw et al. (Lab on Chip, 2010, 10: 1725-1728) (Year: 2010).*
Akane A., et al., "Identification Of The Heme Compound Copurified With Deoxyribonucleic Acid (Dna) From Bloodstains, A Major Inhibitor Of Polymerase Chain Reaction (Pcr) Amplification," Journal of Forensic Sciences, Mar. 1994, vol. 39, No. 2, pp. 362-372.
Albretsen C., et al., "Optimal Conditions For Hybridization With Oligonucleotides: A Study With Myc-Oneogene DNA Probes," Analytical Biochemistry, Apr. 1988, vol. 170, No. 1, pp. 193-202.
Al-Soud W.A., et al., "Effects of Amplification Facilitators on Diagnostic PCR in the Presence of Blood, Feces, and Meat," Journal of Clinical Microbiology, Lund Institute of Technology, Lund University, Lund, Sweden, Dec. 2000, vol. 38, No. 12, pp. 4463-4470.
An L., et al., "Characterization Of A Thermostable Uvrd Helicase And Its Participation In Helicase-Dependent Amplification," The Journal of Biological Chemistry, Aug. 12, 2005, vol. 280, No. 32, pp. 28952-28958.
Andreotti P.E., et al., "Immunoassay Of Infectious Agents," BioTechniques, Oct. 2003, vol. 35, No. 4, pp. 850-859.
Ausbel, et al., "cDNA Amplification Using One-Sided (Anchored) PCR," Current Protocols in Molecular Biology, Sep. 17, 1992, pp. 15.6.1-15.6.4.
Aveyard J., et al., "One Step Visual Detection Of Pcr Products With Gold Nanoparticles And A Nucleic Acid Ateral Ftow (Nalf) Device," ChemComm, 2007, pp. 4251-4253.

(56) References Cited

OTHER PUBLICATIONS

Baeumner A.J., "Biosensors for Environmental Pollutants and Food Contaminants," Analytical and Bioanalytical Chemistry, 2003, vol. 377, pp. 434-445.

Baeumner A.J., et al., "A Rapid Biosensor For Viable B. Anthracis Spores," Analytical and Bioanalytical Chemistry, 2004, vol. 380, pp. 15-23.

Baeumner A.J., et al., "A Universal Nucleic Acid Sequence Biosensor With Nanomolar Detection Limits," Analytical Chemistry, Feb. 15, 2004, vol. 76, pp. 888-894.

Baeumner A.J., et al., "Biosensor for Dengue Virus Detection: Sensitive, Rapid, and Serotype Specific, Analytical Chemistry," American Chemical Society, Mar. 15, 2002, vol. 74, No. 6, pp. 1442-1448.

Barany F., "The Ligase Chain Reaction in a PCR World," PCR Methods and Applications, 1991, vol. 1, pp. 5-16.

Barnes W.M., "PCR Amplification of up to 35-kb DNA with High Fidelity and High Yield from Bacteriophage Templates," Proceedings of the National Academy of Sciences (PNAS), Jun. 15, 1994, vol. 91, No. 6, pp. 2216-2220.

Baskaran N., et al., "Uniform Amplification of a Mixture of Deoxyribonucleic Acids with Varying GC Content," Genome Research, 1996, vol. 6, No. 7, pp. 633-638.

Berthelet M., et al., "Rapid, direct Extraction of DNA from soils for PCR Analysis using Polyvinylpyrrolidone Spin Columns," FEMS Microbiology Letter, 1996, vol. 138 (1), pp. 17-22, Federation of European Microbiological Societies.

Biagini R.E., et al., "Rapid, Sensitive, and Specific Lateral-Flow Immunochromatographic Device to Measure Anti-Anthrax Protective Antigen Immunoglobulin G in Serum and Whole Blood," Clinical and Vaccine Immunology, May 5, 2006, vol. 13, No. 5, pp. 541-546.

Blake R.D., et al., "Thermodynamic Effects of Formamide on DNA Stability," Nucleic Acids Research, Oxford University Press, 1996, vol. 24, No. 11, pp. 2095-2103.

Boom R., et al., "Rapid and Simple Method for Purification of Nucleic Acids," Journal of Clinical Microbiology, Mar. 1990, vol. 28, No. 3, pp. 495-503.

Boom R., et al., "Rapid Purification of Hepatitis B Virus DNA From Serum," Journal of Clinical Microbiology, Sep. 1991, vol. 29. No. 9, pp. 1804-1811.

Braasch D.A., et al., "Locked Nucleic Acid (LNA): Fine-Tuning The Recognition of DNA And RNA," Chemistry & Biology, Elsevier Science Ltd., 2001, vol. 8, pp. 731-735.

Braun D., et al., "Exponential DNA Replication by Laminar Convection," Physical Review Letters, Oct. 10, 2003, vol. 91, No. 15, pp. 158103-1-158103-4.

Bright R.A., et al., "Incidence Of Adamantane Resistance Among Influenza A (H3N2) Viruses Isolated Worldwide From 1994 To 2005: A Cause For Concern," Lancet, Sep. 22, 2005, vol. 366, pp. 1175-1181.

Brlansky R. H., et al., "Colonization of the Sharpshooter Vectors, Oncometopia nigricans and Homalodisca Coagulata, by Xylem-Limited Bacteria," Phytopathology, 1983, pp. 530-535.

Brlansky R.H., et al., "Transmission Of The Citrus Variegated Chlorosis Bacterium Xylella Fastidiosa With The Sharpshooter Oncometopia Nigricans," Plant Disease, Nov. 2002, vol. 86, No. 11, pp. 1237-1239.

Buck G.A., et al., "Design Strategies and Performance of Custom DNA Sequencing Primers," BioTechniques, Sep. 1999, vol. 27, No. 3, pp. 528-536.

Buhro W.E., et al., "Semiconductor Nanocrystals: Shapematters," Nature Materials, Mar. 2003, vol. 2, No. 3, pp. 138-139.

Burns M.A., et al., "An Integrated Nanoliter DNA Analysis Device," Science, Oct. 16, 1998, vol. 282, pp. 484-487.

Cai H., et al., "Oscillating Amplification ReAction for Nucleic Acids," U.S. Appl. No. 61/477,437, filed Apr. 20, 2011,54 Pages.

Capaldi S., et al., "Signal Amplification Through Nucleotide Extension And Excision on a Dendritic DNA Platform," Nucleic Acids Research, Oxford University Press, 2000, vol. 28, No. 7, 8 Pages.

Carney J., et al., "Present and Future Applications of Gold in Rapid Assays," IVD Technology, Mar. 1, 2006, pp. 1-8.

Carter D.J., et al., "Lateral Flow Microarrays: A Novel Platform For Rapid Nucleic Acid Detection Based on Miniaturized Lateral Flow Chromatography," Nucleic Acids Research, May 3, 2007, vol. 35, No. 10, pp. 1-11.

Caruthers J.M., et al., "Helicase Structure And Mechanism," Current Opinion In Structural Biology, 2002, vol. 12, pp. 123-133.

Cary, "An Integrated Low Cost Nucleic Acid Analysis Platform for the Rapid Detection of Plan Pathogens," Jan. 6, 2011.

Chang C.J., et al., "Culture and Serological Detection of the Xylem-Limited Bacterium Causing Citrus Variegated Chlorosis and Its Identification as a Strain of Xylella Fastidiosa," Current Microbiology, 1993, vol. 27, pp. 137-142.

Chanteau S., et al., "Early Diagnosis of Bubonic Plague Using F1 Antigen Capture ELISA Assay And Rapid Immunogold Dipstick," International Journal of Medical Microbiology, Urban & Fischer Verlag, 2000, vol. 290, No. 3, pp. 279-283.

Cheek B.J. et al., "Chemiluminescence Detection for Hybridization Assays on the Flow-Thru Chip, a Three-Dimensional Microchannel Biochip," Analytical Chemistry, American Chemical Society, Dec. 15, 2001, vol. 73, No. 24, pp. 5777-5783.

Cheng J., et al., "Chip PCR. II Investigation of Different PCR Amplification Systems in Microfabricated Silicon-Glass Chips," Nucleic Acids Research, 1996, vol. 24 (2), pp. 380-385.

Chin C.D., et al., "Lab-on-a-Chip Devices for Global Health: Past Studies and Future opportunities," Lab Chip, The Royal Society of Chemistry, 2007, vol. 7, pp. 41-57.

Ciapina L.P., et al., "A Nested-PCR Assay for Detection of Xylella Fastidiosa In Citrus Plants and Sharpshooter Leafhoppers," Journal of Applied Microbiology, Society for Applied Microbiology, 2004, vol. 96, pp. 546-551.

Cirino N.M., et al., "Multiplex Diagnostic Platforms For Detection of Biothreat Agents," Expert Review of Molecular Diagnostics, Future Drugs, Ltd, 2004, vol. 4 (6), pp. 841-857.

Collins R., et al., "Purification and Characterization of Thermus Thermophilus UvrD," Extremophiles, 2003, vol. 7, pp. 35-41.

Compton J., "Nucleic Acid Sequence-Based Amplification," Nature, Mar. 7, 1991, vol. 350, pp. 91-92.

Cook A.F., et al., "Synthesis and Hybridization of a Series of Biotinylated Oligonucleotides," Nucleic Acids Research, IRL Press Limited, Oxford, England, 1988, vol. 16 (9), pp. 4077-4095.

Corstjens P., et al., "Use of Up-Converting Phosphor Reporters in Lateral-Flow Assays to Detect Specific Nucleic Acid Sequences: A Rapid, Sensitive DNA Test to Identify Human Papillomavirus Type 16 Infection," Clinical Chemistry, 2001, vol. 47 (10), pp. 1885-1893.

Cubero J., et al., "Genetic Relationship among Worldwide Strains of Xanthomonas Causing Canker in Citrus Species and Design of New Primers for Their Identification by PCR," Applied and Environmental Microbiology, Mar. 2002, vol. 68, No. 3, pp. 1257-1264.

Cubero J., et al., "Quantitative PCR Method for Diagnosis of Citrus Bacterial Canker," Applied and Environmental Microbiology, American Society for Microbiology, Jun. 2001, vol. 67, No. 6, pp. 2849-2852.

David H., "Point-of-Care Diagnostices: Will the Hurdles Be Overcome This Time?," Expert Review of Medical Devices, 2006, vol. 3 (4), pp. 421-426.

Davis M.J., et al., "Pierce's Disease of Grapevines: Isolation of the Causal Bacterium," Science, Jan. 6, 1978, vol. 199, pp. 75-77.

Dawson E.D., et al., "Identification of A/H5N1 Influenza Viruses Using a Single Gene Diagnostic Microarray," Analytical Chemistry, American Chemical Society, Jan. 1, 2007, vol. 79, No. 1, pp. 378-384.

Day P .J.R., et al., "Immobilization of Polynucleotides on Magnetic Particles: Factors Influencing Hybridization Efficiency," Biochemistry Journal, 1991, vol. 278, pp. 735-740.

De Jong M.D., et al., "Oseltamivir Resistance during Treatment of Influenza A (H5N1) Infection," The New England Journal of Medicine, Massachusetts Medical Society, Dec. 22, 2005, vol. 353, No. 25, pp. 2667-2672.

(56) References Cited

OTHER PUBLICATIONS

Deiman B., et al., "Characteristics and Applications of Nucleic Acid Sequence-Based Amplification (NASBA)," Molecular Biotechnology, Humana Press Incorporated, 2002, vol. 20, pp. 163-179.
Dineva M.A., et al., "Simultaneous Visual Detection of Multiple Viral Amplicons by Dipstick Assay," Journal of Clinical Microbiology, American Society for Microbiology, Aug. 2005, vol. 43 (8), pp. 4015-4021.
Dobkin C., et al., "RNA Replication: Required Itermediates and the Dissociation of Template, Product, and QB Replicase," Biochemistry, American Chemical Society, 1979, vol. 18, pp. 2038-2044.
Dong F., et al., "A Coupled Complex of T4 DNA Replication Helicase (gp41) and Polymerase (gp43) can Perform Rapid and Processive DNA Strand-Displacement Synthesis," Proceedings of the National Academy of Sciences of the United States of America, Dec. 1996, vol. 93, pp. 14456-14461.
Duck P., et al., "Probe Amplifier System Based on Chimeric Cycling Oligonucleotides," Biotechniques, Aug. 1990, vol. 9, No. 2, pp. 142-148.
Easterday, W. R., et al., "Specific Detection of Bacillus Anthracis using a Taqman Mismatch Amplification Mutation Assay," BioTechniques, 2005, vol. 38 (5), pp. 731-735.
Easterday, W. R., et al., "Use of Single Nucleotide Polymorphisms in the plcR Gene for Specific Identification of Bacillus Anthracis," Journal of Clinical Microbiology, American Society for Microbiology, Apr. 2005, vol. 43 (4), pp. 1995-1997.
Edwards K.A., et al., "Optimization of DNA-Tagged Dye-Encapsulating Liposomes For Lateral-Flow Assays Based on Sandwich Hybridization," Analytical and Bioanalytical Chemistry, 2006, vol. 386, pp. 1335-1343.
Eggerding F.A., "A One-Step Coupled Amplification and Oligonucleotide Ligation Procedure for Multiplex Genetic Typing," PCR Methods &Applications, Jun. 4, 1995, vol. 4, No. 6, pp. 337-345, XP000522968, ISSN: 1054-9803.
Elliott K., et al., "Use of Laser Microdissection Greatly Improves the Recovery of DNA from Sperm on Microscope Slides," Forensic Science International, Elsevier Ireland Ltd, 2003, vol. 137 (1), pp. 28-36.
Findlay J.B., et al., "Automated Closed-Vessel System for in Vitro Diagnostics Based on Polymerase Chain ReAction," Clinical Chemistry, 1993, vol. 39 (9), pp. 1927-1933.
Fisher A.M., et al., "Development of a Quantum Dot-Lateral Flow Assay," BEACON e-news at Jet Propulsion Laboratory, 2003, 2 pages.
Fong W.K., et al., "Rapid Solid-Phase Immunoassay for Detection of Methicillin-Resistant *Staphylococcus aureus* Using Cycling Probe Technology," Journal of Clinical Microbiology, American Society for Microbiology, Jul. 2000, vol. 38 (7), pp. 2525-2529.
Frackman S., et al., "Betaine and DMSO: Enhancing Agents for PCR," Promega Notes No. 65, 1998, 4 pages.
Fu E., et aL, "Controlled Reagent Transport in Disposable 2D Paper Networks," Lab Chip, 2010, vol. 10, pp. 918-920.
Fukuta S., et al., "Development of Immunocapture Reverse Transcription Loop-Mediated Isothermal Amplification For The Detection of Tomato Spotted Wilt Virus From Chrysanthemum," Journal of Virological Methods, Elsevier B.V, 2004, vol. 121 (1), pp. 49-55.
Gani R., et al., "Potential Impact of Antiviral Drug Use during Influenza Pandemic," Emerging Infectious Diseases, Sep. 2005, vol. 11 (9), pp. 1355-1362.
Gill P., "Application of Low Copy Number DNA Profiling, " Croatian Medical Journal, 2001, vol. 42 (3), pp. 229-232.
Gill P., et al., "An Investigation of the Rigor of Interpretation Rules for STRs Derived From Less Than 100 pg of DNA," Forensic Science International, Elsevier Science Ireland Ltd, 2000, vol. 112, pp. 17-40.
Glynou K., et al., "Oligonucleotide-Functionalized Gold Nanopartices as Probes in a Dry-Reagent Strip Biosensor for DNA Analysis by Hybridization," Analytical Chemistry, American Chemical Society, Aug. 15, 2003, vol. 75 (16), pp. 4155-4160.

Goda T., et al., "Label-Free Potentiometry for Detecting DNA Hybridization Using Peptide Nucleic Acid and DNA Probes," Sensors, 2013, vol. 13, pp. 2267-2278.
Goheen A. C., et al., "Association of a Rickettsialike Organism with Pierce's Disease of Grapevines and Alfalfal Swarf and Heat Therapy of the Disease in Grapevines," Phytopathology, Mar. 1973, vol. 63, pp. 341-345.
Goldmeyer J., et al., "Development of a Novel One-Tube Isothermal Reverse Transcription Thermophilic Helicase-Dependent Amplification Platform for Rapid RNA Detection," Journal of Molecular Diagnostics, Nov. 2007, vol. 9 (5), pp. 639-644.
Grainge I., et al., "Biochemical Analysis of Components of the Pre-Replication Complex Of Archaeoglobus Fulgidus," Nucleic Acids Research, Oxford University Press, 2003, vol. 31 (16), pp. 4888-4898.
Groody E. P., "Detection of Foodborne Pathogens Using DNA Probes and a Dipstick Format," Molecular Biotechnology, Humana Press, Inc, 1996, vol. 6, pp. 323-327.
Guatelli, J.C., et al., "Isothermal, In Vitro Amplification of Nucleic Acids by a Multienzyme ReAction Modeled after Retroviral Replication," Proceedings of the National Academy of Sciences of the United States of America, Mar. 1990, vol. 87, pp. 1874-1878.
Guo Z., et al., "Direct Fluorescence Analysis Of Genetic Polymorphisms By Hybridization With Oligonucleotide Arrays On Glass Supports," Nucleic Acids Research, Dec. 11, 1994, vol. 22, No. 24, pp. 5456-5465.
Harmon F.G., et al., "Biochemical characterization of the DNA helicase activity of the *Escherichia coli* RecQ helicase," Journal of Biological Chemistry, 2001, vol. 276 (1), pp. 232-243.
Hartley H.A., et al., "Biosensor for the Specific Detection of a Single Viable B. Anthracis Spore," Analytical and Bioanalytical Chemistry, 2003, vol. 376, pp. 319-327.
Hartun, J. S., et al., "Detection of Xanthomonas Campestris pv. Citri by the Polymerase Chain Reaction Method," Applied and Environmental Microbiology, American Society for Microbiology, Apr. 1993, vol. 59 (4), pp. 1143-1148.
Hartung J.S., et aL, "Rapid and Sensitive Colorimetric Detection of Xanthomonas Axonopodis pv. citri by Immunocapture and a Nested-Polymerase Chain Reaction Assay," Phytopathology, American Phytopathological Society , 1996, vol. 86 (1), pp. 95-101.
Heller M.J., "DNA Microarray Technology: Devices, Systems, and Applications," Annual Review of Biomedical Engineering, 2002, vol. 4, pp. 129-153.
Hendson M., et aL, "Genetic Diversity of Pierce's Disease Strains and Other Pathotypes ofXylella fastidiosa," Applied and Environmental Microbiology, American Society for Microbiology, Feb. 2001, vol. 67 (2), pp. 895-903.
Henegariu O., et al., "Multiplex PCR: Critical Parameters and Step-By-Step Protocol," BioTechniques, Sep. 1997, vol. 23, No. 3, pp. 504-511.
Henke W., et al., "Betaine Improves the PCR Amplification of GC-rich DNA Sequences," Nucleic Acids Research, 1997, vol. 25 (19), pp. 3957-3958.
Hill B.L., et al., "Acquisition and Retention ofXylella fastidiosa by an Efficient Vector, Graphocephala Atropunctata," Phytopathology, American Phytopathological Society, 1995, vol. 85 (2), pp. 209-212.
Hill B.L., et al., "Populations ofXylella Fastidiosa in Plants Required for Transmission by an Efficient Vector," Phytopathology, American Phytopathological Society , 1997, vol. 87 (12), pp. 1197-1201.
Hill K.K., et al., "Fluorescent Amplified Fragment Length Polymorphism Analysis of Bacillus Anthracis, Bacillus cereus, and Bacillus thuringiensis Isolates," Applied and Environmental Microbiology, American Society for Microbiology, Feb. 2004, vol. 70 (2), pp. 1068-1080.
Hopkins D.L., "Xylella fastidiosa: Xylem-Limited Bacterial Pathogen of Plants," Annual Review of Phytopathology, Annual Reviews Inc, 1989, vol. 27, pp. 271-290.
Huang C., et aL, "A Capillary-Driven Microfluidic Device for Rapid DNA Detection with Extremely Low Sample Consumption," 17th International Conference on Miniaturized Systems for Chemistry and Life Science, Freiburg, Germany, Oct. 27-31, 2013, Oct. 2013, pp. 191-193.

(56) References Cited

OTHER PUBLICATIONS

Huber M., et aL, "Accessing Single Nucleotide Polymorphisms in Genomic DNA by Direct Multiplex Polymerase Chain ReAction Amplification on Oligonucleotide Microarrays," Analytical Biochemistry, Elsevier Science (USA), 2002, vol. 303, pp. 25-33.

Hutton J.R., et al., "Activity of Endonuclease S1 in Denaturing Solvents: Dimethylsulfoxide, Dimethylformamide, Formamide and Formaldehyde," Biochemical and Biophysical Research Communications, Academic Press, Inc, 1975, vol. 66 (3), pp. 942-948.

Iakobashvili R., et aL, "Low Temperature Cycled PCR Protocol for Klenow Fragment of DNA Polymerase I in the Presence of Proline," Nucleic Acids Research, 1999, vol. 27 (6), pp. 1566-1568.

Ilyushina N.A., et aL, "Detection of Amantadine-Resistant Variants Among Avian Influenza Viruses Isolated In North America and Asia," Virology, Elsevier, Inc, 2005, vol. 341, pp. 102-106.

Jacobi V., et al., "Development of A Multiplex Immunocapture RT-PCR Assay For Detection And Differentiation of Tomato And Tobacco Mosaic Tobamoviruses," Journal of Virological Methods, Elsevier Science B.V., 1998, vol. 74, pp. 167-178.

Jacobsen N., et al., "Direct Isolation of Poly(A)+ RNA From 4 M Guanidine Thiocyanate-lysed Cell Extracts Using Locked Nucleic Acid-Oligo(T) Capture," Nucleic Acid Research, Oxford University Press, 2004, vol. 32, No. 7, pp. 1031-1042.

Jensen M.A., et al., "DMSO and Betaine Greatly Improve Amplification of GC-Rich Constructs in De Novo Synthesis," PLoS One, Jun. 2010, vol. 5 (6), 5 pages.

"Jikken Igaku Bessatsu Mokuteki De Eraberu PCR Jikken Protocol," Jan. 1, 2011, pp. 50, Fig. 1B, lines 1-12 (English translation of relevant passages attached).

Jobling M.A., et al., "Encoded Evidence: DNA in Forensic Analysis," Nature Reviews: Genetics, Oct. 2004, vol. 5, pp. 739-751.

Kandimalla E.R., et al., "Design, Biochemical, Biophysical And Biological Properties Of Cooperative Antisense Oligonucleotides," Nucleic Acids Research, Sep. 11, 1995, vol. 23, No. 17, pp. 3578-3584.

Kane M.D., et al., "Assessment Of The Sensitivity And Specificity Of Oligonucleotide (50mer) Microarrays," Nucleic Acids Research, Nov. 15, 2000, vol. 28, No. 22, pp. 4552-4557.

Kaplan D.L., et al., "DnaB from Thermus Aquaticus Unwinds Forked Duplex DNA with an Asymmetric Tail Length Dependence," The Journal of Biological Chemistry, Mar. 12, 1999, vol. 274, No. 11, pp. 6889-6897.

Kempitiya A., et al., "Localized Microwave Heating in Microwells for Parallel DNA Amplification Applications," Applied Physics Letters, 2009, vol. 94, pp. 064106-1-064106-3.

Keohavong P., et al., "Fidelity Of DNA Polymerases In DNA Amplification," Proceedings of the National Academy of Sciences (PNAS), Dec. 1989, vol. 86, pp. 9253-9257.

Kieleczawa J., et al., "DNA Sequencing By Primer Walking With Strings Of Contiguous Hexamers," Science, Dec. 11, 1992, vol. 258, No. 5089, pp. 1787-1791.

Kievits T., et al., "NASBAtm Isothermal Enzymatic In Vitro Nucleic Acid Amplification Optimized for the Diagnosis of HIV-1 Infection," Journal of Virological Methods, Dec. 1991, vol. 35 (3), pp. 273-286.

Kilbourne E.D., et al., "The Total Influenza Vaccine Failure of 1947 Revisited: Major intrasubtypic Antigenic Change Can Explain Failure of Vaccine In a Post-World War Ii Epidemic," Proceedings of the National Academy of Sciences of the United States of America, Aug. 6, 2002, vol. 99 (16), pp. 10748-10752.

Kim H.S., et al., "Recombinant fragment Assay for Gene Targeting Based on the Polymerase Chain Reaction," Nucleic Acids Research, IRL Press Limited, Oxford, England, 1988, vol. 16 (18), pp. 8887-8903.

Kimura N., et al., "One-Step Immobilization of r Poly(dT)-Modified DNA Onto Non- Modified Plastic Substrates By UV Irradiation For Microarrays," Biochemical and Biophysical Research Communications, 2006, vol. 347, pp. 477-484.

Koch W.H., "Technology Platforms for Pahrmacogenomic Diagnostic Assays," Nature Reviews Drug Discovery, Sep. 2004, vol. 3, pp. 749-761.

"Kodak DCS Quick Start Guide," 2005, 1 Page.

Kohn J., "An Immunochromatographic Technique," Immunology, 1968, vol. 15, pp. 863-865.

Koonjul P.K., et al., "Inclusion of Polyvinylpyrrolidone in the Polymerase Chain Reaction Reverses the Inhibitory Effects of Polyphenolic Contamination of RNA," Nucleic Acids Research, 1999, vol. 27, No. 3, pp. 915-916.

Kornberg., et al., "DNA Replication," 2nd Edition, WH Freeman and Company, New York, 1992, 12 Pages.

Kozwich D., et al., "Development of a Novel, Rapid Integrated Cryptosporidium parvum Detection Assay," Applied and Environmental Microbiology, American Society for Microbiology, Jul. 2000, vol. 66, No. 7, pp. 2711-2717.

Kwoh D.Y., et al., "Transcription-Based Amplification System And Detection Of Amplified Human Immunodeficiency Virus Type 1 With A Bead-based Sandwich Hybridization Format," Proceedings of the National Academy of Sciences (PNAS), Feb. 15, 1989, vol. 86, No. 4, pp. 1173-1177.

Landegren U., et al., "A Ligase-Mediated Gene Detection Technique," Science, Aug. 26, 1988, vol. 241, pp. 1077-1080.

Lane M.J., et al., "The Thermodynamic Advantage of DNA Oligonucleotide 'Stacking Hybridization' Reactions: Energetics of a DNA Nick," Nucleic Acids Research, 1997, vol. 25, No. 3, pp. 611-616.

Leone G., et al., "Direct Detection of Potato Leafroll Virus In Potato Tubers By Immunocapture and the Isothermal Luclic Acid Amplification Method NASBA," Journal of Virological Methods, 1997, vol. 66, pp. 19-27.

Liao C-S., et al., "Miniature RT-PCT System For Diagnosis of RNA-Based Viruses," Nucleic Acids Research, Oct. 12, 2005, vol. 33, No. 18, pp. 1-7.

Lim D.V., et al., "Current And Developing Technologies For Monitoring Agents Of Bioterrorism And Biowarfare," Clinical Microbiology Reviews, Oct. 1, 2005, vol. 18, No. 4, pp. 583-607.

Liu R.H., et al., "Self-contained, Fully Integrated Biochip For Sample Preparation, Polymerase Chain Reaction Amplification, And Dna Microarray Detection," Analytical Chemistry, vol. 76, No. 7, pp. 1824-1831.

Lockley A.K., et al., "Colorimetric Detection of Immobilised PCR Products Generated on A Solid Support," Nucleic Acids Research, Oxford University Press, 1997, vol. 25, No. 6, pp. 1313-1314.

Loens K., et al., "Evaluation of NucliSens EasyMAG for Automated Nucleic Acid Extraction from Various Clinical Specimens," Journal of Clinical Microbiology, American Society for Microbiology, Feb. 2007, vol. 45, No. 2, pp. 421-425.

Lonnberg M., et al., "Chromatographic Performance of a Thin Microporous Bed of Nitrocellulose," Journal of Chromatography B, Elsevier Science BV, 2001, vol. 763, pp. 107-120.

Lowe M., et al., "Multiplexed, Particle-Based Detection of DNa Using Flow Cytometry with 3DNA Dendrimers for Signal Amplification," Cytometry Part A, Wiley Intersciences, 2004, vol. 60, No. 2, pp. 135-144.

Mackay I.M., "Real-time PCR in the Microbiology Laboratory," European Society of Clinical Microbiology and Infectious Diseases, 2004, vol. 10, pp. 190-212.

Malek L., et al., "Nucleic Acid Sequence-Based Amplification (NASBA), Protocols for Nucleic Acid Analysis by Nonradioactive Probes," Edited by, Peter G. Isaac, Humana Press, Totowa, New Jersey, 1994, pp. 253-260.

Masny A., et al., "Ligation Mediated PCR Performed at Low Denaturation Temperatures—PCT Melting Profiles," Nucleic Acids Research, 2003, vol. 31, No. 18, e114, pp. 1-6.

Michalet X., et al., "Properties of Fluorescent Semiconductor Nanocrystals and Their Application to Biological Labeling," Single Molecules, WILEY-VCH Verlag Berlin GmbH, 2001, vol. 2, No. 4, pp. 261-276.

"Microarray technology: An array of opportunities, "Nature, Apr. 25, 2002, vol. 416, 4 pages.

(56) References Cited

OTHER PUBLICATIONS

Miyoshi D., et al., "Molecular Crowding Regulates the Structural Switch of the DNA G—Quadruplex," Biochemistry, American Chemical Society, Nov. 20, 2002, vol. 41, pp. 15017-15024.

Monteiro L., et al., "Complex Polysaccharides as PCR Inhibitors in Feces: Helicdobacter Pylori Model," Journal of Clinical Microbiology, American Society for Microbiology, Apr. 1997, vol. 35, No. 4, pp. 995-998.

Mouritzen P., et al., "Single Nucleotide Polymorphism Genotyping Using Locked Nucleic Acid (LNA TM)," Jan. 2003, vol. 3 (1), pp. 27-38.

Mumford R.A., et al., "Rapid Single-Tube Immunocapture RT-PCR For The Detection of Two Yam Potyviruses," Journal of Virological Methods, 1997, vol. 69, pp. 73-79.

Musso M., et al., "Betaine, Dimethyl Sulfoxide, and 7-Deaza-dGTP, a Powerful Mixture for Amplification of GC-Rich DNA Sequences," Journal of Molecular Diagnostics, Nov. 5, 2006, vol. 8 (5), pp. 544-550.

"NanoComposix," [Retrieved from the Internet on Jul. 27, 2017], 2014, 6 pages, Retrieved from Internet: URL: http://www.nanocomposix.com/pages/gold-colloid.

Ness J.V., et al., "Isothermal Reactions for the Amplification of Oligonucleotides," Proceedings of the National Academy of Sciences of the United States of America, Apr. 15, 2003, vol. 100, No. 8, pp. 4504-4509.

Nicholson K.G., et al., "Influenza," The Lancet, Nov. 22, 2003, vol. 362, pp. 1733-1745.

O'Meara D., et al., "Capture of Single-Stranded DNA Assisted by Oligonucleotide Modules," Analytical Biochemistry, 1998, vol. 255, pp. 195-203.

O'Meara D., et al., "Cooperative Oligonucleotides Mediating Direct Capture of Hepatitis C Virus RNA from Serum," Journal of Clinical Microbiology, Sep. 1998, vol. 36 (9), pp. 2454-2459.

Palese P., et al., "Influenza Vaccines: Present And Future," The Journal of Clinical Investigation, Jul. 2002, vol. 110, No. 1, pp. 9-13.

Pannucci J., et al., "Virulence Signatures: Microarray-Based Approaches to Discovery And Analysis," Biosensors and Biolelectronics, Elsevier, 2004, vol. 20, pp. 706-718.

Pastinen T., et al., "A System For Specific, High-throughput Genotyping By Allelespecific Primer Extension On Microarrays," Genome Research, 2000, vol. 10, pp. 1031-1042.

"PCR Amplification," Protocols and Applications Guide, [Retrieved on Feb. 17, 2016], 2016, 48 pages, Retrieved from Internet: URL: https://www.promega.ca/resources/product-guides-and-electors/protocols-and-applications-guide/pcr-amplification.

Pemov A., et al., "DNA Analysis With Multiplex Microarray-enhanced PCR," Nucleic Acids Research, 2005, vol. 33, No. 2, pp. 1-9.

Petrik J., "Diagnostic Applications of Microarrays," Transfusion Medicine, Blackwell Publishing, Ltd., 2006, vol. 16, pp. 233-247.

Peytavi R., et al., "Microfluidic Device for Rapid (15 min) Automated Microarray Hybridization," Clinical Chemistry, 2005, vol. 51, No. 19, pp. 1836-1844.

Piepenburg O., et al., "DNA Detection Using Recombination Proteins," PLoS Biology, Jul. 1, 2006, vol. 4, No. 7, pp. 1115-1121, XP002501560.

Pooler M.R., et al., "Detection of Xylella Fastidiosa in Potential Insect Vectors By Immunomagnetic Separation And Nested Polymerase Chain Reaction," The Society for Applied Bacteriology, Letters in Applied Microbiology, 1997, vol. 25, pp. 123-126.

Pooler M.R., et al., "Specific PCR Detection and Identification of Xylella fastidiosa Strains Causing Citrus Variegated Chlorosis," Current Microbiology, Springer-Verlag New York, Inc., 1995, vol. 31, pp. 377-381.

Pristoupil T.I., "Microchromatography and Microelectrophoresis on Nitrocellulose Membranes," Chromatographic Reviews, 1970, vol. 12, pp. 109-125.

Purcell A.H., et al., "Fate Of Pierce's Disease Strains Of Xylella Fastidiosa In Common Riparian Plants In Californiat," Plant Disease, Sep. 1999, vol. 83, No. 9, pp. 825-830.

Purcell A.H., et al., "Pierce's Disease Bacterium: Mechanism of Transmission by Leafhopper Vectors," Science, Nov. 16, 1979, vol. 206, pp. 839-841.

Rajendrakumar C.S.V., et al., "DNA Helix Destabilization by Proline and Betaine: Possible Role in the Salinity Tolerance Process," FEBS Letters, 1997, vol. 410, pp. 201-205.

Ralser M., et al., "An Efficient and Economic Enhancer Mix for PCR," Biochemical and Biophysical Research Communications, 2006, vol. 347, pp. 747-751.

Rao R.S., et al., "Developing Rapid, Point-of-Care, Multiplex Detection for Use In Lateral Flow Devices," Smart Medical and Biomedical Sensor Technology III, Proceeding of SPIE, 2005, vol. 6007, 7 pages.

Rapley R., "Enhancing PCR Amplification and Sequencing Using DNA-Binding Proteins," Molecular Biotechnology, 1994, vol. 2, pp. 295-298.

Rees W.A., et al., "Betaine can Eliminate the Base Pair Composition Dependence of DNA Melting," Biochemistry, 1993, vol. 32, No. 1, pp. 137-144.

Reinhartz A., et aL, "A Novel Rapid Hybridization Technique: Paper Chromatography Hybridization Assay (PACHA)," Gene, Elsevier Science Publishers B.V, 1993, vol. 136, pp. 221-226.

Rodriguez J.L.M., et al., "Detection and Diversity Assessment of Xylella fastidiosa in Field-Collected Plant and Insect Samples by Using 16S rRNA and gyrB Sequences," Applied and Environmental Microbiology, American Society for Microbiology, Jul. 2003, vol. 69 (7), pp. 4249-4255.

Romero A., et al., "Amplification and Cloning of a Long RNA Virus Genome Using Immunocapture—Long RT-PCR," Journal of Virological Methods, Elsevier Science B.V, 1997, vol. 66, pp. 159-163.

Roper M.G., et al., "Advances in Polymerase Chain ReAction on Microfluidic Chips," Analytical Chemistry, American Chemical Society, 2005, vol. 77 (12), pp. 3887-3894.

Rouse R., et aL, "Microarray Technologyan Intellectual Property Retrospective," Pharmacogenomics, Ashley Publications Ltd , 2003, vol. 4 (5), 10 pages.

Rule, G.S., et aL, "Rapid Method For Visual Identification of Specific DNA Sequences Based on DNA-Taqqed Liposomes," Clinical Chemistry, 1996, vol. 42 (8), pp. 1206-1209.

Saiki R.K., et al., "Primer-Directed Enzymatic Amplification Of DNA With A Thermostable DNA Polymerase," Science, Jan. 29, 1988, vol. 239, No. 4839, pp. 487-491.

Sambrook, et al., "Molecular Cloning: A Laboratory Manual," 3rd Edition, Cold Spring Harbor Laboratory Press, 2001, pp. 9.47-9.55.

Sarkar G., et al., "Formamide can Dramatically Improve the Specificity of PCR," Nucleic Acids Research, 1990, vol. 18 (24), p. 7465.

Schildkraut C., et al., "Dependence of The Melting Temperature of DNA on Salt Concentration," Biopolymers, 1965, vol. 3, pp. 195-208.

Schuchard M., et al., "Two-Step "Hot" PCR Amplification of GC-Rich Avian c-myc Sequences," BioTechniques, Mar. 1993, vol. 14 (3), 4 pages.

Schwab K.J., et al., "Immunoaffinity Concentration and Purification of Waterborne Enteric Viruses for Detection By Reverse Transcriptase PCR," Applied and Environmental Microbiology, Jun. 1996, vol. 62, No. 6, pp. 2086-2094.

Shoffner M.A., et al., "Chip Pcr. I. Surface Passivation of Microfabricated Silicon-Glass Chips for PCR," Nucleic Acids Research, 1996, vol. 24, No. 2, pp. 375-379.

Singh S.K., et al., "LNA (Locked Nucleic Acids): Synthesis And High-affinity Nucleic Acid Recognition," Chemical Communications, 1998, vol. 4, pp. 455-456.

Spiess L., et al., "Trehalose Is a Potent PCR Enhancer: Lowering of DNA Melting Temperature and Thermal Stabilization ofTaq Polymerase by the Disaccharide Trehalose," Clinical Chemistry, 2004, vol. 50 (7), pp. 1256-1259.

Spiro A., et al., "A Bead-Based Method for Multiplexed Identification and Quantitation of DNA Sequences Using Flow Cytometry," Applied and Environmental Microbiology, American Society for Microbiology, Oct. 2000, vol. 66, No. 10, pp. 4258-4265.

(56) References Cited

OTHER PUBLICATIONS

Stears, R.L., et al., "A Novel, Sensitive Detection System For High-Density Microarrays Using Dendrimer Technology," Physiological Genomics, American Physiological Society, 2000, vol. 3, pp. 93-99.
Sterne M., "The Use of Anthrax Vaccines Prepared from Avirulent (Uncapsulated) Variants of Bacillus anthracis," Onderstepoort Journal of Veterinary Science and Animal Industry, Government Printer, Pretoria, Union of South Africa, Oct. 1939, vol. 13 (2), 6 pages.
Stiver G., "The Treatment of Influenza with Antiviral Drugs," CMAJ, Canadian Medical Association, Jan. 7, 2003, vol. 168 (1), pp. 49-57.
Sunen E., et al., "Recovery and Detection of Enterovirus, Hepatitis A virus and Norwalk virus in Hardshell Clams (*Mercenaria mercenaria*) by RT-PCR Methods," Journal of Virological Methods, 1999, vol. 77, pp. 179-187.
Tennikova T.B., et al., "An Introduction to Monolithic Disks as Stationary Phases for High Performance Biochromatography," Journal of High Resolution Chromatography, WILEY-VCH Verlag GmbH .Jan. 2000, vol. 23, pp. 27-38.
Tennikova T.B., et al., "High-Performance Membrane Chromatography: Highly Efficient Separation Method for Proteins In Ion-Exchange, Hydrophobic Interaction and Reversed-Phase Modes," Journal of Chromatography, Elsevier Science Publishers B.V, 1993, vol. 646, pp. 279-288.
Thommes J., et al., "Membrane Chromatography—An Integrative Concept in the Downstream Processing of Proteins," Biotechnology Progress, American Chemical Society and American Institute of Chemical Engineers, 1995, vol. 11 (4), pp. 357-367.
Tsai Y.L., et aL, "Rapid Method for Separation of Bacterial DNA from Humic Substances in Sediments for Polymerase Chain Reaction," Applied and Environmental Microbiology, American Society for Microbiology , Jul. 1992, vol. 58 (7), pp. 2292-2295.
Varadaraj K., et al., "Denaturants Or Cosolvents Improve The Specificity Of PCR Amplification Of A G+c-rich DNA Using Genetically Engineered DNA Polymerases," Gene, Mar. 11, 1994, vol. 140, No. 1, pp. 1-5.
Vincent M., et al., "Helicase-Dependent Isothermal DNA Amplification," EMBO Reports, European Molecular Biology Organization, 2004, vol. 5 (8), pp. 795-800.
Wahlestedt C., et al., "Potent and Nontoxic Antisense Oligonucleotides Containing Locked Nucleic Acids," Proceedings of the National Academy of Sciences of the United States of America, May 9, 2000, vol. 97 (10), pp. 5633-5638.
Walker G.T., et al., "Isothermal in Vitro Amplification of DNA by Restriction Enzyme/DNA Polymerase System," Proceedings of the National of Academy of Sciences USA, Jan. 1992, vol. 89, pp. 392-396.
Walker G.T., et al., "Strand Displacement Amplification—An Isothermal, in Vitro DNA Amplification Technique," Nucleic Acids Research, 1992, vol. 20, No. 7, pp. 1691-1696.
Wang W., et al., "Droplet-Based Micro oscillating-flow PCR Chip," Journal of Micromechanics and Microengineering, 2005, vol. 15, pp. 1369-1377.
Webby R. J., et al., "Are We Ready for Pandemic Influenza?," Science, Nov. 28, 2003, vol. 302, pp. 1519-1522.
Webster R.G., et al., "Potential Impact of Antiviral Drug Use during Influenza Pandemic," American Scientist, Mar.-Apr. 2003, vol. 91, pp. 122-129.
Wei C.Y., et al., "Using a Microfluidic Device for 1 ul DNA Micrarray Hybridization in 500 s," Nucleic Acids Research, Oxford University Press, 2005, vol. 33 (8), 11 pages.
Weighardt F., et al., "A Simple Procedure for Enhancing PCR Specificity," PCR Methods and Applications, 1993, vol. 3 (1), pp. 77-81.
Wells J.M., et al., "Isolation, Culture, and Pathogenicity of the Bacterium Causing Phony Disease of Peach," Phytopathology, American Phytopathological Society, 1983, vol. 73 (6), pp. 859-862.
Wetzel T., et al., "A Highly Sensitive Immunocapture Polymerase Chain ReAction Method For Plum Pox Potyvirus Detection," Journal of Virological Methods, Elsevier Science Publishers B.V, Jul. 1992, vol. 39, pp. 27-37.
Wickenheiser R.A., "Trace DNA: A Review, Discussion of Theory, and Application of the Transfer of Trace Quantities of DNA Through Skin Contact," Journal of Forensic Sciences, ASTM Int'l, 2002, vol. 137 (1), pp. 442-450.
Wilding P., et al., "PCR in a Silicon Microstructure," Clinical Chemistry, 1994, vol. 40 (9), pp. 1815-1818.
Wilson I.G., "Inhibition and Facilitation of Nucleic Acid Amplification," Applied and Environmental Microbiology, Oct. 1997, vol. 63 (10), pp. 3741-3751.
Yang S., et al., "PCR-Based Diagnositcs for Infectious Diseases: Uses, Limitations, and Future Applications in Acute-Care Settings," The Lancet Infectious Diseases, Jun. 2004, vol. 4, pp. 337-348.
Young C.C., et al., "Polyvinylpyrrolidone-Agarose Gel Electrophoresis Purification of Polymerase Chain ReAction-Amplifiable DNA from Soils," Applied and Environmental Microbiology, American Society for Microbiology, Jun. 1993, vol. 59 (6), pp. 1972-1974.
Zaytseva N.V., et al., "Multi-Analyte Single-Membrane Biosensor for the Serotype-Specific Detection of Dengue Virus," Analytical and Bioanalytical Chemistry, 2004, vol. 380, pp. 46-53.
Zeng Z., et al., "High Gc Amplification: A Comparative Study Of Betaine, DMSO, Formamide And Glycerol As Additives," Life Science Journal, 2006, vol. 3, No. 1, pp. 67-71.
Zhang C., et al., "PCR Microfluidic Devices For DNA Amplification," Biotechnology Advances, May-Jun. 2006, vol. 24, No. 3, pp. 243-284.
Zijlmans H.J., et al., "Detection Of Cell And Tissue Surface Antigens Using Up-converting Phosphors: A New Reporter Technology," Analytical Biochemistry, Feb. 1, 1999, vol. 267, pp. 30-36.
Zuiderwijk M., et al., "An Amplication-Free Hybridization-Based DNA Assay To Detect *Streptococcus pneumoniae* Utilizing The Up-converting Phosphor Technology," Clinical Biochemistry, Jul. 2003, vol. 36, pp. 401-403.

\* cited by examiner

OSCILLATING AMPLIFICATION REACTION FOR NUCLEIC ACIDS

CROSS-REFERENCE TO RELATED APPLICATIONS

This application is a continuation of U.S. application Ser. No. 17/696,027, filed Mar. 16, 2022. U.S. application Ser. No. 17/696,027 is a continuation of U.S. application Ser. No. 16/377,749, filed on Apr. 8, 2019, and issued on Apr. 5, 2022 as U.S. Pat. No. 11,293,058. U.S. Pat. No. 11,293,058 is a continuation of U.S. Application Ser. No. 15/247,728, filed on Aug. 25, 2016, and issued on Jun. 11, 2019, as U.S. Pat. No. 10,316,358. U.S. Pat. No. 10,316,358 is a continuation of U.S. application Ser. No. 14/113,200, filed on Oct. 21, 2013, and issued on Aug. 30, 2016, as U.S. Pat. No. 9,428,781. U.S. Pat. No. 9,428,781 claims benefit of PCT Application Number PCT/US2012/034589, filed on Apr. 20, 2012. PCT/US2012/034589 claims the benefit of U.S. Provisional Patent Application No. 61/477,437, filed on Apr. 20, 2011, and of U.S. Provisional Patent Application No. 61/477,357, filed on Apr. 20, 2011. All applications identified in this section are incorporated herein by reference, each in its entirety.

STATEMENT REGARDING FEDERALLY SPONSORED RESEARCH OR DEVELOPMENT

Not Applicable

INCORPORATION BY REFERENCE OF MATERIAL SUBMITTED ON A COMPACT DISC

Not Applicable.

COPYRIGHTED MATERIAL

Not Applicable

REFERENCE TO A SEQUENCE LISTING, A TABLE, OR COMPUTER PROGRAM

This application contains nucleotide sequence and/or amino acid sequence disclosure computer readable form and a written sequence listing, which has been submitted as a file in ST.26 XML format through the Patent Center; the contents of which is expressly incorporated by reference in its entirety herein. Said XML file was created on May 2, 2024, is 16,384 bytes in size and has been entered as a file named TP102778USCON4.xml.

BACKGROUND OF THE INVENTION

Field of the Invention (Technical Field)

Embodiments of the present invention relate to methods and apparatuses for template-dependent amplification of nucleic acid target sequences by oscillating reaction temperature in a small range, preferably no more than 20° C. during any given thermal polymerization cycle.

BACKGROUND ART

Note that the following discussion refers to a number of publications and references. Discussion of such publications herein is given for more complete background of the scientific principles and is not to be construed as an admission that such publications are prior art for patentability determination purposes.

Amplification of nucleic acids is among the most indispensible techniques in molecular biology, widely used in research, genetic testing, agriculture, and forensics. The most common amplification method is the polymerase chain reaction (PCR) in which the prevalence of a specific nucleic acid target sequence is increased exponentially in solution (See U.S. Pat. Nos. 4,683,195, 4,683,202, and 4,800,159). A PCR reaction employs two oligonucleotide primers that hybridize to opposite strands of the DNA double helix either upstream (5') or downstream (3') of the target sequence to be amplified. A (generally thermostable) DNA polymerase is used to extend hybridized primers in the 5'.fwdarw.3' direction by adding deoxynucleoside-triphosphates (dNTPs) in order to 'copy' the target sequence and generate double-stranded DNA products. By cycling the temperature of the reaction mixture (typically 95° C. Celsius), the two strands of DNA can be separated at high temperature allowing them to serve as templates for further primer binding and polymerization at lower temperatures (e.g. 55° C. and 60° C.). After repeating this process many times, a single target sequence can be amplified into billions of copies.

While PCR is the gold-standard amplification methodology in the well-equipped laboratory, it is rather complex, requiring both expensive and sophisticated thermal cycling instrumentation with active heating and cooling heating elements and precise temperature control, and trained technicians to gather meaningful results. For instance, most PCR reaction requires rapid and precise cycling between at least two temperatures (e.g. 95 deg and 57 deg), that typically results in the use of an expensive and energy-inefficient Peltier engine (thermal electric cooling mechanism) and precise temperature control elements. Such inherent limitations make PCR incompatible with the development of cost-effective, point-of-care nucleic acid diagnostics—useful where a supporting laboratory infrastructure is absent. In an effort to eliminate some of the resource-intensive requirements of PCR, various 'isothermal' amplification techniques have been developed in the past decades. In such reactions, nucleic acids may be amplified at a single temperature, removing the requirement of the costly thermocycler, and making them more amenable for use in low-cost diagnostic devices. Examples include nucleic acid sequence-based amplification (NASBA), helicase-mediated amplification, strand displacement amplification, loop-mediated isothermal amplification (LAMP) etc. However, these isothermal amplification methods often require 60-90 minute amplification time (due to slow kinetic enzymatic process in vitro) and precise temperature control at the single temperature point to accommodate the extremely stringent amplification reactions, again lacking the robustness and speed desired for the point of use diagnostic application.

Template-dependent nucleic acid amplification is the cornerstone of the nucleic acid-based molecular diagnostics. Robust, low cost, rapid, point-of-care nucleic acid diagnostics are a pressing need in health care, agriculture, and in the context of biological terrorism and warfare. However, the assay chemistry strategies associated with the existing PCR or isothermal amplification posse significant engineering and robustness limitations rendering such amplification approaches expensive and impractical for the resource-limited settings where nucleic acid-based molecular could make the most impact for emerging disease prevention and control. Considerable improvements in nucleic acid amplification must yet be made to bring affordable and robust diagnostics to settings devoid of dedicated laboratory infrastructure.

Conventional PCR relies on highly specific and rapid thermal cycling, commonly varying temperature by as much as 40° C. Such an amplification methodology requires expensive instrumentation in order to rapidly heat and (particularly) cool the PCR reaction mixture, in addition to accurately maintaining solution temperatures. Isothermal nucleic acid amplification procedures, while eliminating the need for complex thermal cycling instrumentation, are generally slow (at least 60 minute reaction time), unreliable, and require precise temperature calibration.

In a PCR thermal cycling process, a PCR cycler must have a good temperature control to maintains temperature uniformity within the sample and a typical sample heating (and/or cooling) rate of at least 2° C. per second. Temperature control is typically achieved by a feedback loop system, while temperature uniformity is achieved by highly thermally conductive but bulky materials such as copper. A high heating rate is accomplished by the implementation of a proportional integrated derivative (PID) control method limited by maximum dissipated power and heat capacitance. A high cooling rate is rather difficult to achieve and bulky systems require forced cooling by either a thermoelectric element (P. Wilding, M. A. Shoffner and L. J. Kricka, Clin. Chem., 1994, 40, 1815-1817.)(often called a Peltier element) or by other means, such as water (J. B. Findlay, S. M. Atwood, L. Bergmeyer, J. Chemelli, K. Christy, T. Cummins, W. Donish, T. Ekeze, J. Falvo, D. Patterson, J. Puskas, J. Quenin, J. Shah, D. Sharkey, J. W. H. Sutherland, R. Sutton, H. Warren and J. Wellman, Clin. Chem., 1993, 39, 9, 1927-1933). These PCR machines are complicated and power hungry devices. As the systems are bulky, their thermal time constants are in minutes rather than seconds which result in long transition times and unwanted by-products of the PCR. The high power consumption eliminates the possibility of making a battery operated and portable PCR system.

With the recent advancement of silicon technology based micromachining and biological micro-electromechanical systems (bioMEMS), many groups around the world have started the development of microPCRs (uPCR), which are a central part of a lab-on-a-chip or micro total analysis systems (pTAS). Researchers follow two basic approaches: a stationary system with cycling temperature a flow system with three zones at different temperatures. Both systems have their advantages and disadvantages. Stationary systems cycle the temperature of the chamber in order to modify the temperature of the PCR solution. They do not require a pumping system or other means to move the PCR sample around. The flow-through systems typically have zones at three constant temperatures. Only the sample changes temperature by moving between zones of different temperatures. This type of PCR system is faster than the first one but it requires an implementation of a mechanism to move the sample around. In both cases, the heaters are integrated with the PCR system, so it is not economical to dispose the device to avoid cross-contamination after performing only a single test. The major advantages demonstrated by these two formats are reduced cycle time with the use of reduced sample volume compared to a conventional device. However, these PCR chips use substrate materials such as silicon that require the employment of expensive and sophisticated fabrication process, leading to a very high unit price. Furthermore, as a result of extreme small reaction volume (<µl) to achieve increased surface to volume ratio and the type of materials used in the µ.PCR chips, some effects not very common with the conventional PCRs become significant, including nonspecific adsorption of biological samples, inhibition, sample evaporation, and formation of bubbles. Other current effort also involves the development of a temperature cycling reaction microchip that integrates stationary chamber and continuous flow PCRs to perform efficient temperature cycling of the flow-through microchannel PCR chip while the flexibility of varying the cycle number and the number of temperature zones in the stationary chamber PCR chip. However, the efficiency of the hybrid PCR device is still being validated and issues related to sample inhibition, adsorption, and bubble formation associated with such µPCR chip approach remain to poses significant stringency to all the upfront sample preparation/nucleic acid isolation process, and amplification reagents and reaction conditions e.g. ultra high polymerase concentration, PCR primer concentrations etc.

SUMMARY OF THE INVENTION

One embodiment of the present invention provides for a method for amplifying a template of nucleic acid target sequence contained in a sample. The method includes contacting the sample with an amplification reaction mixture containing a primer complementary to the template of nucleic acid target sequence. A temperature of the reaction is oscillated between an upper temperature and a lower temperature wherein the change in temperature is no greater than about 20° C. during a plurality of temperature cycles. The template of nucleic acid target sequence is amplified.

One embodiment of the present invention provides that the change in temperature is no greater than about 15° C. during a plurality of temperature cycles. Another embodiment provides that the change in temperature is no greater than about 10° C. during a plurality of temperature cycles. Yet another embodiment provides that the change in temperature is no greater than about 5° C. during a plurality of temperature cycles. The temperature may fluctuate by (+/− 2° C.) for a given temperature and/or range according to one embodiment of the present invention.

Another embodiment of the present invention provides that upon reaching the upper temperature or the lower temperature, the temperature is maintained for a set period of time within a temperature fluctuation. Alternatively, upon reaching an upper or lower temperature within the temperature range, the temperature is varied to the other temperature. In one embodiment, the lower temperature is no less than about 50° C. In another embodiment, the upper temperature is no greater than about 85° C. The upper and lower temperature may vary by about +/−5° C. according to one embodiment.

According to one embodiment of the present invention the template of nucleic acid target sequence may be single stranded DNA or RNA, double stranded DNA or RNA, RNA, DNA or any combination thereof. The length of the target nucleic acid may be less than 1000 bp, less than 250 bp, less than 150 bp or less than 100 bp.

One or more of the embodiments may comprise a pair of primers which bind to opposite strands of the template of nucleic acid. The pair of primers may have a length and a GC content so that the melting temperature is 65° C. In another embodiment, the pair of primers have a length and a GC content so that the melting temperature is 70° C. For example, each primer of the pair of primers independently has a length of between 35-70 base pairs. According to one embodiment of the present invention, the melting temperature of each primer of the primer pair is between 70-80° C. In a preferred embodiment, the pair of primers include a forward primer and a reverse primer each having a length of between 40-47 base pairs.

Yet another embodiment of the present invention provides a method for amplifying a template of nucleic acid target sequence contained in a sample. The method includes contacting the sample with an amplification reaction mixture comprising a primer or a primer pair having a length of between 35-70 base pairs and complementary to the template of the nucleic acid target sequence and wherein the melting temperature of each primer of the primer pair is between 70-80° C. The amplification reaction mixture also includes DMSO, monovalent cation, divalent cation, dNTPs, and DNA Polymerase. A temperature of the reaction is oscillated between an upper temperature and a lower temperature wherein the change in temperature is no greater than about 20° C. during a plurality of temperature cycles and amplifying the template of nucleic acid target sequence. In a preferred embodiment, the divalent cation is selected from the group consisting of magnesium, manganese, copper, zinc or any combination thereof and the monovalent cation is selected from the group consisting of sodium, potassium, lithium, rubidium, cesium, ammonium or any combination thereof. In another preferred embodiment, the amplification reaction mixture comprises a nucleic acid destabilizing agent. In a more preferred embodiment the reaction comprises a DNA polymerase which may be a thermostable DNA polymerase. The DNA polymerase may be selected from the group consisting of TAQ DNA polymerase, VentR DNA polymerase, and DeepVentR DNA polymerase but is not limited thereto as other polymerases disclosed herein and known in the art may be included. The DNA polymerase may include a strand displacing activity. In another embodiment, the DNA polymerase does not have 3'→5' exonuclease activity. In another embodiment, the method for amplifying a template further comprises adding a reverse transcriptase and a DNA polymerase. For example, the reverse transcriptase is a thermostable reverse transcriptase. The reverse transcriptase may be selected from AMV-RT, Superscript II reverse transcriptase, Superscript III reverse transcriptase, or MMLV-RT but is not limited thereto as other reverse transcriptases known in the art may be used. Another embodiment of the present invention further comprises the addition of a single stranded binding protein to the reaction mixture as disclosed. For example, the single stranded binding protein is a thermal stable single stranded binding protein or the single stranded binding protein is a non-thermal stable single stranded binding protein.

Yet another embodiment of the present invention provides a mixture which includes a single strand or double strand nucleic acid destabilizing agent. For example dimethylsulfoxide (DMSO) or formamide but not limited thereto as other agents such as glycerol may be added for the same purpose.

Another embodiment of the present invention provides a method wherein the sample is not alcohol free and or the sample is not salt free.

Yet another embodiment of the present invention provides a method for amplifying a template of nucleic acid target sequence contained in a sample wherein the amplification reaction mixture comprises single strand or double strand nucleic acid destabilizer; monovalent cation; divalent cation; dNTPs and DNA Polymerase buffered at a pH to support activity.

Another embodiment of the present invention provides an amplification reaction mixture buffer comprising one or more of the following: single strand or double strand nucleic acid destabilizer; monovalent cation; divalent cation; dNTPs; and DNA Polymerase buffered at a pH to support activity. The DNA polymerase may be a thermostable DNA polymerase. The DNA polymerase may be selected from the group consisting of TAQ DNA polymerase, VentR DNA polymerase, and DeepVentR DNA polymerase but not limited thereto. The DNA polymerase may have a strand displacing activity. The DNA polymerase may be selected which does not have 3'→5' exonuclease activity. The mixture may also include one or more of the following: a single stranded binding protein, a destabilizing agent is dimethylsulfoxide (DMSO) or formamide; a divalent cation which may be a salt selected from the group consisting of magnesium, manganese, copper, zinc or any combination thereof, and a monovalent cation which is a salt selected from the group consisting of sodium, potassium, lithium, rubidium, cesium, ammonium or any combination thereof.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate an embodiment of the present invention and, together with the description, serve to explain the principles of the invention. The drawings are only for the purpose of illustrating a preferred embodiment of the invention and are not to be construed as limiting the invention. In the drawings.

DETAILED DESCRIPTION OF THE INVENTION

Figure 1A:
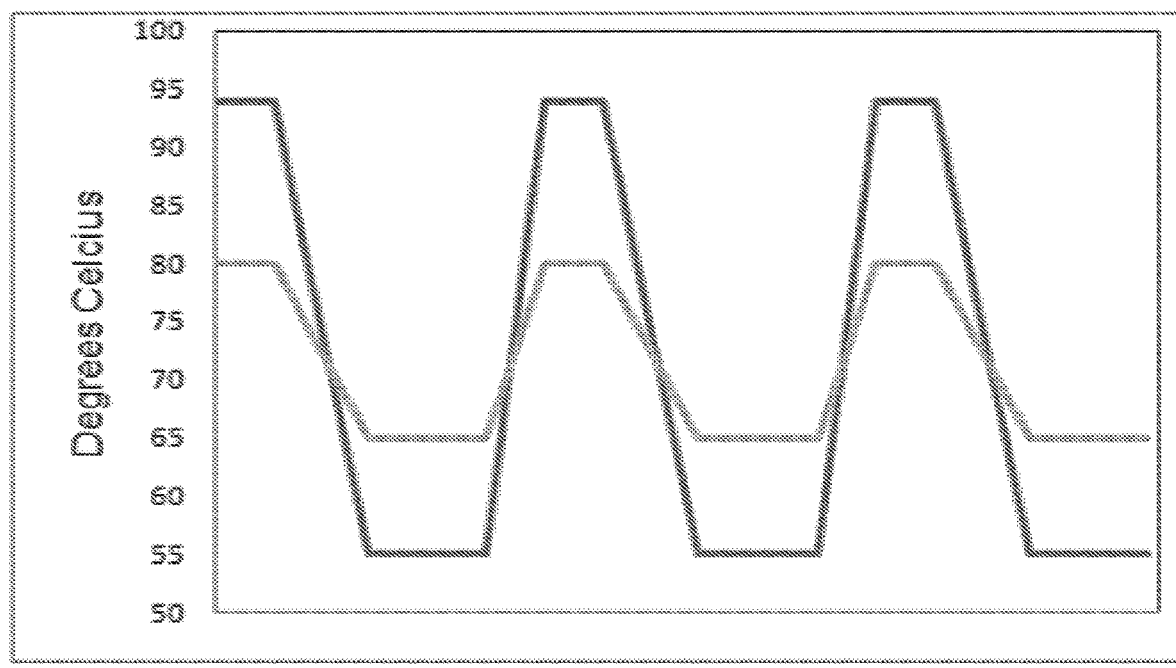
FIG. 1A Illustrates a schematic diagram of an Oscillating PCR Amplification Reaction according to one embodiment of the present invention, a representative trace of the thermal fluctuations observed during several cycles of OPCRar (gray line), in comparison with a conventional two-stage PCR reaction (black line).

As used throughout the specification and claims, the term 'nucleic acid' means single stranded or double stranded DNA, RNA, or DNA/RNA hybrid molecules. Single stranded nucleic acids may have secondary structure such as hairpin, loop, and stem elements. Double stranded or single stranded nucleic acids may be linear or circular. Double stranded nucleic acids may be intact or nicked. Double stranded molecules may be blunt-ended or have single strand overhanging ends. Nucleic acid samples may be isolated from cells or viruses and may include chromosomal DNA, extra-chromosomal DNA including plasmid DNA, recombinant DNA, DNA fragments, messenger RNA, ribosomal RNA, transfer RNA, double stranded RNA or other RNAs that occur in cells or viruses. Nucleic acid may be isolated from any number of sources such as agriculture, food, environmental, fermentations, or biological fluids such as saliva, blood, nasal or lung aspirates, cerebrospinal fluid, sputum, stool, milk, swabs of mucosal tissues, tissue samples, or cells. Nucleic acid may be isolated, cloned or synthesized in vitro. Within the described nucleic acids above, individual nucleotides may be subject to modification or chemical alterations such as methylation. These modifications or alterations may arise naturally or by in vitro synthesis.

As used throughout the specification and claims, the terms 'target nucleic acid' or 'template nucleic acid' mean a single stranded or double stranded DNA or RNA fragment or sequence that is intended to be selectively amplified. The size of the nucleic acid to be amplified is defined by upstream (5') and downstream (3') boundaries and may be less than 500 bp, preferably less than 250 bp, and more preferably less than 150 bp and more preferably less than 100 bp. The target nucleic acid may be a fragment contained within a longer double stranded or single stranded nucleic acid or may be an entire double stranded or single stranded nucleic acid.

As used throughout the specification and claims, the term 'duplex' means a DNA or RNA nucleic acid molecule that is double stranded in whole or in part.

As used throughout the specification and claims, the term 'thermal cycle' means the repeated temperature fluctuation necessary for nucleic acid amplification to occur. The thermal cycle may include, but is not limited to, a high temperature melting or denaturation step, and a low temperature annealing or hybridization step.

As used throughout the specification and claims, the terms 'melting' or 'denaturation' mean separating all or part of two complementary strands of a nucleic acid duplex with high temperature. The melting or denaturation temperature may be influenced by the length and sequence of the oligonucleotide primer, the concentration of duplex destabilizing reagents such as DMSO and formamide, and the ionic strength or pH of the solution.

As used throughout the specification and claims, the terms 'annealing' or 'hybridization' mean the sequence-specific binding of an oligonucleotide primer to a single-stranded nucleic acid template. The primer may bind only to its complementary sequence on one of the template strands and no other region of the template. The specificity of annealing or hybridization may be influenced by the length and sequence of the oligonucleotide primer, the temperature at which binding is performed, the concentration of duplex destabilizing reagents such as DMSO and formamide, and the ionic strength or pH of the solution.

As used throughout the specification and claims, the term 'primer' means a single stranded nucleic acid or oligonucleotide capable of binding to a single stranded region on a target nucleic acid in a sequence-specific manner that allows polymerase-dependent replication of the target nucleic acid.

As used throughout the specification and claims, the term 'OPCRar' means Oscillating PCR Amplification Reaction which is an in vitro technique for amplifying nucleic acids using variations in temperature less than the typical amplification techniques, for example less than 20° C., preferably less than 15° C. and more preferably less than 10° C. between the denaturation temperature and the annealing temperature.

As used throughout the specification and claims, the term 'accessory protein' refers to any protein capable of stimulating activity, for example, a thermostable single stranded binding protein (SSB), for example rec A or RPA (Replication Protein A but not limited thereto.

In an embodiment of the invention, a method is provided for exponentially amplifying a specific nucleic acid target by thermal cycling where temperature variation is preferably less than 20° C., more preferably less than 15° C., and even more preferably less than 10° C. This includes the steps of providing a single-stranded template of the nucleic acid to be amplified, oligonucleotide primers for hybridization to the nucleic acid template, using the hybridized oligonucleotide primers to synthesize a double-stranded extension product which is complementary to the template strand by means of a DNA polymerase, and repeating of the above steps to exponentially amplify a select nucleic acid target.

Figure 1B:
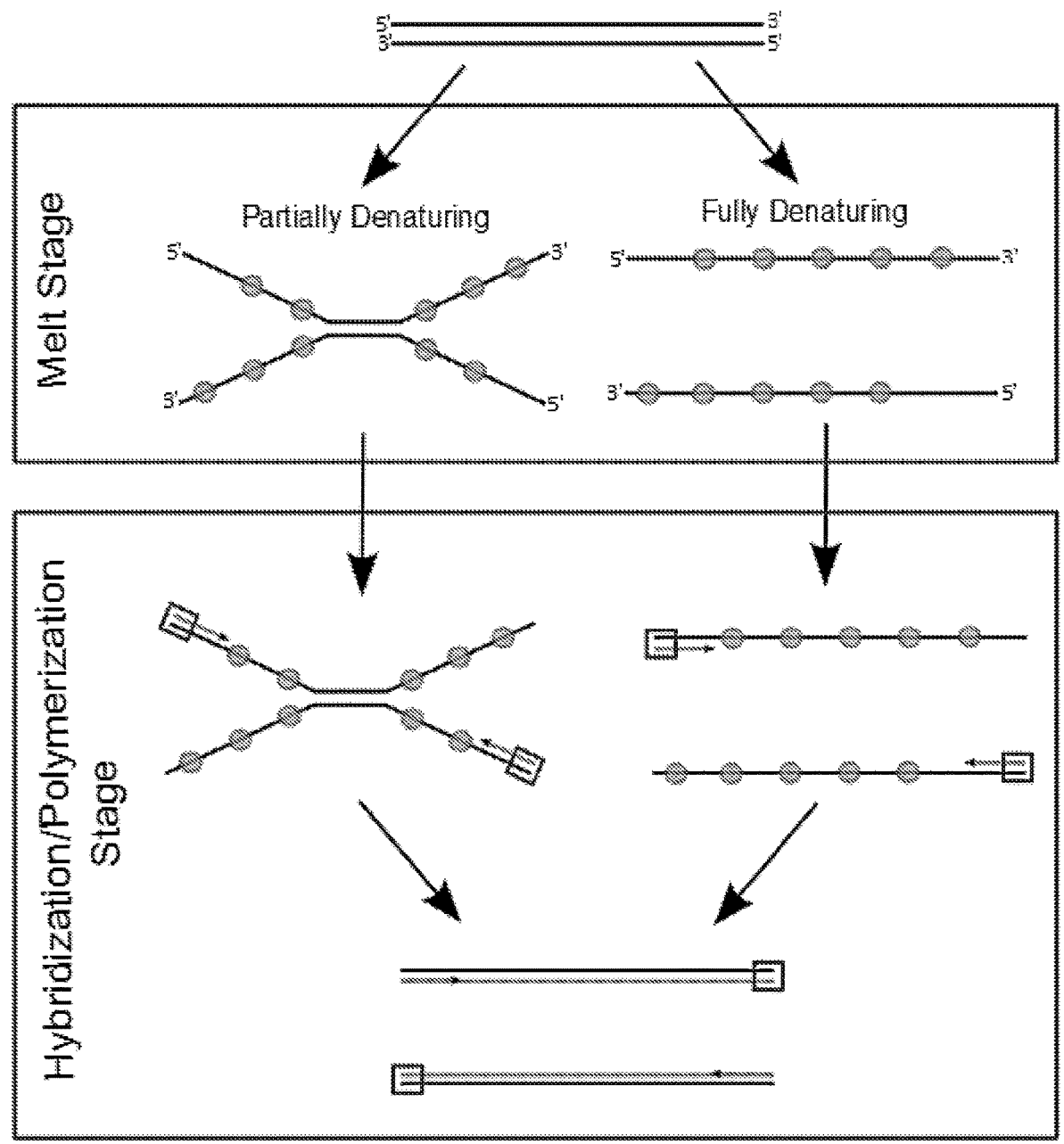
FIG. 1B illustrates a method for nucleotide amplification according to one embodiment of the present invention.
Figure 2A:
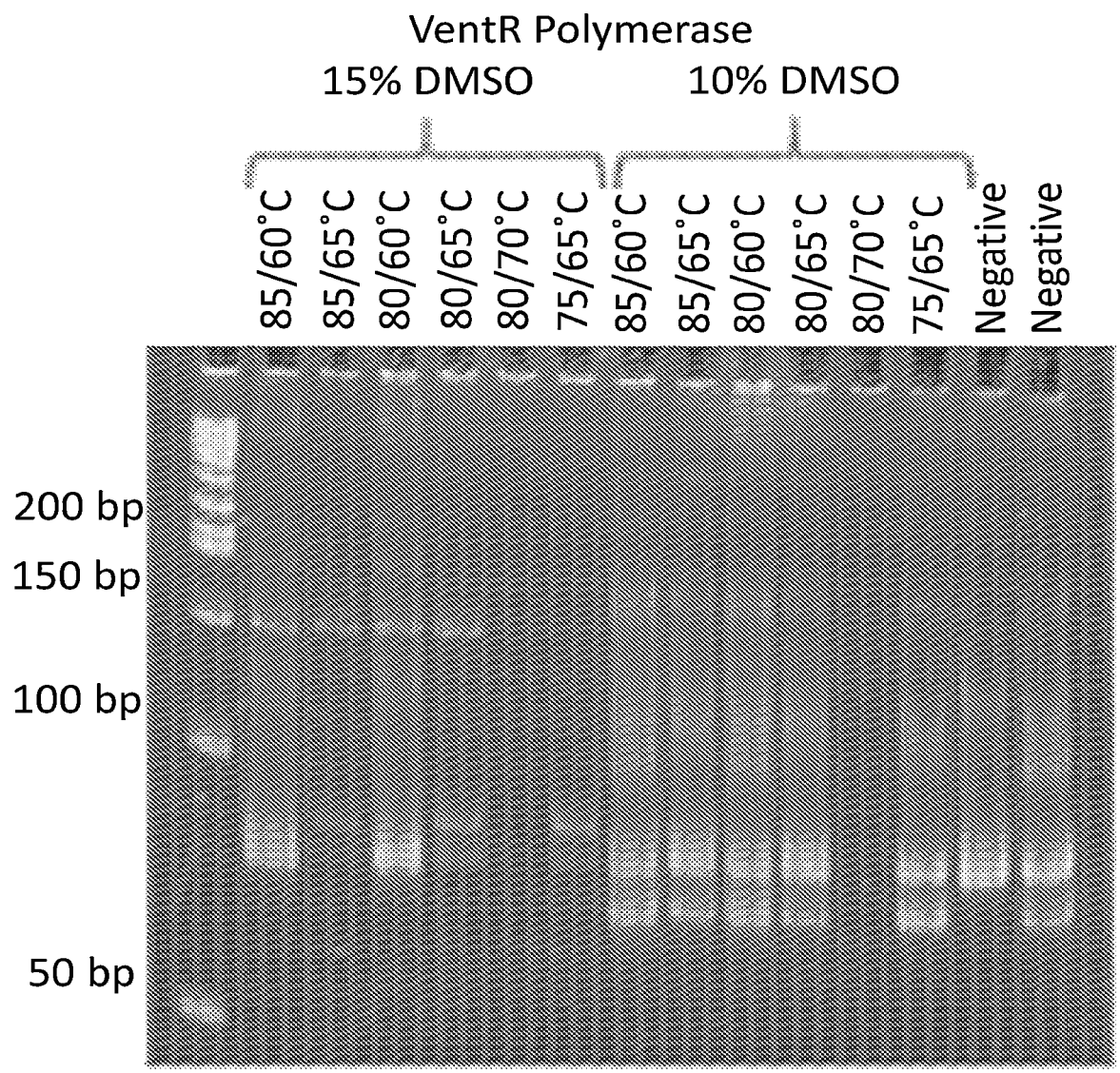
FIGS. 2A-2E represent a series of photos of acrylamide gels illustrating different polymerases used to generate a product of 153 base pair (bp) according to one embodiment of the present invention.
Figure 2B:
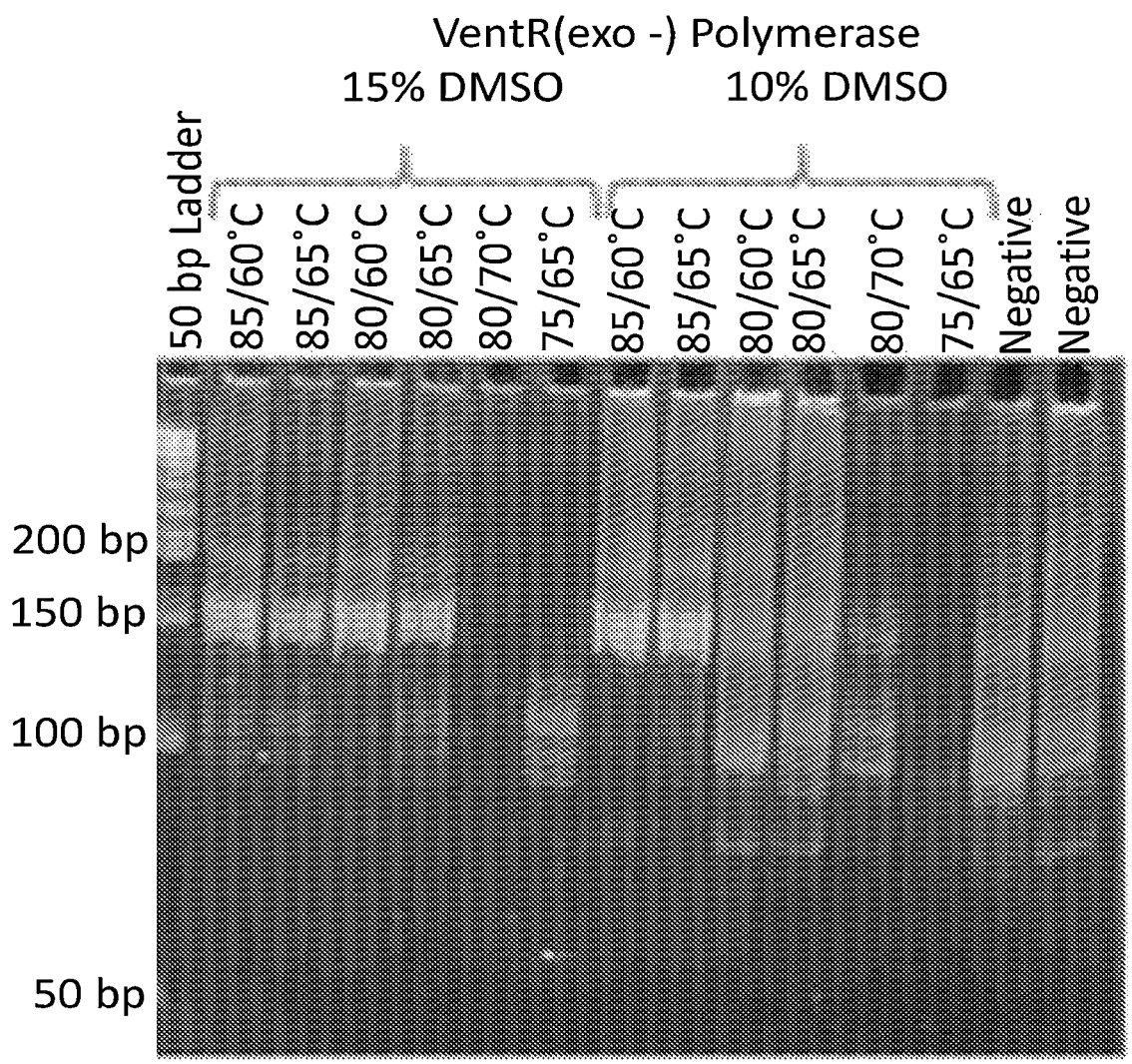
Figure 2C:
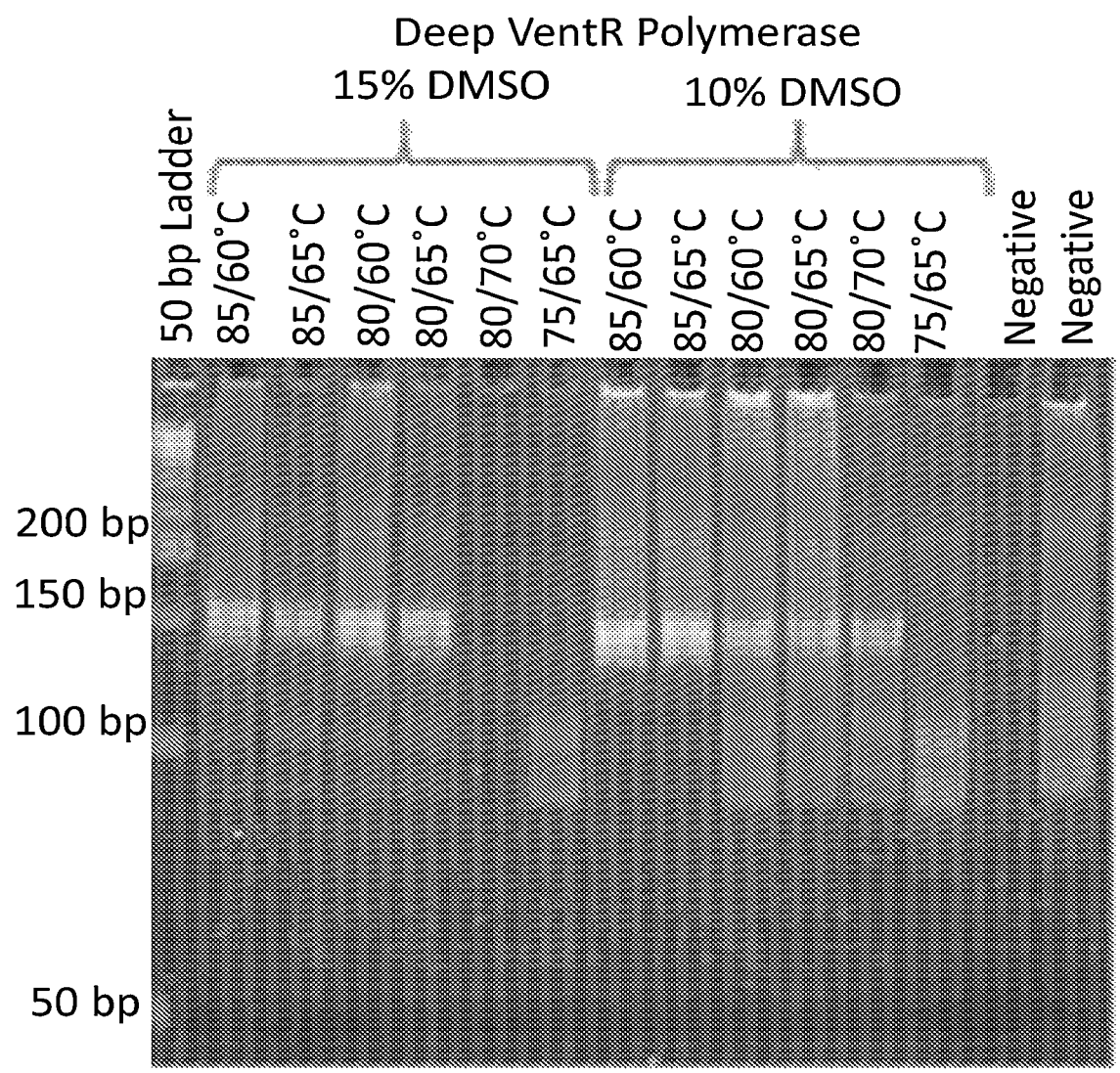
Figure 2D:
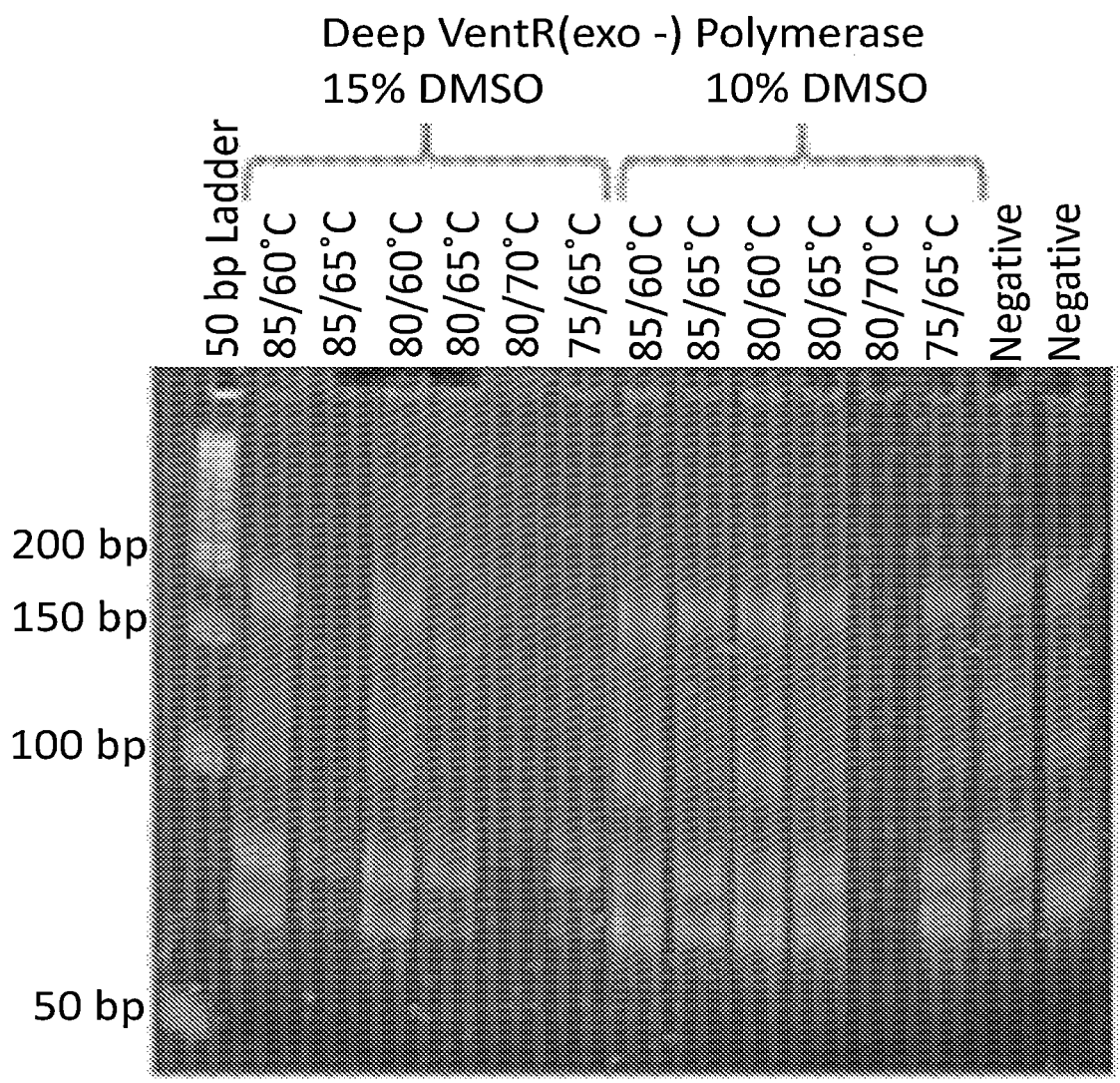
Figure 2E:
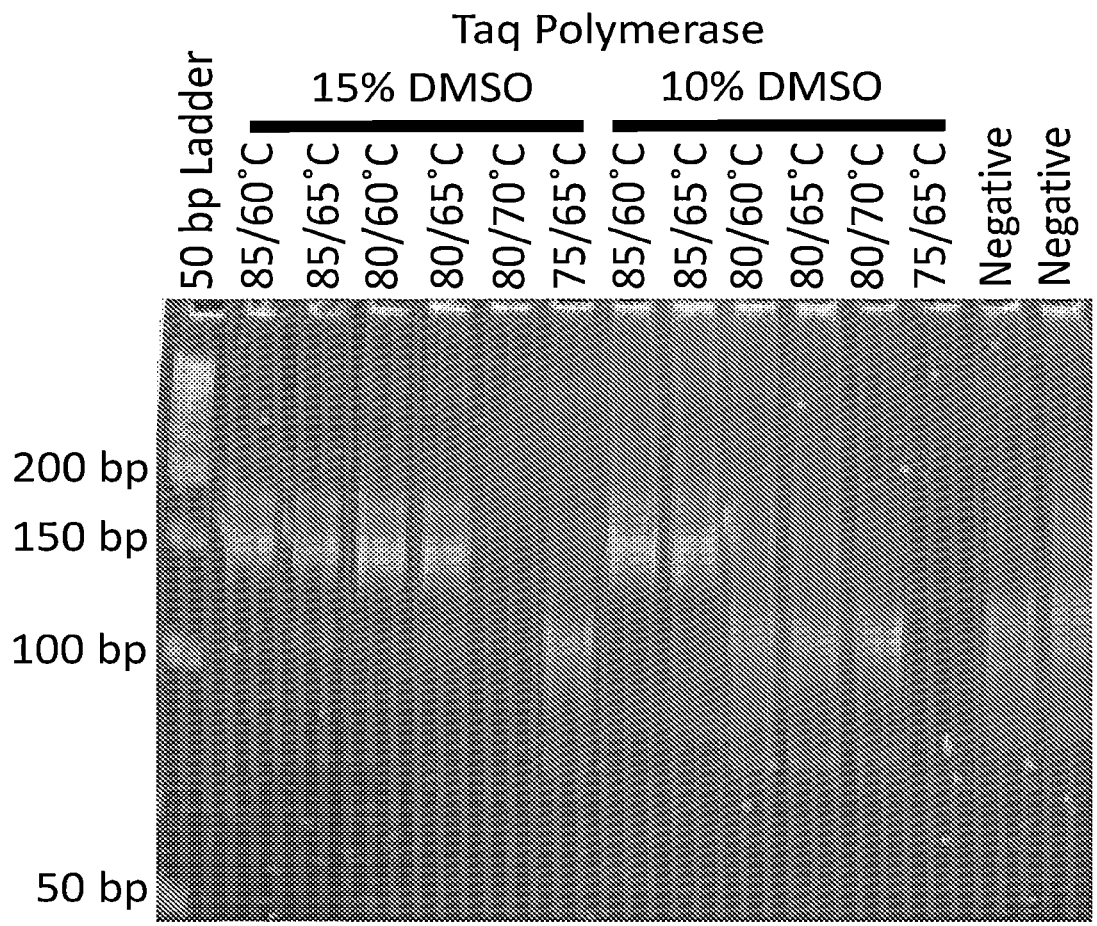

Referring now to FIG. 1A, a schematic diagram of an Oscillating PCR Amplification Reaction (OPCRar) according to one embodiment of the present invention is illustrated with panel A showing a representative trace of the thermal fluctuations observed during several cycles of OPCRar (gray line), in comparison with a conventional two-stage PCR reaction (black line). Note the dramatic reduction in the temperature variation in OPCRar. FIG. 1B illustrates, double stranded target nucleic acid enters the melt stage where, depending on the temperatures, may result in either partial or complete denaturation of the duplex according to one embodiment of the present invention. Unwinding of the duplex begins at the ends of the target and single stranded nucleic acid is bound and stabilized by single stranded binding protein (circles). The reaction is cooled and enters the hybridization/polymerization stage where primers hybridize in a specific manner to the 5' ends of each strand of the target duplex. After primer hybridization, DNA polymerase (squares) binds to the template/primer duplex and extends the primer in the 5'.fwdarw.3' direction by incorporation of dNTPs, copying the template stand of DNA. If the polymerase used has strand displacement activity, it will be able to displace the opposing strand in the partially denatured complex. Upon generation of new duplex DNA, the thermal cycle is repeated many times to result in exponential amplification of the target nucleic acid sequence.

In additional embodiments of the invention, thermal cycling involves temperature oscillation or cycling between two temperatures with a .DELTA.T of preferably no more than 20° C., more preferably no more than 15° C., and even more preferably less than 10° C. The higher of the two temperatures may be sufficient to denature the double stranded target DNA, or preferably result in only partial denaturation of the double stranded DNA target. Upon reaching either the high or low temperature, said temperature is maintained for a set period of time or, preferably, immediately varied to the other temperature.

In additional embodiments of the invention, the nucleic acid target may be a double stranded nucleic acid such as double stranded DNA, or a single stranded nucleic acid such as single stranded RNA or DNA. If the target nucleic acid is double stranded, it must be denatured either entirely or partially by heat, or enzymatically, to form a single stranded template or template region necessary for DNA polymerase activity and amplification. The length of the target nucleic acid may be less than 1000 bp, preferably less than 250 bp, and more preferably less than 150 bp.

In additional embodiments of the invention, the oligonucleotide primers used for target nucleic acid amplification are a pair of primers which bind to opposite strands of a specific double stranded target nucleic acid, where one primer binds upstream at the 5' end, and one primer binds downstream at the 3' end of the target. Under multiplexing conditions, more than one oligonucleotide primer pair may be used to simultaneously amplify multiple nucleic acid targets in the same reaction mixture. The oligonucleotide primers may have a length and GC content so that the melting temperature is greater than 65° C. under universally accepted PCR buffer conditions, preferably greater than 70° C.

In additional embodiments of the invention, the DNA polymerase used is preferably selected from Taq DNA polymerase, VentR DNA polymerase, DeepVentR DNA polymerase, and similar thermostable DNA polymerases. Preferably, the DNA polymerase possesses a strand-displacing activity and does not contain a 3'.fwdarw.5' exonuclease activity (see FIG. 1B). In addition, if the template nucleic acid is single stranded RNA, the reverse transcriptase used will be selected from AMV-RT, Superscript II reverse transcriptase (Invitrogen, Carlsbad, Calif.), Superscript III reverse transcriptase (Invitrogen), and similar thermostable enzymes.

Other—Thermalphilic Polymerase Possibilities
  Thermophilic DNA Polymerase
  Polymerase and (Vender)
  VentR® (NEB)
  VentR (exo-)® (NEB)
  Deep Vent (NEB)
  Deep VentR (exo-) (NEB)
  Tag (NEB)
  PyroScript (Lucigen)
  PyroPhage® 3173, Wildtype (Lucigen)
  LongAmp Tag (NEB)
  Bst Polymerase
  Phire Hot Start II (NEB)
  Phusion High Fidelity DNA Polymerase (NEB)
  Phusion (NEB)
  Phusion® Flash (NEB)
  9 Nm (NEB)
  DyNAzyme II Hot Start (NEB)
  DyNAzyme EXT (NEB)
  DreamTag (Fermentas)
  Tag (native) (Fermentas)
  Maxima® Hot Start Tag (Fementas)
  Pfu (recombinant), (Fermentas)
  Bsm (large fragment), (Fermentas)
  TrueStart™ Hot Start Tag (Fermentas)
  Tfi (invitrogen)
  AmpiTag® (Invitrogen)
  AmpliTag Gold® (Invitrogen)
  Platinum® Pfx In additional embodiments of the invention, the reaction mixture preferably comprises a single stranded binding protein (SSB) such as T4 gene 32 protein, or thermal stable SSB isolated and cloned from a themophilic organism.

Additionally, the enzyme preparation includes a single or double stranded nucleic acid destabilizing agent such as dimethylsulfoxide (DMSO) or formamide, preferably at a concentration of 8-15% of the total reaction volume. Alternatively other reagents such as glycerol deaza-dGTP, 3dazopurein, dITP may be utilized alone or in combination with each other or the prior list of agents.

Embodiments of this invention are ideally suited for use in low cost, point-of-care nucleic acid diagnostics in which a microfluidic layer is positioned over a heating element. By reducing temperature range cycling requirements, relatively simple heating with passive cooling mechanisms can be used to rapidly cycle temperature of a reaction solution. Lower maximum temperatures during thermal cycling minimize fluid evaporation which may negatively impact the overall amplification reaction. More importantly, the robustness of the amplification is greatly improved comparing to the conventional PCR process giving the new method is able to accommodate temperature fluctuation (imprecise temperature control) during a amplification process. The specific reaction chemistry of the invention was shown to work over a wide range of melting (e.g. 70-105° C., essentially insensitive to bubbling) and hybridization temperatures eliminating the need for uniform temperature throughout the entire reaction volume. Finally, embodiments of the invention perform well in the presence of alcohol, and salt (e.g.

.about.10% ethanol), greatly reducing the stringency of up-front nucleic acid isolation methodologies through the elimination of a centrifugation, heat-dry or vacuum step between alcohol-based washing (e.g. ethanol or isopropanol) and nucleic acid elution step involved conventional nucleic acid extraction chemistry.

Embodiments of this invention include the detection of pathogens in a biological sample where a nucleic acid of the pathogen is the target nucleic acid. Alternatively, the invention may be used to detect differences in chromosomal DNA, where a fragment of chromosomal DNA is the target nucleic acid. In this way, single nucleotide polymorphisms may be detected in the target nucleic acid from the same or different sources.

Embodiments of the amplification technology of the present invention are referred to as an 'Oscillating PCR Amplification Reaction' (OPCRar). OPCRar is based upon, but not limited to, the combined use of double stranded destabilizing agents which lower the reaction melting temperature, and oligonucleotide primers of unusually high melting temperature (Tm) to raise the annealing temperature in a given thermal cycle. In this way, in vitro amplification of a target nucleic acid may be performed by rapid thermal cycling between temperatures preferably differing by 20° C., more preferably less than 15° C., and even more preferably less than 10° C. (FIG. 1A). Oligonucleotide primers specific for upstream (5') and downstream (3') regions of the target nucleic acid hybridize to the template allowing for extension by DNA polymerase to amplify the target. If the DNA polymerase used is a strand displacing polymerase without exonuclease activity, complete thermal denaturation of the double stranded target nucleic acid is unnecessary, working in conjunction with duplex destabilizing agents to lower the required melting temperature. The temperature cycling process is repeated and results in exponential amplification of the specific nucleic acid target sequence (FIG. 1B). In OPCRar, double stranded target nucleic acid enters the melt stage where, depending on the temperatures, may result in either partial or complete denaturation of the duplex. Unwinding of the duplex begins at the ends of the target and single stranded nucleic acid is bound and stabilized by single stranded binding protein (circles). The reaction is cooled and enters the hybridization/polymerization stage where primers hybridize in a specific manner to the 5' ends of each strand of the target duplex. After primer hybridization, DNA polymerase (squares) binds to the template/primer duplex and extends the primer in the 5'.fwdarw.3' direction by incorporation of dNTPs, copying the template stand of DNA. If the polymerase used has strand displacement activity, it will be able to displace the opposing stand in the partially denatured complex. Upon generation of new duplex DNA, the thermal cycle is repeated many times to result in exponential amplification of the target nucleic acid sequence.

The OPCRar method is based upon, but not limited to, the combined use of nucleic acid destabilizing agents which lower the reaction melting temperature, and two oligonucleotide primers of unusually high melting temperature (Tm) to raise the annealing temperature during thermal cycling. For a given target nucleic acid, one oligonucleotide primer preferably hybridizes to the 5'-end of the sense strand containing the target sequence, and one primer preferably hybridizes to the 5'-end of the anti-sense strand containing the reverse-complementary target sequence. OPCRar preferably utilizes, but is not limited to, the use of a strand displacing DNA polymerase without exonuclease activity to further lower the melting or denaturation temperature necessary for efficient target nucleic acid amplification. OPCRar may amplify a target nucleic acid in the presence or absence of an accessory protein. Any specific OPCRar system may be optimized by addition, subtraction, or substitution of components within the mixture.

This amplification technology has improved characteristics over other amplification methodologies reported in prior art in the context of low-cost, rapid, point-of-care nucleic acid diagnostics. Unlike the above described nucleic acid amplification methodologies, the OPCRar system, enabled by its robust enzymatic process is robust, fast and tolerant to temperature fluctuations of a low cost heating device, thus ideally suited for low-cost, point-of-care applications. By minimizing the temperature differentials encountered during thermal cycling, OPCRar combines the speed and reliability of PCR with the lowered instrumentation requirements of isothermal amplification methodologies.

The OPCRar system's simplified thermal cycling requirement is ideally suited for passive-cooling instrumentation, where heat may be applied to one surface of a chamber and cooling occurs through heat dissipation to the atmosphere on the opposing surface. Such passive-cooling dramatically lowers the cost and complexity of any nucleic acids diagnostics device. Passive-cooling has been previously reported for use in diagnostics devices, however, these devices have employed conventional PCR cycling assay chemistry to amplify target nucleic acids limiting the rate of reaction (Luo et. al. Nuc Acids Res. 2005; Wilding et. al., Nuc. Acids. Res. 1996; Burke et. al., Science 1998;). Another advantage of OPCRar is that efficient nucleic acid amplification may occur over a wide range of melting and annealing temperatures and consequently requires less stringent temperature control mechanism. In the construction of miniaturized nucleic acid diagnostics, maintenance of uniform temperature throughout the entire reaction volume can be challenging, with a particularly high temperature gradient occurring between the heated and unheated sides of the reaction chamber. Such temperature variation may result in inefficient amplification using conventional PCR or isothermal reaction chemistries. OPCRar, through the use of the combination of robust polymerase, destabilizing reagent and other polymerase accessory factors, is designed to minimize problems associated with precise temperature regulation and maintenance; so long as the coolest regions of the reaction chamber observe the minimal possible melt temperature and the maximal possible annealing temperature for a given nucleic acid target the reaction will progress efficiently, even if other regions of the reaction volume vary by >10° C. Moreover, the robust OPCRar nature of amplification chemistry along with the minimal power/energy consumption enables rapid and efficient amplification reaction at much large volume (e.g. 20 μl instead sub μl in a typical μPCR chips) greatly relaxed the stringency of the up-front sample preparation/nucleic acid isolation process (in terms of obtain sub μl of input template that is both highly concentrated and ultra-pure nucleic acid free of any trace contaminant e.g. salt and ethanol carry over and inhibitory substance) and requirement of ultra-high concentration and ultra-pure of PCR enzymes and bioeagents.

Solvent Reagents

Solvents such as DMSO and formamide are known to lower the melting temperature of duplex nucleic acids by .about.0.5-0.7° C. for every 1% volume added. These reagents are often used to improve amplification efficiency of target nucleic acids containing high GC content and, thus, high Tm to facilitate complete denaturation of difficult-to-melt double stranded templates. Commonly, PCR thermal cycling temperatures are kept constant upon incorporation of duplex destabilizing agents into PCR reactions. In contrast, OPCRar preferably utilizes the addition of uniquely high concentrations of DMSO to dramatically lower the melting temperature of the thermal cycle. In conventional PCR, DMSO is rarely used above 10% v/v due to the loss of polymerase activity associated with high concentrations of these reagents in conjunction with the high temperatures (generally greater than 90° C.) of the melting stage. The OPCRar system and method, on the other hand, preferably uses DMSO concentrations between 10 and 15%. Unexpectedly, this amount of DMSO does not produce significant loss of polymerase activity.

Referring now to FIG. 2, amplification according to one embodiment of the present invention is compatible with a variety of DNA polymerases, depending on the conditions. Ribonucleic acid isolated from nasal aspirate containing Influenza A virus (0.3 ng/µL) was used as a nucleic acid template under multiple Reverse Transcription-OPCRar conditions using VentR polymerase. The OPCRar primers FP3 and RP4 were used to generate a product of 153 bp which was visualized by electrophoresis on a 12% polyacrylamide gel stained with ethidium bromide. All reactions contained Superscript III Reverse Transcriptase, where an initial cDNA generation stage was performed for 5 minutes at 55° C. prior to thermal cycling. Gel lanes are labeled with concentration of DMSO, and the melt and hybridization stage temperatures used; reactions were cycled 40 times.

Figure 3A:
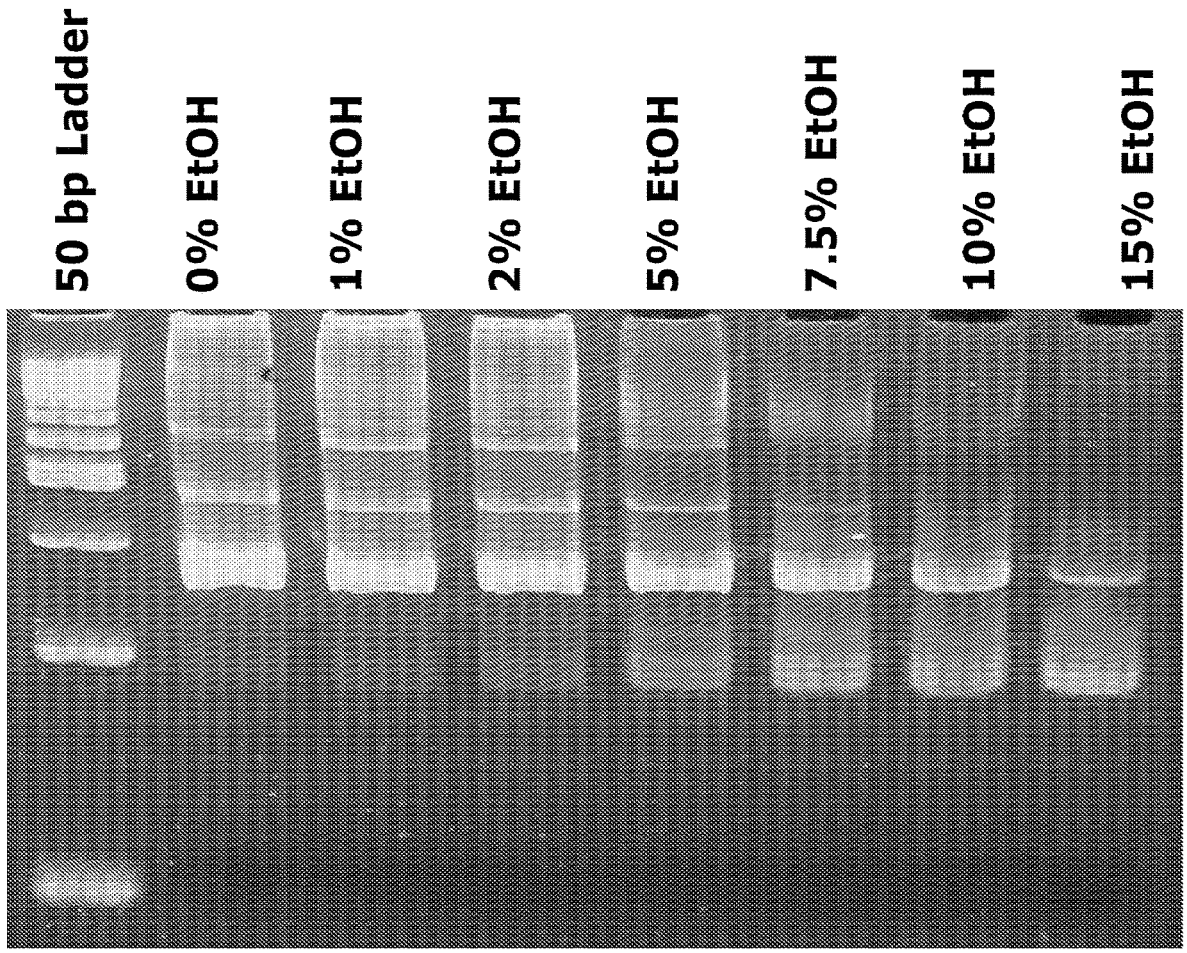
FIGS. 3A and 3B represent a series of photos of an acrylamide gels illustrating an effect of ethanol on nucleic acid amplification according to one embodiment of the present invention.
Figure 3B:
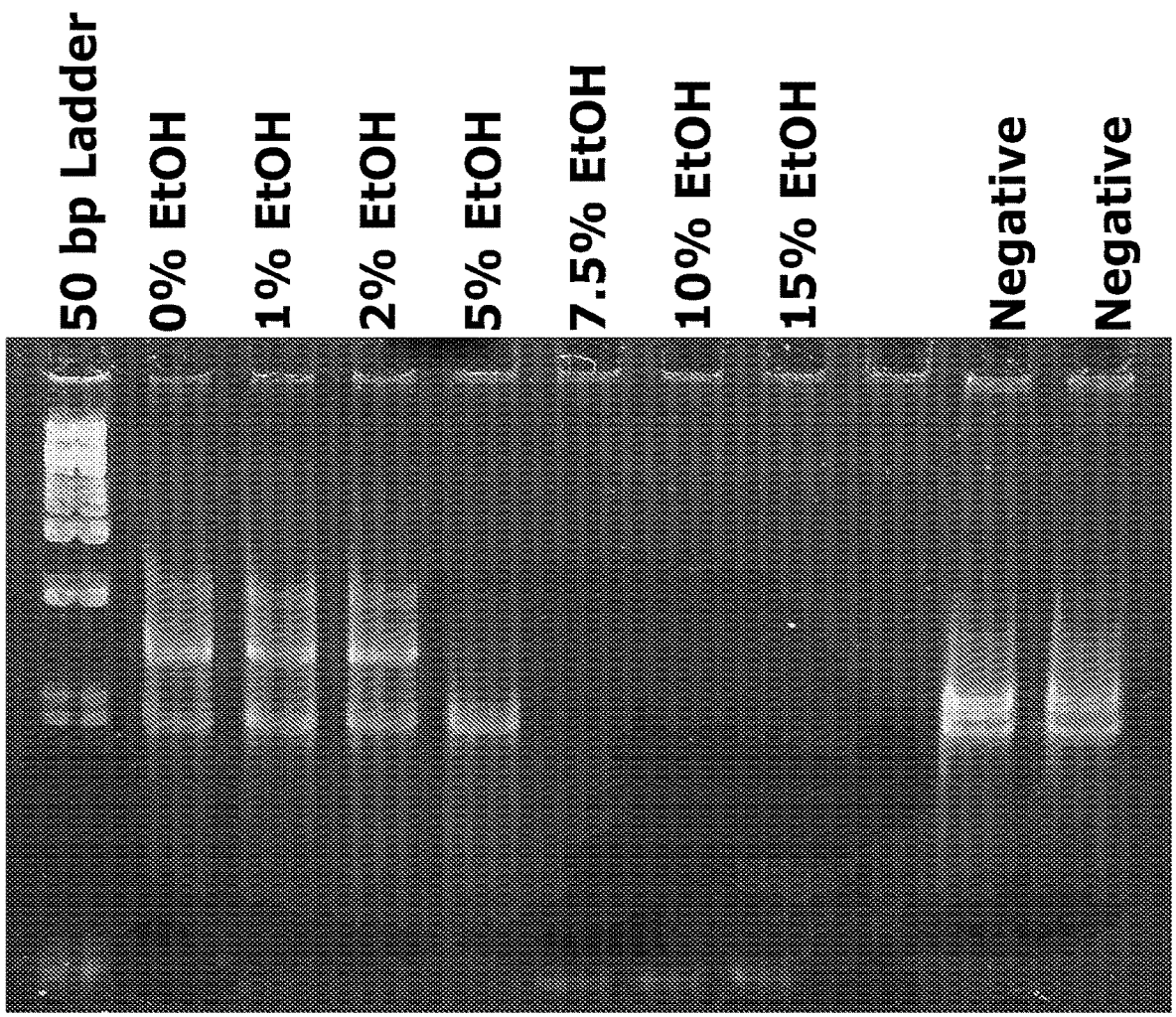

The conventional PCR enzyme, e.g. Taq DNA polymerase reaction mixture is extremely sensitive to any trace amount of alcohol, e.g. ethanol, whereas in one embodiment of the invention the novel reaction mixture is exceedingly resistant to inhibition by ethanol. Referring now to FIG. 3, ethanol effect on nucleic acid amplification according to one embodiment of the present invention is demonstrated. Total nucleic acid isolated from Candidatus. Liberibacter asiaticus-infected leaf tissue (3.4 ng/µL) was used as a starting template. Reactions were performed either under OPCRar conditions using VentR (exo-) DNA polymerase, Et SSB, and the primers hyvl_For and hyvl_Rev, in the presence of 15% DMSO (FIG. 3A), or conventional PCR conditions using Taq polymerase and the primers HLBas-P2 and HLBr-P1 (FIG. 3B). OPCRar solutions were heated at 85° C. for 2 minutes to denature the template and then cycled 40 times, oscillating between 76° C. for 10 seconds, and 60° C. for 10 seconds to generate a product of 139 bp. Conventional PCR reactions were heated to 95° C. for 2 minutes and then cycled 40 times, varying between 95° C. for 10 seconds and 58° C. for 40 seconds to generate a product of 130 bp. The amplified products were visualized on a 12% acrylamide gel, stained with ethidium bromide. Ethanol concentrations included in the amplification reaction mixture are shown. It is evident that the OPCRar formulation (FIG. 3A) is dramatically more resistant to inactivation by ethanol as compared to conventional PCR (FIG. 3B).

Use of VentR(exo-) DNA polymerase and Et SSB under typical OPCRar conditions results in no loss of activity in up to 10% ethanol. This is a significant yet surprising discovery regarding the application of OPCRar to low cost point-of-care devices. Since the conventional wisdom of PCR and isothermal amplification typically advise users to provide the highly purified nucleic acid input that is free of alcohol and salt. As the result, almost all the researchers are employing some kind of vacuum dry, air dry, spin down or heating steps between the alcohol-based washes and eluting the target nucleic acid from nucleic acid-affinity microbeads, glass frit, matrix or filter etc before they run the sample through the PCR amplification process. For instance of an integrated point of care diagnostic device, in addition to amplification and detection of nucleic acids, the devices must also rapidly isolate target nucleic acids. Generally this is performed by binding nucleic acid to a glass fiber matrix and washing in the presence of significant concentrations of salt and ethanol, subsequently eluting in buffer containing minimal salt and no ethanol. Before elution, wash buffer retained on the binding matrix is removed to prevent carry-over to the elution volume; in commercial nucleic acid isolation kits this is typically performed by centrifugation. The specific enzyme mixture of OPCRar eliminates this need for careful removal of ethanol during nucleic acid isolation, making this embodiment of the invention tailored for low cost integrated diagnostics that does not require a vacuum, centrifuge, air dry or heating dry component.

Primers

Oligonucleotide primers as described here can be synthesized and purified by methods known in the art. (See, for example U.S. Pat. No. 6,214,587). In present embodiments, two sequence-specific primers, representing a primer pair are used to exponentially amplify a target nucleic acid sequence. The first primer hybridizes to the upstream 5' region of the target nucleic acid, and the second primer hybridizes to the downstream, 3' region of the target sequence. The primers hybridize to the 5' end of one strand present in the target duplex, and the primers are extended by a polymerase in a 5' to 3' direction using the target nucleotide sequence as a template (FIG. 1B). Conditions of hybridization are standard as described in "Molecular Cloning and Laboratory Manual", 2nd ed. Sambrook, Rich and Maniatis, pub. Cold Spring Harbor (2003). To achieve specific amplification of a given target sequence a homologous primer is preferred, where every nucleotide in the primer is complementary to the target sequence. Primers may, however, include bases that are non-homologous with respect to the template nucleic acid, or 5' sequences which are non complementary to the target nucleotide sequence(s). Multiple pairs of primers can be used in a single OPCRar experiment in order to amplify multiple nucleic acid targets simultaneously in the same reaction mixture. So-called multiplexing is a commonly used technique in single nucleotide polymorphism analysis, in detection of pathogens, and for incorporation of internal controls into an individual reaction. Higher level of multiplexing may also be achieved through a use of 5' universal tag sequence introduced to each target-specific 3'-region that allows the universal amplification of all the target sequences with different internal pathogen sequences.

Oligonucleotide primer design involves several parameters such as melting temperature and intra- and inter-primer sequence alignment. Melting temperature is governed by factors such as the primer length and GC content. Inter-primer sequence complements can result in hairpin structures, which can impede efficient amplification, whereas intra-primer homology can result in unwanted amplification products dubbed primer-dimers. When designing a primer, it is important to select a sequence within the target which is specific to the nucleic acid molecule to be amplified and will minimally interact with either itself or other primers present in the amplification reaction.

In most nucleic acid amplification strategies, the melting temperature of a primer is preferably about 10 to 30° C. higher than the temperature at which the hybridization and amplification takes place. With the temperature of the annealing/polymerization stage(s) being 55-60° C. in a PCR reaction, primers are typically 18-30 base pairs in length. This specific oligonucleotide length is minimized to allow for easy primer binding without loss of sequence specificity. In the OPCRar system, however, primers are preferably designed to be unusually long at 35-55 base pairs, with a melting temperature preferably between 70-80° C. in order to raise the temperature of the annealing stage. Considering the levels of the duplex destabilizing agent, DMSO, used in a typical OPCRar reaction (.about.10-15%), the calculated Tm of OPCRar primers is preferably only <10° C. above the annealing temperature used during thermal cycling. In experiments and with the extreme length of OPCRar primers, efficient amplification occurs despite a minimal difference in primer Tm (compensating for the concentration of DMSO) and the annealing/elongation temperature.

Figure 4:
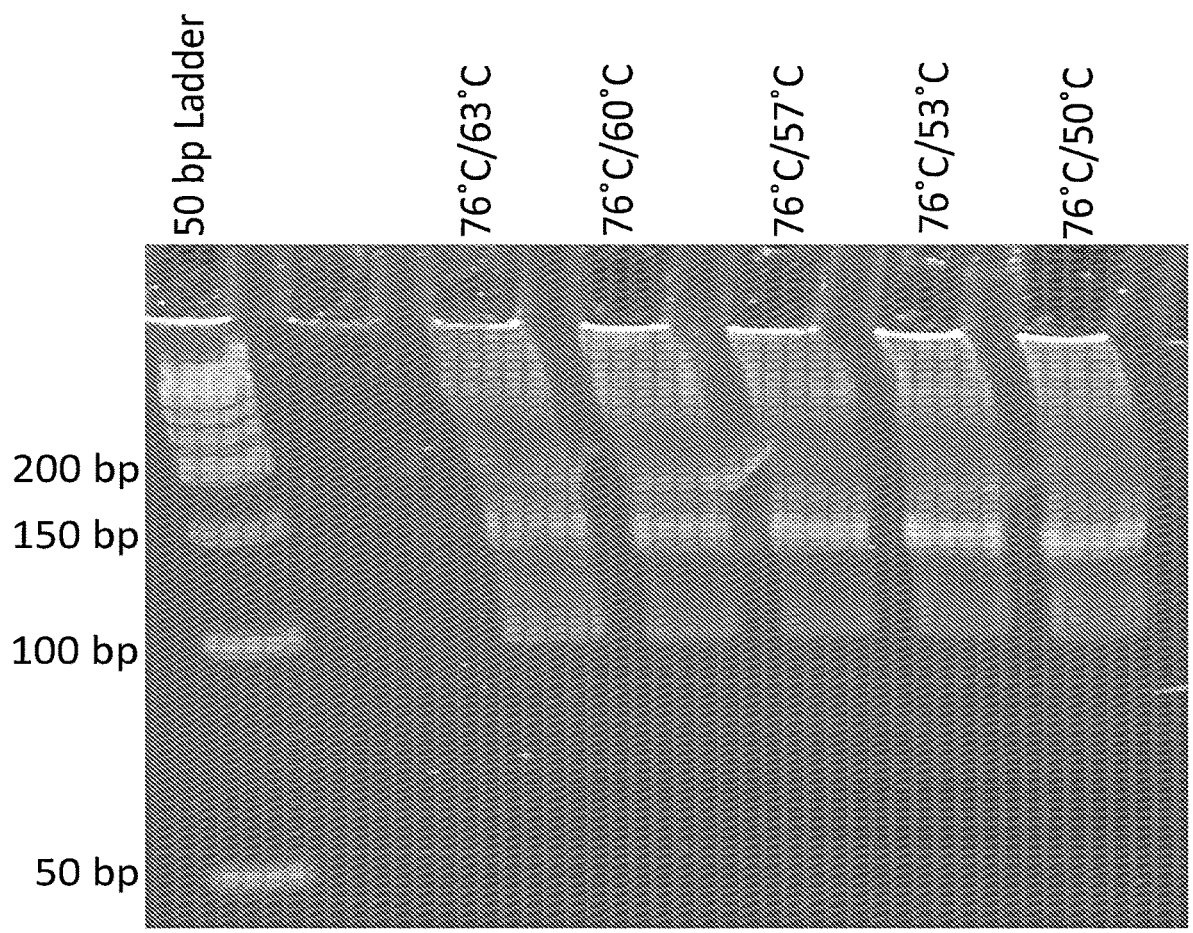
FIG. 4. is a photo of an acrylamide gel illustrating differences in temperature of annealing and primer melting temperature to support efficient amplification according to one embodiment of the present invention.

Referring now to FIG. 4, OPCRar primers require minimal difference between annealing stage temperature and primer Tm to support efficient amplification according to one embodiment of the present invention. A plasmid containing the hyvl gene sequence (12 ng/L) was amplified using the primers hyvl_For and hyvl_Rev to generate a product of 139 bp, which was visualized by electrophoresis on a 12% acrylamide gel stained with ethidium bromide. Following an initial 2 minute 85° C. melt step, all reactions were cycled 40 times, 10 seconds at each of the indicated melt and hybridization temperatures. The calculated Tm for primers hyvl_For and hyvl_Rev are 72.2° C. and 70.9° C., respectively. The reaction was performed in 10% DMSO, lowering the effective Tm by 7° C., assuming a reduction of 0.7° C. per 1% volume. Even with a negligible difference between primer Tm and hybridization temperature, the amplification reaction is observed to proceed as efficiently as if the temperature difference is much lower.

Figure 5:
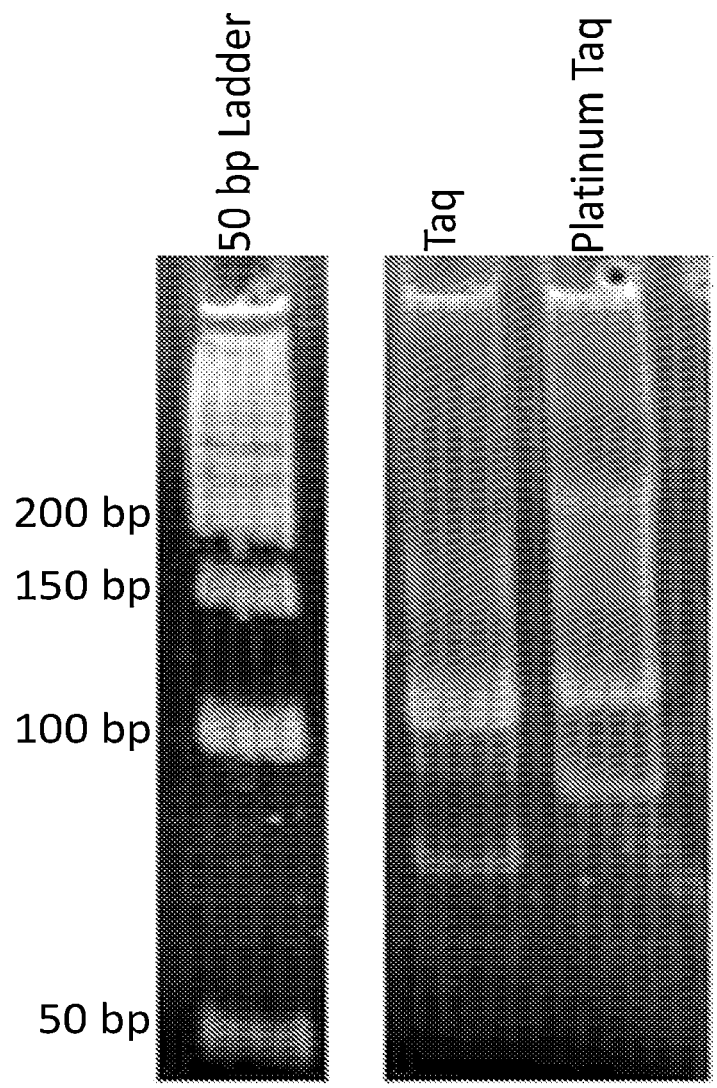
FIG. 5. is a photo of an acrylamide gel illustrating an effect of hot-start DNA polymerase on primer dimer formation according to one embodiment of the present invention.

Referring now to FIG. 5, the effect of hot-start DNA polymerase on primer dimer formation using OPCRar. Control reactions containing no nucleic acid template were performed with Superscript III RT, and either Taq or Platinum Taq DNA polymerase in the presence of primer pair FP3 and RP4 (8 UM each) and 15% DMSO. The cycling parameters were 55° C. for 5 minutes, 85° C. for 2 minutes, and 40 cycles of 80° C. for 15 seconds and 65° C. for 15 seconds. After electrophoresis on a 12% acrylamide gel, OPCRar products were visualized by staining with ethidium bromide. Platinum Taq is a commercially available hot-start enzyme (Invitrogen, Carlsbad, Calif.) that is conjugated to an antibody which dissociates upon heating the reaction solution to 94° C. under normal PCR conditions. In the presence of template nucleic acid, this primer pair will produce a product of 153 bp. It is clear that this hot-start preparation is no better than conventional Taq in reducing the formation of <110 bp primer dimers during OPCRar. One complication of long primers used in the OPCRar reaction is that they are more prone to result in non-specific and unwanted amplification products known as primer dimers. Primer dimers are formed when the 3' ends of primer oligonucleotides transiently bind one another during the initial increase of temperature at the start of an amplification reaction. During this critical time period, DNA polymerase may extend these transient complexes resulting in products that compete with specific target amplification during thermal cycling, particularly if the starting template nucleic acid concentration is very low. A commonly employed technique to reduce primer dimer formation during PCR is to utilize so-called 'hot-start' DNA polymerases. These commercially available enzymes are non-covalently bound to an inhibitory molecule such as an antibody. When the reaction temperature increases above 90° C., the inhibitory molecule dissociates freeing the polymerase to perform normally. However, surprisingly, in our hands the hot-start enzyme Platinum Taq DNA Polymerase (Invitrogen, Carlsbad, Calif.) failed to appreciably reduce the abundance of primer dimer amplification, indicating that this commonly used methodology is insufficient for OPCRar, indicating that OPCRar process is a much more efficient amplification process than traditional PCR that enables dimers formation originated from transient kinetic collisions of homo and hetero-dimers that don't typically occur in the conventional PCR process.

Figure 6:
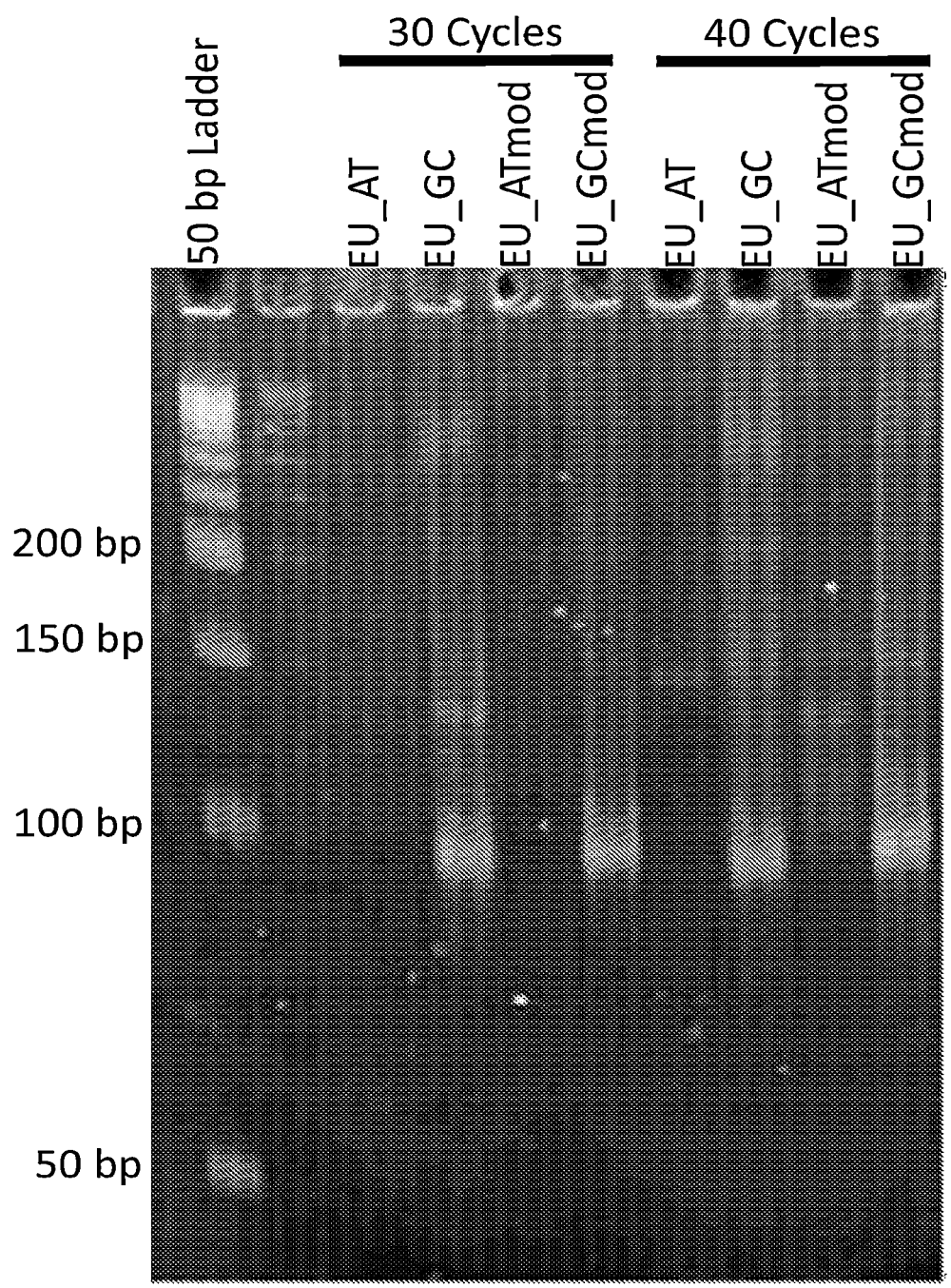
FIG. 6. is a photo of an acrylamide gel illustrating an effect of GC and AT clamps on primer-dimer formation according to one embodiment of the present invention.

Referring now to FIG. 6, a gel illustrating the effect of GC and AT clamps on primer dimer formation during OPCRar according to one embodiment of the present invention is presented. Primers designed to amplify the elongation factor gene of C. Liberibacter *asiaticus* were used in the absence of a starting template (3.5 ng/μL) to determine the propensity for primer dimer formation. In the presence of template the product sizes for the various primer sets would range from between 140-155 bp. Primer sequences can be seen to the right, with the AT or GC clamps in gray. For 'mod' primer sets, each primer contains a non-homologous base with respect to the template (underline), that increases homology with the second primer. All reactions were performed using VentR(exo-) DNA polymerase, Et SSB, in the presence of 15% DMSO. Solutions were heated at 85° C. for 2 minutes to denature the template and then cycled either 30 or 40 times, oscillating between 80° C. for 15 seconds, and 65° C. for 15 seconds. The amplified products were visualized on a 12% acrylamide gel, stained with ethidium bromide. As is clearly observed, GC clamp primer sets result in significant primer dimer formation while AT clamp primers result in no primer dimer formation.

In order to minimize the potential for primer dimer formation, OPCRar primers may be designed to employ several strategies differing from those used to generate conventional PCR primers. First, PCR primers generally possess a GC rich 3' end called a 'GC clamp', which results in greater specific binding to the target sequence. In OPCRar primers, however, it has been observed that a high GC content in the 3' region of the primer results in greater primer dimer formation, thus, OPCRar primers are made to contain AT rich 3' regions to energetically reduce the affinity of 31-3' primer interactions resulting in these unwanted amplification products (FIG. 6). A second strategy for OPCRar primer design is to design primers that contain complementary 5' or internal sequences of at least 5 consecutive nucleotides. Oligonucleotides designed in this way will steer any primer hybridization during the initial increase in reaction temperature towards duplex structures that are not competent for polymerase extension. If suitable complementary sequences cannot be found within the target nucleic acid sequence, non-homologous, or mutated, bases can be used to generate them within the OPCRar primers. The exceptional length of OPCRar primers overcomes minor mispairing between primer and target during the early cycles of an amplification reaction. Primer sets are

```
EU AT
Forward
                                          (SEQ ID NO 21)
GTTCTTGTAG CGTTGCAGTC TTCTGCGGAA GATAAGGAAT TGCTTT Reverse
                                          (SEQ ID NO 22)
GGGCACGTTT ATTAGCAACA ATAGAAGGAT CAAGCATCTG

CACAGAAAT
```

EU GC
Forward (SEQ ID NO 23)
CTTGTAGCGT TGCAGTCTTC TGCGGAAGAT AAGGAATTGC

TTTCTGCG

Reverse (SEQ ID NO 24)
CACGTTTATT AGCAACAATA GAAGGATCAA GCATCTGCAC

AGAAATCACCG

EU-Atmod
Forward (SEQ ID NO 25)
GGTGTTCTTG TATCGTTGCA GTCTTCTGCG GAAGATAAGG

AATTGCTTT

Reverse (SEQ ID NO 26)
GTAATGGGCA CGTTTATTAG CAACGATAGA AGGATCAAGC

AACTGCACAG AAAT

EU GCmod
Forward (SEQ ID NO 27)
CTTGTATCGT TGCAGTCTTC TGCGGAAGAT AAGGAATTGC

TTTCTGCG

Reverse (SEQ ID NO 28)
GGCACGTTTA TTAGCAACGA TAGAAGGATC AAGCATCTGC

ACAGAAATCA CCG

OPCRar primers may include any of the deoxyribonucleotide bases adenine "A", thymine "T", guanine "G" or cytosine "C" and/or one or more ribonucleotide bases, A, C, uraceil "U", G. Furthermore, OPCRar primers may contain one or more modified deoxyribonucleotide or ribonucleotide bases where the modification does not prevent primer hybridization to the target nucleic acid, primer elongation by polymerase, or denaturation of duplex nucleic acid. OPCRar primers may be modified with chemical groups such as methylphosphonates or phosphorothioates, with non-nucleotide linkers, with biotin, or with fluorescent labels such as the amine-reactive fluorescein ester of carboxyfluorescein. Such modifications may enhance primer performance or facilitate the detection and characterization of amplification products.

Polymerases

After single stranded template nucleic acid region has hybridized with a primer during OPCRar, a polymerization step occurs. If the target nucleic acid is DNA, a DNA polymerase is selected which acts on the target to extend the hybridized primers along the nucleic acid template in the presence of the four dNTP nucleotide bases to form a double stranded product where the newly synthesized strand is complementary to the nucleotide sequence of the template (FIG. 1). If the initial target is RNA, a reverse transcriptase is first used to copy the RNA template into a cDNA molecule, which is further amplified during OPCRar by a DNA polymerase.

A variety of DNA polymerases may be selected for OPCRar on the basis of thermostability and processivity, especially in the presence of the destabilizing agent, and alcohol (FIG. 2). Although not required, polymerases displaying strand displacement activity and lacking an exonuclease activity are found to significantly improve OPCRar reactions (FIG. 2). Examples of suitable DNA polymerases include Taq polymerase, KlenTaq DNA polymerase (AB Peptides, (St Louis, Mo.)), Bst DNA polymerase Large fragment (New England Biolabs, Beverly, Mass.), VentR or VentR (exo-) (New England BioLabs), DeepVentR or DeepVentR (exo-) (New England BioLabs), and similar enzymes. Suitable thermostable reverse transcriptases include Superscript II (Invitrogen, Carlsbad, Calif.), Superscript III (Invitrogen), and similar enzymes. It should be noted that the published conventional PCR amplification polymerase mixture fail to perform OPCRar due to the unique robustness requirement of OPCRar amplification. All the selected polymerase and bioreagent components should be carefully evaluated and experimentally tested before use.

Single-Stranded Binding Proteins

Figure 7:
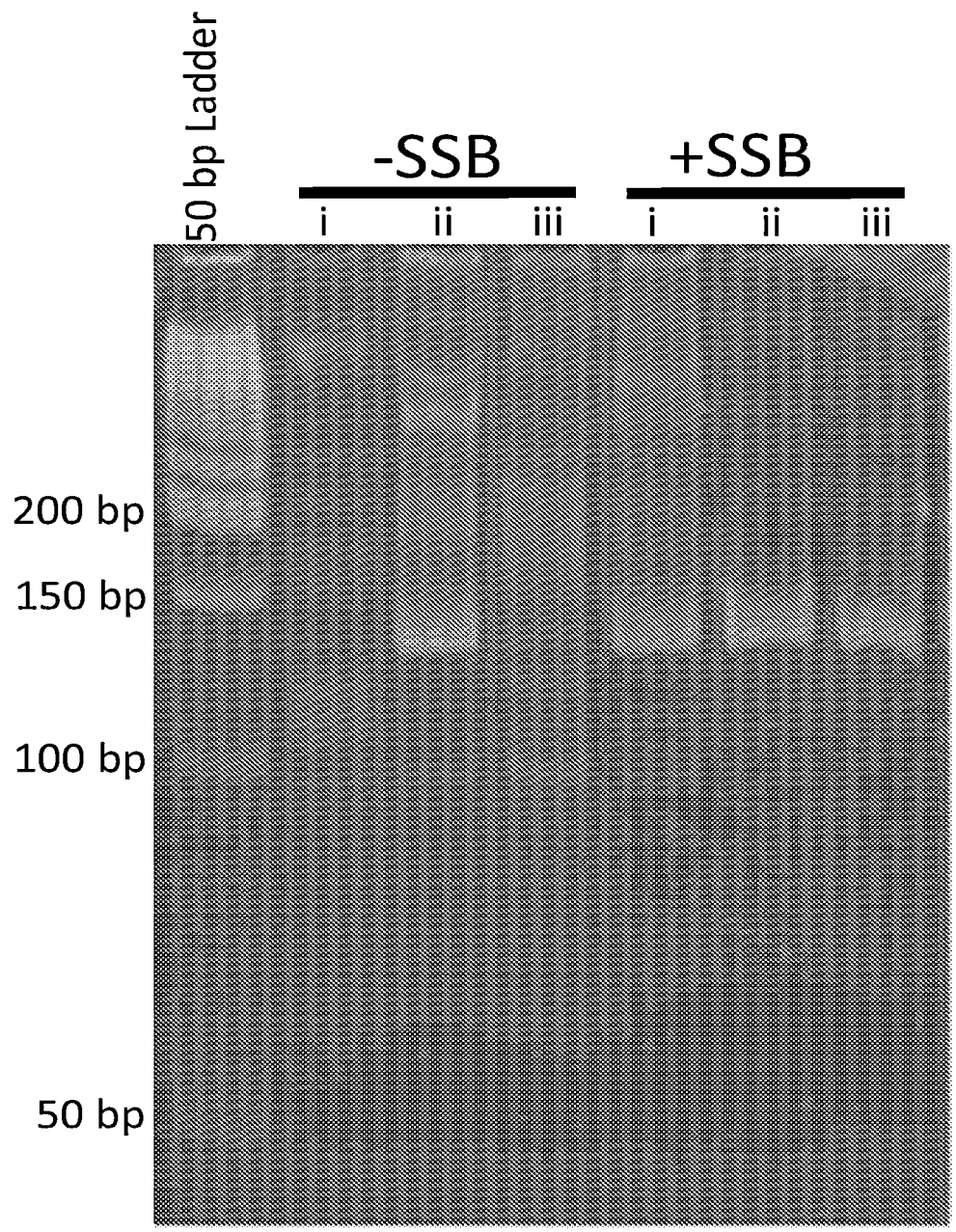
FIG. 7. is a photo of an acrylamide gel illustrating an effect of single stranded binding protein on product formation according to one embodiment of the present invention.

The OPCRar system preferably minimizes the temperature differential between melting and annealing thermal cycling stages, where this temperature differential is lowest if complete denaturation of duplex nucleic acid is unnecessary. While a strand-displacing DNA polymerase is helpful in this regard, accessory proteins may be used to further lower the thermal requirements for efficient amplification. Single-stranded binding proteins (SSBs) are known to stabilize single stranded nucleic acid to prevent the annealing of double stranded duplex formation, and have been shown to increase the efficiency of nucleic acid amplification reactions. The addition of a thermostable SSB to OPCRar methods according to an embodiment of the present invention is found to result in improved activity (FIG. 7). As an example, Et SSB (BioHelix Corporation, Beverly, Mass.), although the choice of SSB is not limited to a specific protein and may include SSBs isolated and cloned from a thermophilic organism, or engineered from a non-thermostable precursor SSB.

Referring now to FIG. 7, a gel showing the effect of single stranded binding protein on OPCRar product formation according to one embodiment of the present invention is illustrated. A Universal Influenza A single stranded DNA template (1E6 copies/µL, Biosearch Technologies, Inc., Novato, Calif.) was amplified using the OPCRar primers FP3 and RP3 to generate a product of 133 bp, which was visualized by electrophoresis on a 12% acrylamide gel stained with ethidium bromide. OPCRar according to one embodiment of the present invention was performed in the presence or absence of thermostable SSB under the following conditions: i) 15% DMSO; ii) 15% DMSO, 5% Glycerol; iii) 15% DMSO, 0.25 M Betaine. The cycling parameters used for all reactions were 75° C. for 15 sec and 65° C. for 15 sec, repeated 45 times.

Figure 8A:
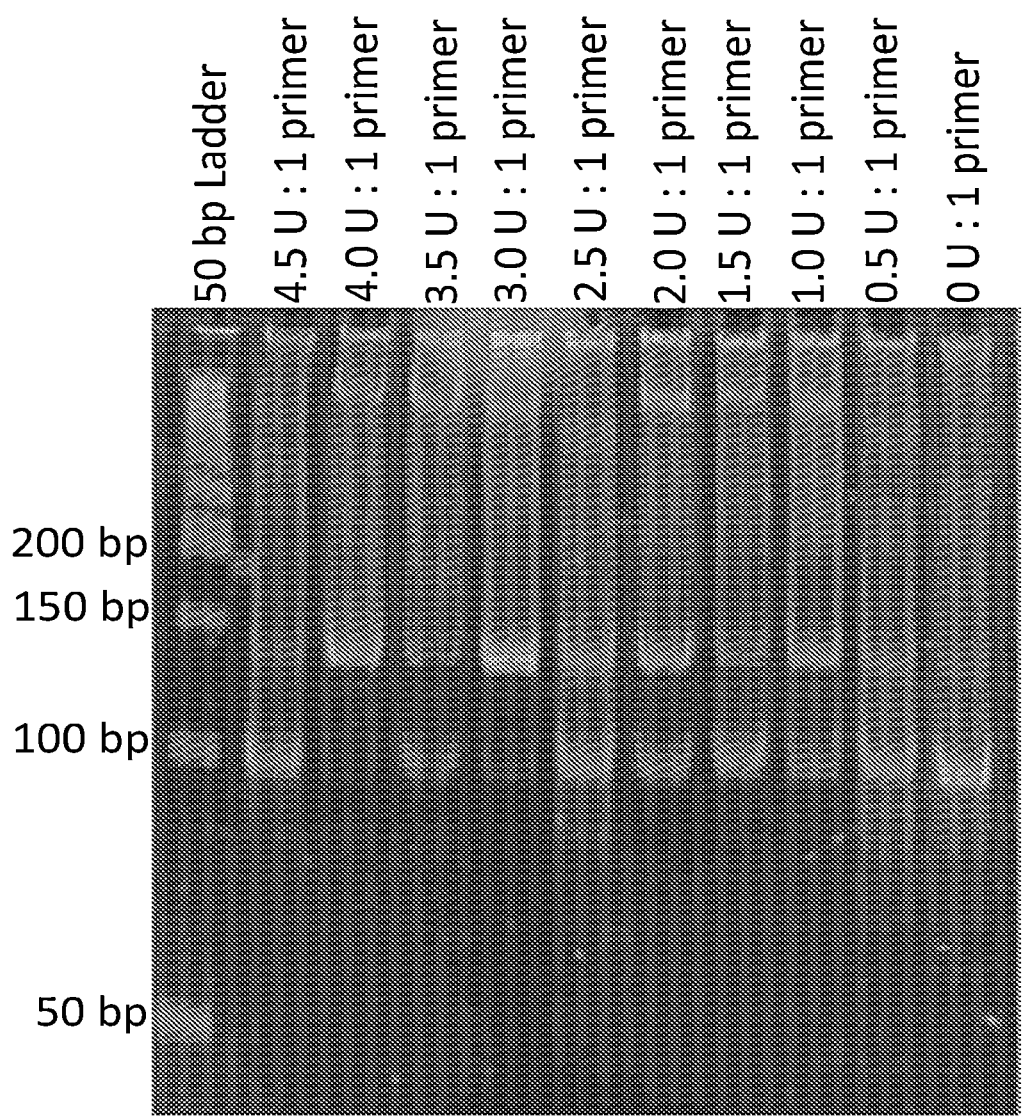
FIGS. 8A and 8B represent photos of acrylamide gels illustrating a reduction in the amount of primer-dimer formation by T4 gene protein 32 according to one embodiment of the present invention.
Figure 8B:
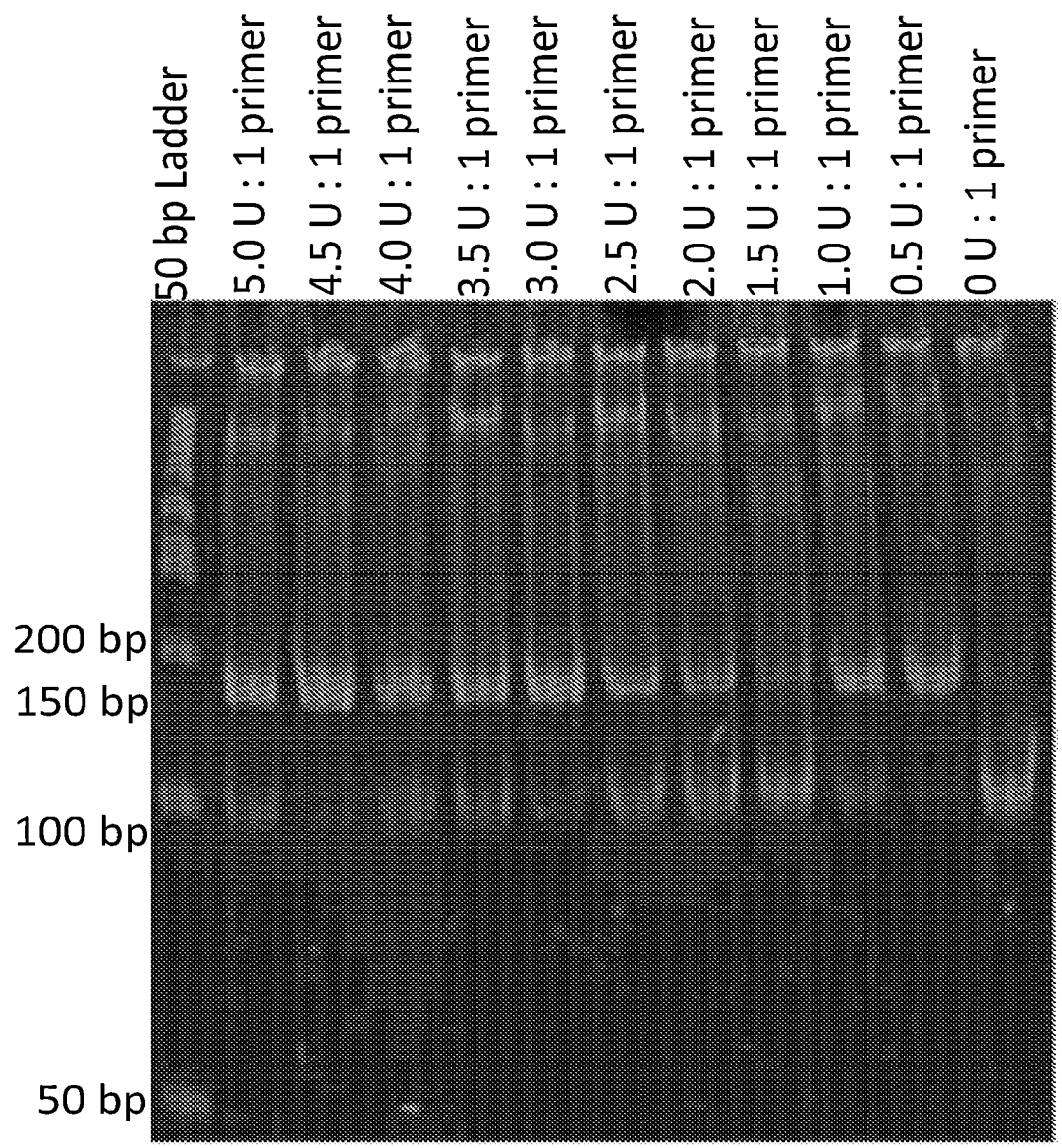

In addition to thermostable SSBs that aid OPCRar, non-thermostable SSBs such as T4 bacteriophage SSB (New England BioLabs) may be used to reduce primer dimer formation in the initial heating of the OPCRar solution (FIG. 8). By preincubating OPCRar primers in the presence of a molar excess of T4 gene 32 protein and then adding them to the reaction mixture, it has been observed that the unwanted amplification of primer dimers is minimized during OPCRar. These SSBs presumably bind to the single stranded oligonucleotide primers, reducing the potential for 3'-3' pairing and, thus, primer dimer formation. Upon heating the solution above 65° C., the T4 SSB is denatured and releases the primers for normal reactivity during thermal cycling. Referring now to FIG. 8, a gel illustrates the reduction in the amount of primer-dimer formed during one embodiment of the present invention with pre-incubation of primers with T4 gene 32 protein. Before addition to the reaction mixture, OPCRar primers were incubated with the indicated stoichiometric excess of active units of T4 gene 32 protein (T4 SSB) at 25° C. for 5 minutes in the presence of 1.times. ThermoPol buffer (New England BioLabs, Beverly, Mass.). A synthetic Universal Flu A DNA template (1E6 copies/µL, Biosearch Technologies, Inc.) was amplified using primers FP3 and RP3 to generate a product sequence of 133 bp. The reactions were held at 85° C. for 2 minutes followed by 50 cycles of 75° C. for 15 sec and 65° C. for 15 seconds. Reaction products were visualized by electrophoresis on a 12% acrylamide gel stained with ethidium bromide. The experiment described in FIG. 7 was repeated on a different day by a different researcher to assess the reproducibility of the data and shown in FIG. 8. It can be clearly observed that the pre-incubation of primers with T4 SSB both increases the amount of amplified product and decreases the intensity of the primer-dimer band (.about.100 bp), relative to no pre-incubation (right-most lanes).

The OPCRar method is particularly well suited for use with a device such as that described in the commonly owned provisional patent application filed on the same date hereof, entitled "INTEGRATED DEVICE FOR NUCLEIC ACID DETECTION AND IDENTIFICATION". The configuration of certain embodiments of that device enables the temperature of a solution to rapidly cycle while the solution remains in the same chamber, preferably without active cooling. For example, the temperature could increase or decrease sufficiently to perform OPCRar in less than or equal to 20 seconds, or more preferably less than or equal to 15 seconds, or more preferably less than or equal to about 8 seconds, or more preferably less than or equal to about 4 seconds. Thus and OPCRar temperature cycle could be performed in as little as, or even faster than, 8 seconds.

EXAMPLE 1

Method of Amplification of a DNA Target Duplex by OPCRar

To demonstrate that OPCRar is capable of amplifying a specific target sequence present in a double stranded DNA analyte, we used two OPCRar primers, primer HLB (Huang Long Bing) ForSh and primer HLBRevSh, to generate a 140 bp sequence from a PCR-amplified fragment of the C. Liberibacter asiaticus elongation factor gene by the OPCRar system. OPCRar Buffer (10.times.) was premade and contained 400 mM Tris-HCl (pH 8.4), 10 mM ammonium sulfate, 100 mM potassium chloride, and 0.25% Triton X-100. A 20 µL OPCRar solution was set up by mixing:
  8.4 µL water
  2.0 µL 10.times. OPCRar Buffer
  3.0 µL DMSO
  0.4 µL potassium chloride (2 M)
  0.5 µL magnesium chloride (100 mM)
  0.5 µl dithiothreitol (100 mM)
  0.5 µl dNTPs (10 mM)
  2.0 µL Primer set HLBForSh and HLBRevSh (4 M each)
  0.5 µL VentR (exo-) DNA Polymerase (2 U/µL)
  0.2 µL Et SSB, Extreme Thermostable Single Stranded Binding Protein (500 µg/mL)
  2.0 µL of PCR product dilution (0.6 to 0.0006 ng/µL starting concentration)

The reaction was heated at 85° C. for 2 minutes to denature the template and then cycled 40 times, oscillating between 80° C. for 5 seconds, and 65° C. for 5 seconds. After the reactions were complete, 5 µL of OPCRar product was mixed with 2 µl of 6.times. Sample Loading Buffer (New England BioLabs) and 1 µL of formamide, run on a 12% acrylamide gel, and visualized with ethidium bromide. A 140 bp product was clearly observed at all dilutions shown, and matches the predicted length of the OPCRar target sequence (FIG. 9).

Figure 9:
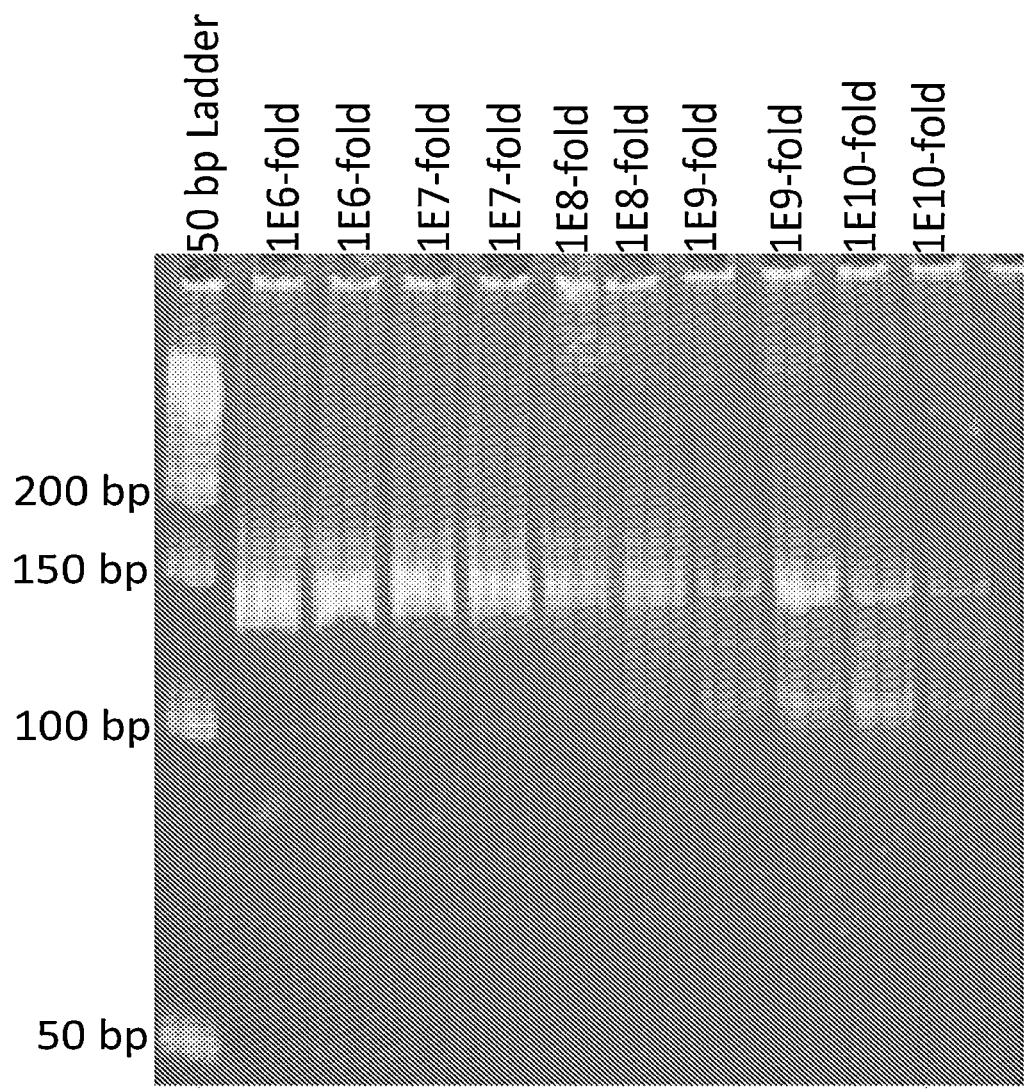
FIG. 9. is a photo of an acrylamide gel illustrating a specific target sequence present in double stranded DNA amplified according to one embodiment of the present invention.

Referring now to FIG. 9, amplification of a specific target sequence present in a double stranded DNA according to one embodiment of the present invention is shown in a gel. Serial dilutions of a PCR-amplified fragment of the C. Liberibacter asiaticus elongation factor gene (0.6 to 0.0006 ng/µL) were used as the starting template. The reaction was carried out using VentR(exo-) DNA polymerase, Et SSB, and the primers HLBForSh and HLBRevSh to generate a 140 bp sequence in the presence of 15% DMSO. The reactions were heated at 85° C. for 2 minutes to denature the template and then cycled 40 times, oscillating between 80° C. for 5 seconds, and 65° C. for 5 seconds. The OPCRar products were visualized on a 12% acrylamide gel, stained with ethidium bromide. A 140 bp product matching the predicted length of the target sequence was clearly observed at all dilutions shown.

EXAMPLE 2

Method of Amplification of a Single Stranded DNA Target by OPCRar

To demonstrate that OPCRar is capable of amplifying a specific target sequence from a single stranded DNA template, we used OPCRar primers FP3 and RP4 to generate a 153 bp sequence from a commercially available Universal Influenza A template (Biosearch Technologies, Inc.) by the OPCRar system. 10.times.OPCRar Buffer contains 400 mM Tris-HCl (pH 8.4), 10 mM ammonium sulfate, 100 mM potassium chloride, and 0.25% Triton X-100. A 20 µL OPCRar solution was set up by mixing:
  8.4 µl water
  2.0 µL 10.times. OPCRar Buffer
  3.0 µL DMSO
  0.4 µL potassium chloride (2 M)
  0.5 µL magnesium chloride (100 mM)
  0.5 µl dithiothreitol (100 mM)
  0.5 µL dNTPs (10 mM)
  2.0 µl Primer set FP3 and RP4 (8 µM each)
  0.5 µl VentR (exo-) DNA Polymerase (2 U/µL)
  0.2 µL Et SSB, Extreme Thermostable Single Stranded Binding Protein (500 µg/mL)
  2.0 µL of single stranded DNA template (1E9 to 1E2 copies/µL).

As a comparison of sensitivity, a real time PCR reaction was run using identical template concentrations as that used for the above OPCRars. 10.times. ThermoPol (New England BioLabs) contains 200 mM Tris-HCl (pH 8.8), 100 mM ammonium sulfate, 100 mM potassium chloride, 20 mM magnesium sulfate, and 1% Triton X-100. A 15 µL RT-PCR solution was set up by combining:
  9.7 µl water
  1.5 µL 10.times. ThermoPol Buffer
  0.4 µL dNTPs (10 mM)
  1.5 µL Primer set UniAfCDC/UniArCDC (4 µM each) including Taqman probe UniApCDC (1 µM)
  0.4 µl Taq Polymerase (5 U/µL)
  1.5 µl single stranded DNA template (1E9 to 1E2 copies/µL)

A serial dilution of universal Influenza A single stranded DNA template between 1E9 to 1E2 copies/µL was amplified by OPCRar in the presence of 15% DMSO, and real time PCR using a TaqMan probe. OPCRar reactions were first heated to 85° C. for 2 minutes, then cycled between 80° C. for 15 sec and 65° C. for 15 sec, repeated 40 times. RT-PCR reactions were heated to 95° C. for 2 minutes, then cycled 45 times between 95° C. for 10 sec and 58° C. for 40 sec. After the reactions were complete, 5 µl of OPCRar product was mixed with 2 µl of 6.times. Sample Loading Buffer (New England BioLabs) and 1 µL of formamide, run on a 12% acrylamide gel, and visualized with ethidium bromide. A 153 bp product was clearly observed for all samples (FIG. 10), and matches the predicted length of the OPCRar target sequence.

Figure 10:
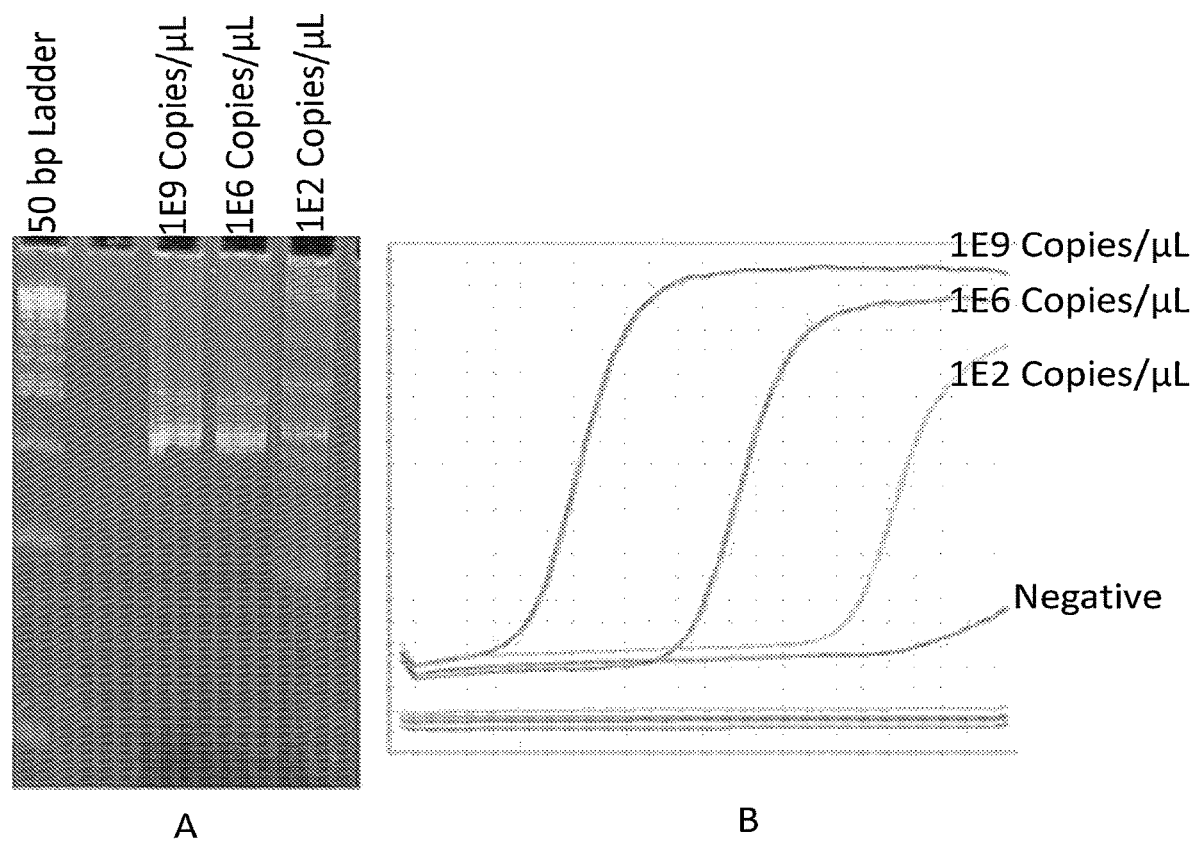
FIG. 10. is a photo of an acrylamide gel illustrating amplification of a specific target sequence present in ssDNA according to one embodiment of the present invention.
Figure 11:
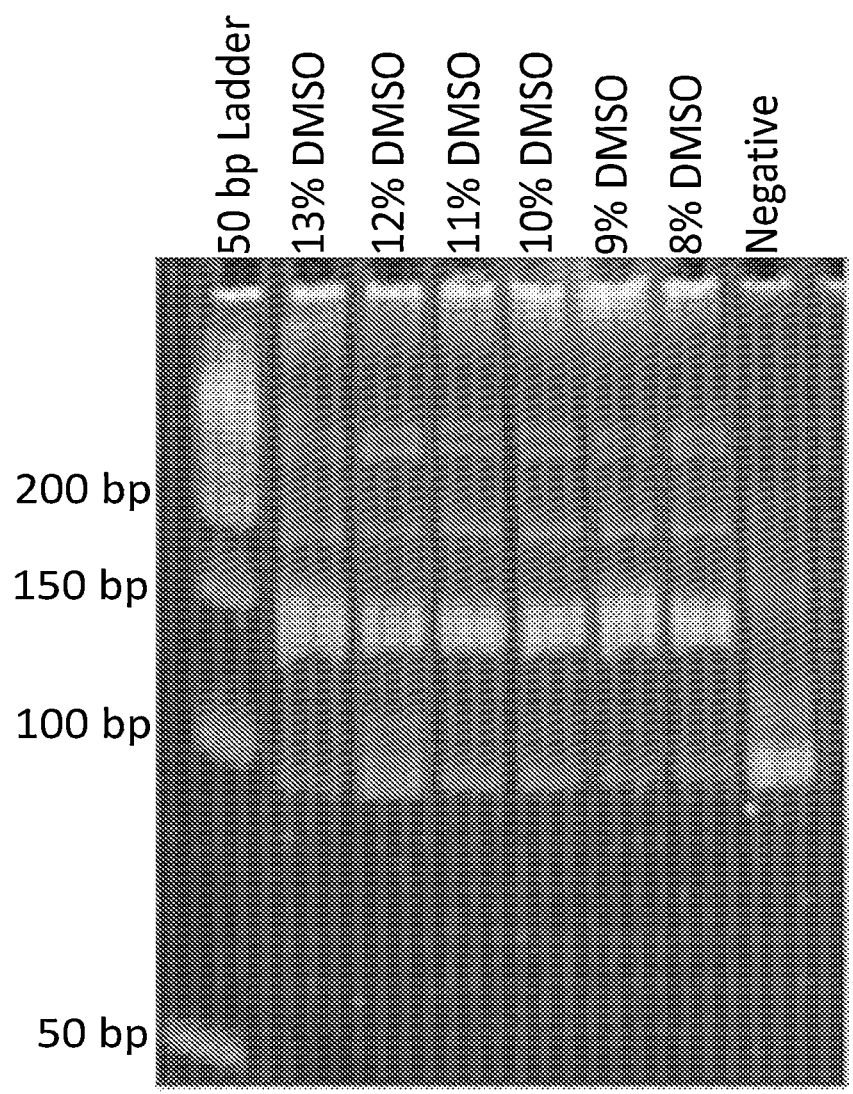
FIG. 11. is a photo of an acrylamide gel illustrating amplification of a specific target sequence present in plasmid DNA according to one embodiment of the present invention.
Figure 12:
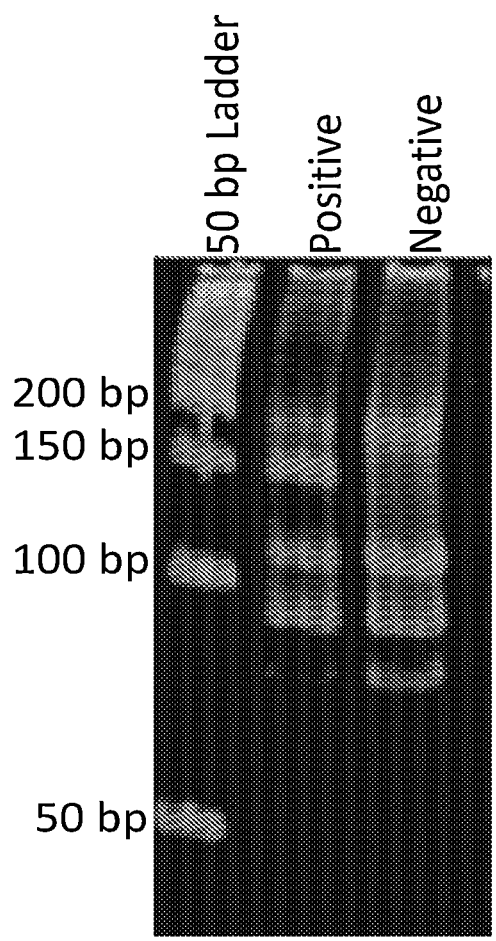
FIG. 12. is a photo of an acrylamide gel illustrating amplification of a single stranded RNA according to one embodiment of the present invention.
Figure 13:
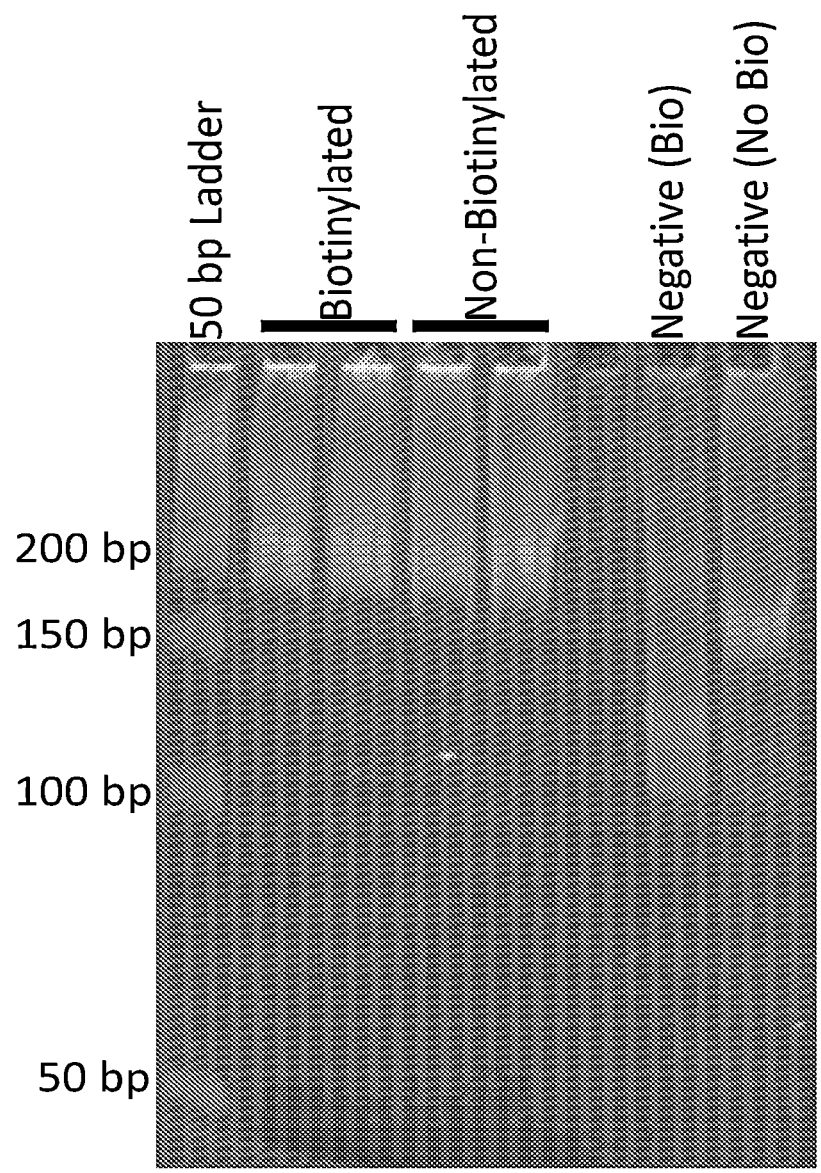
FIG. 13. is a photo of an acrylamide gel illustrating amplification of a specific target sequence in bacterial genomic DNA according to one embodiment of the present invention.
Figure 14:
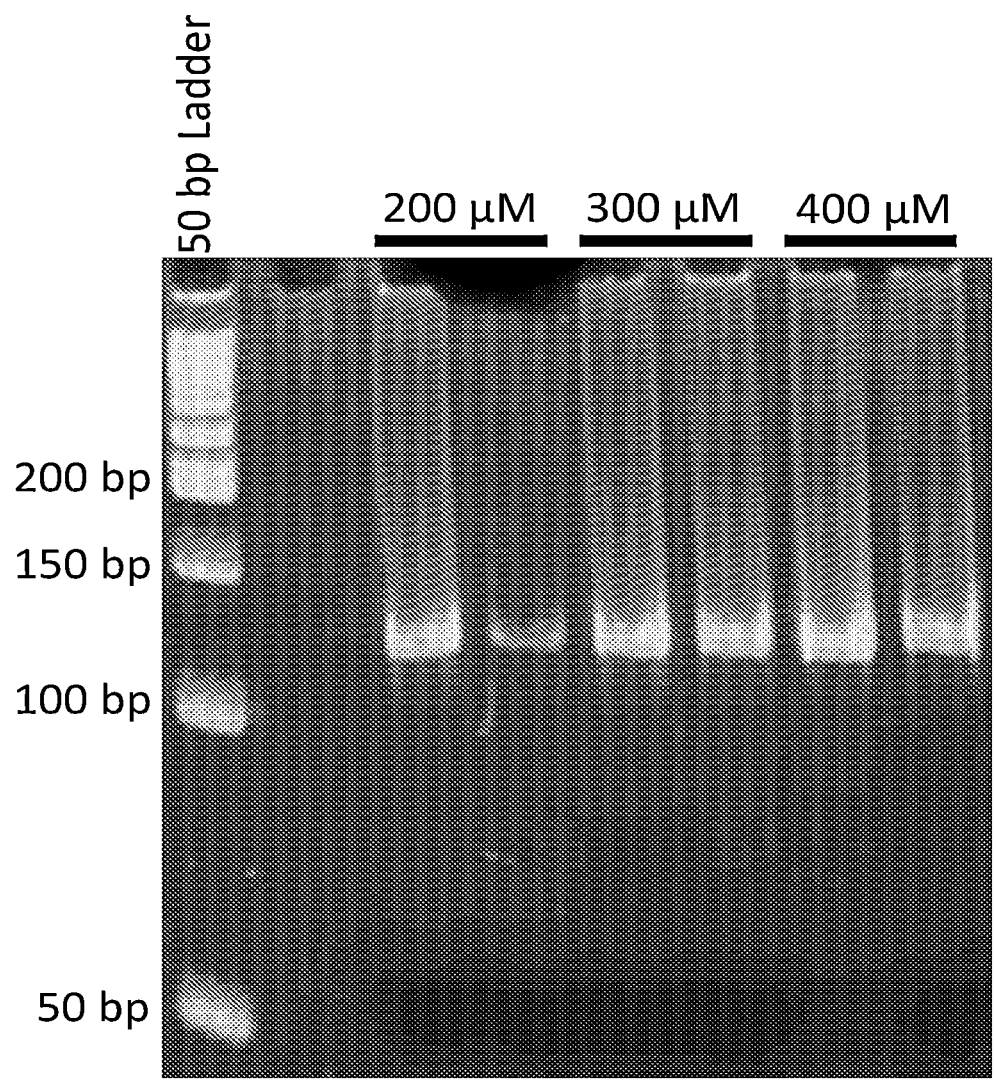
FIG. 14. is a photo of an acrylamide gel illustrating amplification of a specific target sequence present in chloroplast NDA according to one embodiment of the present invention.

Referring now to FIG. 10, a gel showing a target sequence present in a single stranded DNA template amplified according to one embodiment of the present invention is presented. A serial dilution of universal Influenza A single stranded DNA template (1E9 to 1E2 copies/L, Biosearch Technologies, Inc.) was amplified by OPCRar using the primers FP3 and RP4 in the presence of 15% DMSO to generate a product of 153 bp, which was visualized by electrophoresis on a 12% acrylamide gel stained with ethidium bromide (Left panel). As a comparison, identical dilutions were used as a starting template for real time PCR using the primers set UniAfCDC/UniArCDC and TaqMan probe UniApCDC (Right panel). OPCRar reactions were first heated to 85° C. for 2 minutes, then cycled between 80° C. for 15 sec and 65° C. for 15 sec, repeated 40 times. RT-PCR reactions were heated to 95° C. for 2 minutes, then cycled 45 times between 95° C. for 10 sec and 58° C. for 40 sec. It is evident that OPCRar has a similar sensitivity to conventional PCR reactions when properly optimized.

EXAMPLE 3

Method of Amplification of a Specific Sequence Present on Plasmid DNA by OPCRar

To demonstrate that OPCRar is capable of amplifying a specific target sequence present in a double stranded plasmid DNA, we used two OPCRar primers, primer hyvl_For and primer hyvl_Rev, to generate a 139 bp sequence from a plasmid containing the C. Liberibacter asiaticus hyvl gene by the OPCRar system. OPCRar Buffer (10.times.) was premade and contained 400 mM Tris-HCl (pH 8.4), 10 mM ammonium sulfate, 100 mM potassium chloride, and 0.25% Triton X-100. A 20 μL OPCRar solution was set up by mixing:

- 9.4 μl water
- 2.0 μL 10.times. OPCRar Buffer
- 2.0 μL DMSO
- 0.4 μL potassium chloride (2 M)
- 0.5 μl magnesium chloride (100 mM)
- 0.5 μl dithiothreitol (100 mM)
- 0.5 μL dNTPs (10 mM)
- 2.0 μL Primer set hyvl_For and hyvl_Rev (8 UM each)
- 0.5 μL VentR (exo-) DNA Polymerase (2 U/μL)
- 0.2 μL Et SSB, Extreme Thermostable Single Stranded Binding Protein (500 μg/mL)
- 2.0 μL of DNA extracted from healthy and C. Liberibacter infected tissue (17.2 ng/μL)

A titration with DMSO was performed from 13-8% v/v. The reaction was heated at 85° C. for 2 minutes to denature the template and then cycled 40 times, oscillating between 80° C. for 10 seconds, and 65° C. for 10 seconds. After the reactions were complete, 5 μl of OPCRar product was mixed with 2 μl of 6.times. Sample Loading Buffer (New England BioLabs) and 1 μl of formamide, run on a 12% acrylamide gel, and visualized with ethidium bromide. A 139 bp product was clearly observed for all samples (FIG. 11), and matches the predicted length of the OPCRar target sequence.

Referring now to FIG. 11, a gel of a specific target sequence present in plasmid DNA amplified according to one embodiment of the present invention is presented. A plasmid containing the C. Liberibacter asiaticus hyvl gene (17.2 ng/μL) was used as a starting template, and the concentration of DMSO was titrated from 13-8% v/v. All reactions were performed using VentR(exo-) DNA polymerase, Et SSB, and the primers hyvl_For and hyvl_Rev. The reactions were heated at 85° C. for 2 minutes to denature the template and then cycled 40 times, oscillating between 80° C. for 10 seconds, and 65° C. for 10 seconds. The OPCRar products were visualized on a 12% acrylamide gel, stained with ethidium bromide. A 139 bp product matching the predicted length of the target sequence was clearly observed at all DMSO concentrations tested.

EXAMPLE 4

Method of Amplification of a RNA Target Sequence of a Human Pathogenic Virus Present in Nasal Aspirate by OPCRar To demonstrate that OPCRar is capable of amplifying a specific target sequence present in a single stranded RNA template, we used the OPCRar primer pair, FP3 and RP4, to generate a 153 bp sequence from ribonucleic acid isolated from clinical nasal aspirates either infected or uninfected with Influenza A virus. OPCRar Buffer (10.times.) was premade and contained 400 mM Tris-HCl (pH 8.4), 10 mM ammonium sulfate, 100 mM potassium chloride, and 0.25% Triton X-100. A 20 μL OPCRar solution was set up by combining:

- 9.3 μl water
- 2.0 μL 10.times. OPCRar Buffer
- 3.0 μL DMSO
- 0.4 μL potassium chloride (2 M)
- 0.5 μl magnesium chloride (100 mM)
- 0.5 μl dithiothreitol (100 mM)
- 0.5 μL dNTPs (10 mM)
- 2.0 μL Primer set FP3 and RP4 (8 μM each)
- 0.5 μL VentR (exo-) DNA Polymerase (2 U/μL)
- 0.2 μL Et SSB, Extreme Thermostable Single Stranded Binding Protein (500 μg/mL)
- 0.1 μL Superscript III Reverse Transcriptase (200 U/μL)
- 2.0 μL of Nucleic acid isolated from clinical Nasal Aspirate (0.3 ng/μL)

The reaction was incubated at 55° C. for 5 minutes to generate cDNA, heated to 85° C. for 2 minutes to denature the template and then cycled 40 times, oscillating between 80° C. for 10 seconds, and 65° C. for 10 seconds. After the reactions were complete, 5 μl of OPCRar product was mixed with 2 μl of 6.times. Sample Loading Buffer (New England BioLabs) and 1 μL of formamide, run on a 12% acrylamide gel, and visualized with ethidium bromide. A 153 bp product was clearly observed in the positive, but not negative clinical sample (FIG. 12), and matches the predicted length of the OPCRar target sequence.

Referring now to FIG. 12, a gel illustrating a specific target sequence present in single stranded RNA amplified according to one embodiment of the present invention is illustrated. Ribonucleic acid isolated from nasal aspirates either infected or uninfected with Influenza A virus (0.3 ng/μL) was used as template. All reactions were performed using Superscript III reverse transcriptase, VentR(exo-) DNA polymerase, Et SSB, and the primers FP3 and RP4, in the presence of 15% DMSO. The reaction was incubated at 55° C. for 5 minutes to generate cDNA, heated to 85° C. for 2 minutes to denature the template and then cycled 40 times, oscillating between 80° C. for 10 seconds, and 65° C. for 10 seconds. The OPCRar products were visualized on a 12% acrylamide gel, stained with ethidium bromide. A 153 bp product matching the predicted length of the target sequence was clearly observed in the positive, but not negative, clinical sample.

EXAMPLE 5

Method of Amplification of a Target Sequence from a Pathogenic Plant Bacteria by OPCRar To demonstrate that OPCRar is capable of amplifying a specific target sequence present in a pathogenic bacterial genome, we used the OPCRar primer pair, EU523377-F-57 and EU523377-R-56, to generate a 213 bp fragment of the C. Liberibacter asiaticus elongation factor gene from total nucleic acid isolated from infected plant tissue. OPCRar Buffer (10.times.) was premade and contained 400 mM Tris-HCl (pH 8.4), 10 mM ammonium sulfate, 100 mM potassium chloride, and 0.25% Triton X-100. A 20 μL OPCRar solution was set up by combining:

8.4 μl water
2.0 μL 10.times. OPCRar Buffer
3.0 μL DMSO
0.4 μL potassium chloride (2 M)
0.5 μL magnesium chloride (100 mM)
0.5 μl dithiothreitol (100 mM)
0.5 μL dNTPs (10 mM)
2.0 μL Primer set EU523377-F-57 and EU523377-R-56 (4 μM each), primer EU523377-F-57 was either biotinylated (5') or non-biotinylated
0.5 μl VentR (exo-) DNA Polymerase (2 U/μL)
0.2 μL Et SSB, Extreme Thermostable Single Stranded Binding Protein (500 μg/mL)
2.0 μL of Total nucleic acid isolated from C. Liberibacter asiaticus infected plant tissue (1.1 ng/μL)

To demonstrate that primer modifications are compatible with OPCRar, the forward primer EU523377-F-57 was biotinylated at the 5' end in some reactions. OPCRar solutions were heated at 85° C. for 2 minutes to denature the template and then cycled 40 times, oscillating between 80° C. for 15 seconds, and 65° C. for 15 seconds. After the reactions were complete, 5 μL of OPCRar product was mixed with 2 μl of 6.times. Sample Loading Buffer (New England BioLabs) and 1 μL of formamide, run on a 12% acrylamide gel, and visualized with ethidium bromide. A 213 bp product was clearly observed for all samples, and matches the predicted length of the OPCRar target sequence (FIG. 13).

Referring now to FIG. 13, a gel of a specific target sequence present in bacterial genomic DNA as amplified according to one embodiment of the present invention is presented. Total nucleic acid isolated from C. Liberibacter asiaticus-infected leaf tissue (1.1 ng/μL) was used as a starting template. All reactions were performed using VentR (exo-) DNA polymerase, Et SSB, and the primers EU523377-F-57 and EU523377-R-56, in the presence of 15% DMSO. Primer EU523377-F-57 was either biotinylated at the 5' end of the oligonucleotide or unmodified. OPCRar solutions were heated at 85° C. for 2 minutes to denature the template and then cycled 40 times, oscillating between 80° C. for 15 seconds, and 65° C. for 15 seconds. The amplified products were visualized on a 12% acrylamide gel, stained with ethidium bromide. A 213 bp product was clearly observed for all positive samples and no negative samples, matching the predicted length of the OPCRar target sequence.

EXAMPLE 6

Method of Amplification of a Specific Sequence on Organelle DNA

To demonstrate that OPCRar is capable of amplifying a specific target sequence present in organelle DNA, in this case chloroplast DNA, we used the OPCRar primer pair, rbcL_For and rbcL_Rev, to generate a 137 bp fragment of the rbcL gene of plant from total nucleic acid isolated from plant tissue either infected or uninfected with C. Liberibacter asiaticus. OPCRar Buffer (10.times.) was premade and contained 400 mM Tris-HCl (pH 8.4), 10 mM ammonium sulfate, 100 mM potassium chloride, and 0.25% Triton X-100. A 20 μl OPCRar solution was set up by combining:

8.4 μL water
2.0 μL 10.times. OPCRar Buffer
3.0 μL DMSO
0.4 μL potassium chloride (2 M)
0.5 μL magnesium chloride (100 mM)
0.5 μL dithiothreitol (100 mM)
0.5 μL dNTPs (10 mM)
2.0 μl Primer set rbcL_For and rbcL_Rev (2 or 4 μM each)
0.5 μL VentR (exo-) DNA Polymerase (2 U/μL)
0.2 μL Et SSB, Extreme Thermostable Single Stranded Binding Protein (500 μg/mL)
2.0 μL of Total nucleic acid isolated from leaf tissue (3.3 ng/μL)

Two different concentrations of the primer pair rbcL_For and rbcL_Rev were used to determine a threshold for the primer concentration necessary to efficiently amplify the rbcL gene fragment. The reaction was heated at 85° C. for 2 minutes to denature the template and then cycled 40 times, oscillating between 76° C. for 10 seconds, and 60° C. for 10 seconds. After the reactions were complete, 5 μl of OPCRar product was mixed with 2 μL of 6.times. Sample Loading Buffer (New England BioLabs) and 1 μL of formamide, run on a 12% acrylamide gel, and visualized with ethidium bromide. A 137 bp product was clearly observed for both infected and uninfected samples, and matches the predicted length of the OPCRar target sequence (FIG. 14).

Referring now to FIG. 14, amplification of a specific target sequence present in chloroplast DNA according to one embodiment of the present invention is presented in a gel. Total nucleic acid isolated from either C. Liberibacter asiaticus-infected (I) or uninfected (ii) leaf tissue (3.3 ng/μL) was used as a starting template. All reactions were performed using VentR(exo-) DNA polymerase, Et SSB, and the primers rbcL_For and rbcL_Rev, in the presence of 10% DMSO. OPCRar solutions were heated at 85° C. for 2 minutes to denature the template and then cycled 40 times, oscillating between 76° C. for 10 seconds, and 60° C. for 10 seconds. The amplified products were visualized on a 12% acrylamide gel, stained with ethidium bromide. A 137 bp product was clearly observed for all positive samples, and matches the predicted length of the OPCRar target sequence.

EXAMPLE 7

Method of Multiplex Amplification of a Target Sequence and Positive Control by OPCRar To demonstrate that OPCRar is capable of amplifying multiple specific target sequences, we amplified the nucleic acid extracted from C. Liberibacter asiaticus infected plant tissue with the OPCRar primer pairs, hyvl_For/hyvl_Rev, and rbcL_For/rbcL_Rev. These primer sets generate products of 139 and 137 bp, respectively. OPCRar Buffer (10.times.) was premade and contained 400 mM Tris-HCl (pH 8.4), 10 mM ammonium sulfate, 100 mM potassium chloride, and 0.25% Triton X-100. A 20 µL OPCRar solution was set up by combining:

6.4 µl water
2.0 µL 10.times. OPCRar Buffer
3.0 µL DMSO
0.4 µL potassium chloride (2 M)
0.5 µl magnesium chloride (100 mM)
0.5 µL dithiothreitol (100 mM)
0.5 µL dNTPs (10 mM)
2.0 µl Primer set rbcL_For and rbcL_Rev (2 or 3 µM each)
2.0µ Primer set hyvl_For and hyvl_Rev (8 µM each)
0.5 µL VentR (exo-) DNA Polymerase (2 U/µL)
0.2 µL Et SSB, Extreme Thermostable Single Stranded Binding Protein (500 µg/mL)
2.0 µL of Total nucleic acid isolated from leaf tissue (3.3 ng/µL)

Two different concentrations of the primer pair rbcL_For and rbcL_Rev were used to determine a threshold for the primer concentration necessary to efficiently amplify the rbcL gene fragment in the presence of 800 nM primers specific for the hyvl gene fragment. The reaction was heated at 85° C. for 2 minutes to denature the template and then cycled 40 times, oscillating between 76° C. for 10 seconds, and 60° C. for 10 seconds. After the reactions were complete, 5 µL of OPCRar product was mixed with 2 µL of 6.times. Sample Loading Buffer (New England BioLabs) and 1 µL of formamide, run on a 12% acrylamide gel, and visualized with ethidium bromide. Both 139 bp and 137 bp products are clearly observed, matching the predicted length of the OPCRar target sequences. For clarity, OPCRar products generated using both primer pairs alone (Examples 3 and 6) were run alongside the multiplex reactions (FIG. 15).

Figure 15:
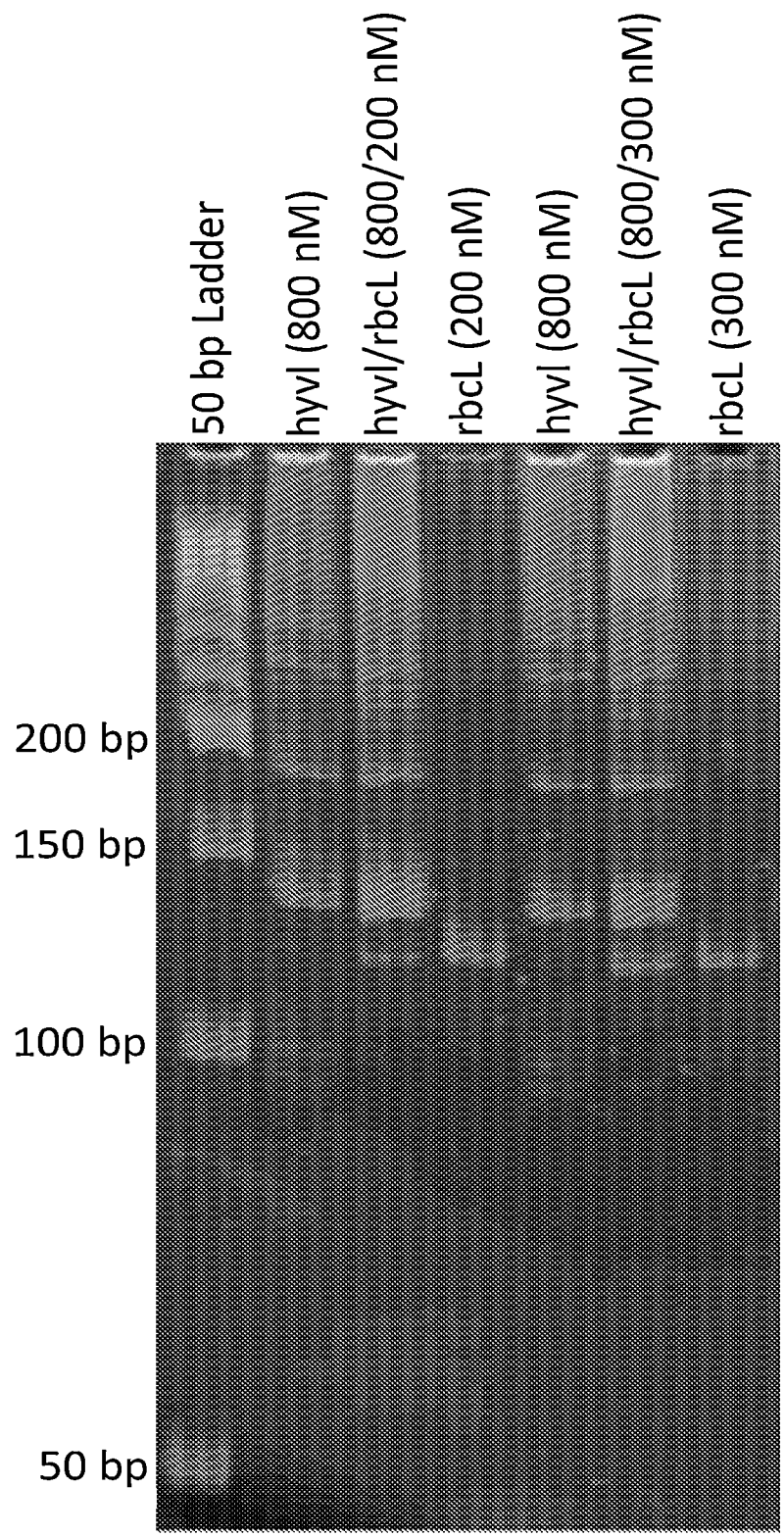
FIG. 15. is a photo of an acrylamide gel illustrating amplification of two target sequenced according to one embodiment of the present invention.

Referring now to FIG. 15, a gel illustrating amplification products of multiplex of two target sequences according to one embodiment of the present invention is presented. Total nucleic acid isolated from C. Liberibacter asiaticus-infected leaf tissue (3.3 ng/µL) was used as a starting template. All reactions were performed using VentR(exo-) DNA polymerase, Et SSB, and the primers sets hyvl_For/hyvl_Rev and rbcL_For/rbcL_Rev at the indicated concentrations, in the presence of 10% DMSO. Multiplex OPCRar solutions were heated at 85° C. for 2 minutes to denature the template and then cycled 40 times, oscillating between 76° C. for 10 seconds, and 60° C. for 10 seconds. The multiplex products were visualized on a 12% acrylamide gel, stained with ethidium bromide. When compared to OPCRar products generated from either primer set alone (See FIGS. 11 and 15), both 139 and 137 bp products were clearly observed.

Referring now to FIG. 16, an amplification product resulting from a reaction in the presence of Et SSB according to one embodiment of the present invention is illustrated. SSB enhances the amplification efficiency at lower melting temperatures using the system and method of the present invention. We investigated the use of extreme thermostable single strand binding protein "ET SSB" to show it aids the performance of OPCRar at certain melting temperatures. OPCRar reaction was performed for a HLB pathogen target with purified leaf sample DNA containing HLB disease genes. Template was DNA purified from citrus leaf of a C. Liberibacter infected tree. Primers were hyvl_For/and hyvl_Rev. Thermocycler conditions were: Initial melt of 85° C. for 2 minutes, followed by 40 cycles denaturation of either 76° C. or 74° C. for 10 seconds and annealing at 60° C. for 10 seconds. The results indicated in the presence of Et SSB resulted in the amplification of the C. Liberibacter target at all assayed temperature regimens. The comparative OPCRar experiment was done in duplicates in the presence of ET SSB protein and no ET SSB. A standard PCR Thermocycler with precise temperature control was used to allow the evaluation of amplification performance with and without SSB. Results indicated that in the presence of ET SSB we picked up amplified HLB at 74° C. and without ET SSB it was unobservable.

Referring now to FIG. 17, gel electrophoresis of OPCRar reactions conducted using hyvl_For and hyvl_Rev primers and purified C. Liberibacter DNA isolated from the leaf of an infected tree is shown according to one embodiment of the present invention wherein the reaction does not include ramping parameters involved in a typical PCR thermocycler FIG. 17A or does include ramping time to cycling temperature FIG. 17B. Ramping as used herein is a reference to the heating up (e.g. in each thermal cycling, the heating process to raise the amplification reaction temperature from annealing to denaturing temperature is called ramping up or cooling down from denaturation temperature to annealing temperature is called ramp down. All the conventional PCR cyclers and methods, have controlled heating design where ramping up is about >3 deg/second, and ramping down rate is about >1 deg/second. Ramping time is not included in the typical cycling profiles, the instrument does not start counting time duration during denaturation, annealing and extension stage until the desired temperature is reached. For instance, denaturation time is 10 second at 90 deg, the instrument will not starting counting the 10 second time until 90 deg is reached. In contrast, a system and method of the present invention provides for a low cost heater device which is designed for example the 80 deg for 10 second means the time starts counting when the heating process starts (rather than waiting until the desired denaturing temperature is reached). FIG. 17A: we examined the OPCRar amplification of a HLB disease (a citrus greening disease pathogen, Huang Long Bing) target in a low cost, thermal heater engine (without active cooling and precise temperature control, >.+-. 2 degree fluctuation, (see for example systems and apparatus as disclosed in 61/477,357). OPCRar 20 μL reactions were conducted in microheater reaction chambers under microprocessor control in a device developed by Mesa Tech International, Inc. (MTI Device) or in a traditional PCR thermocycler (PCR Thermocycler) such that the 10-second dwell times for each temperature segment of the program were calculated starting immediately after command to change temperatures was executed by the microprocessor (i.e. no ramping time FIG. 17A). This is in contrast to 10-second dwell times for each temperature segment of the program calculated starting immediately after the target temperature was detected by the temperature sensor located at the reaction well (i.e. ramping time FIG. 17B). The PCR Thermocycler conditions were as follows: Initial Melt: 85° C. for 2 minutes, followed by 40 cycles of 80° C. for 10 seconds and 60° C. for 10 seconds. The MTI Device conditions were as follows: Initial Melt: 85° C. for 2 minutes, 40 cycles of 82° C. for 10 seconds and 59° C. for 20 seconds.

FIG. 17A: First Lane, OPCRar amplification (20 μl reaction) without separate ramping. From the left: 50 bp standard DNA size ladder; second and third lances: OPCRar amplification reaction (in duplicate, 2.sup.nd and 3.sup.rd lanes) in a standard PCR thermal cycler engine where ramp step and precise temperature control are accommodated. Initial Melt: 85° C. for 2 minutes, Cycling between denaturation of 80° C. for 10 seconds and annealing of 60° C. for 10 seconds with 40 cycles. The 4th and 5.sup.th lanes: OPCRar amplification performed in a low cost thermal engine without active cooling and/or a separate ramping control. The thermal engine ramps to either 80° C. denaturation or ramping down to 60° C. annealing temperature from the ambient field temperatures (.about.25 deg). as compared to not having any ramping stage for either denaturation or annealing temperature. HLB OPCRar was performed with purified plant DNA containing HLB disease target sequences in a 20 µl reaction. We used the PCR Thermocycler for a positive control for the MTI Device test. The PCR Thermocycler conditions were the following: The MTI Device Thermocycler conditions for no ramping were the following: Initial Melt: 85° C. for 2 minutes, Cycling between denaturation of 82° C. for 10 seconds and annealing of 59° C. for 20 seconds. The cycling was repeated 40 times. The MTI device thermocycler for ramping up stages were the same conditions except there was ramp up stage <10 seconds and ramp down stage <20 seconds. Data suggested HLB OPCRar can still amplify up HLB amplicon even without ramp up and ramp down stages. Comparison of 17A and 17B reveals a significant improvement in the yield of amplification product when ramp time is provided.

Figure 16A:
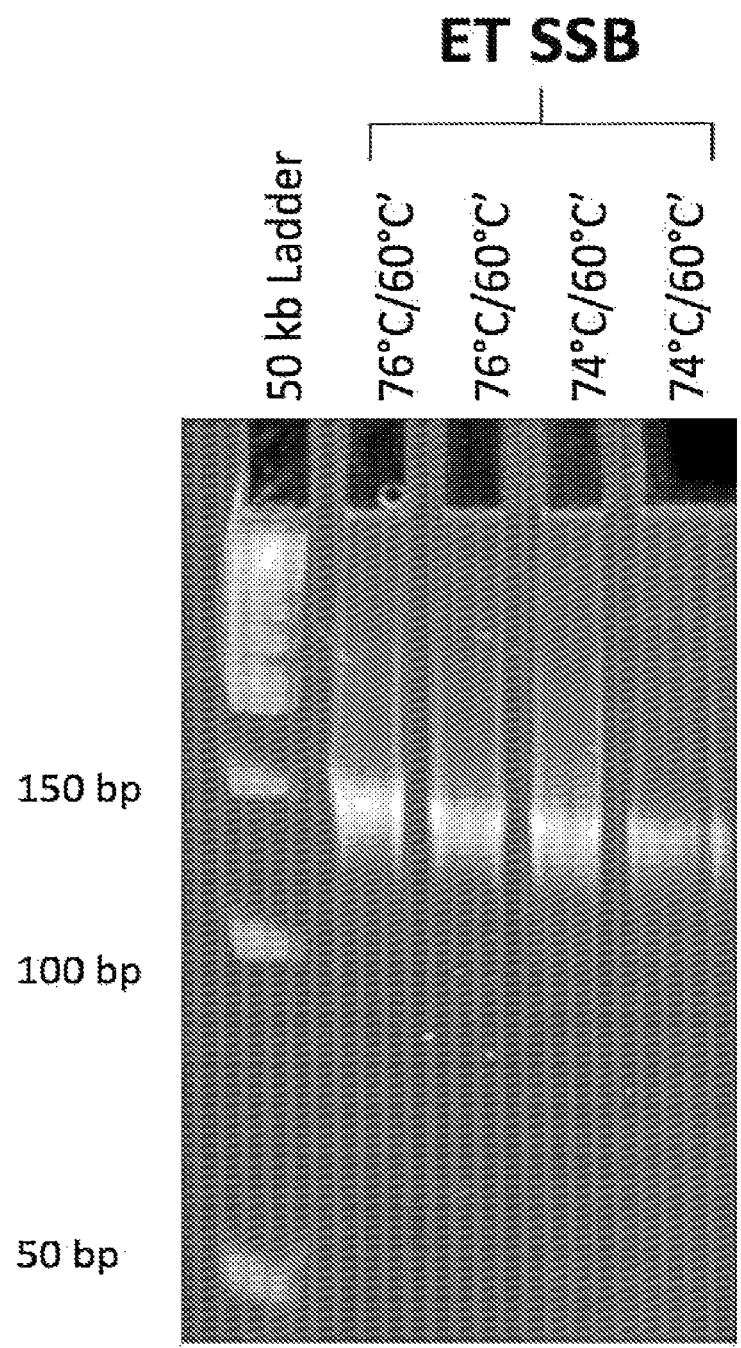
FIGS. 16A and 16B represent photos of acrylamide gels illustrating amplification of a target sequence in the presence of SSB at lower melting temperatures according to one embodiment of the present invention.
Figure 16B:
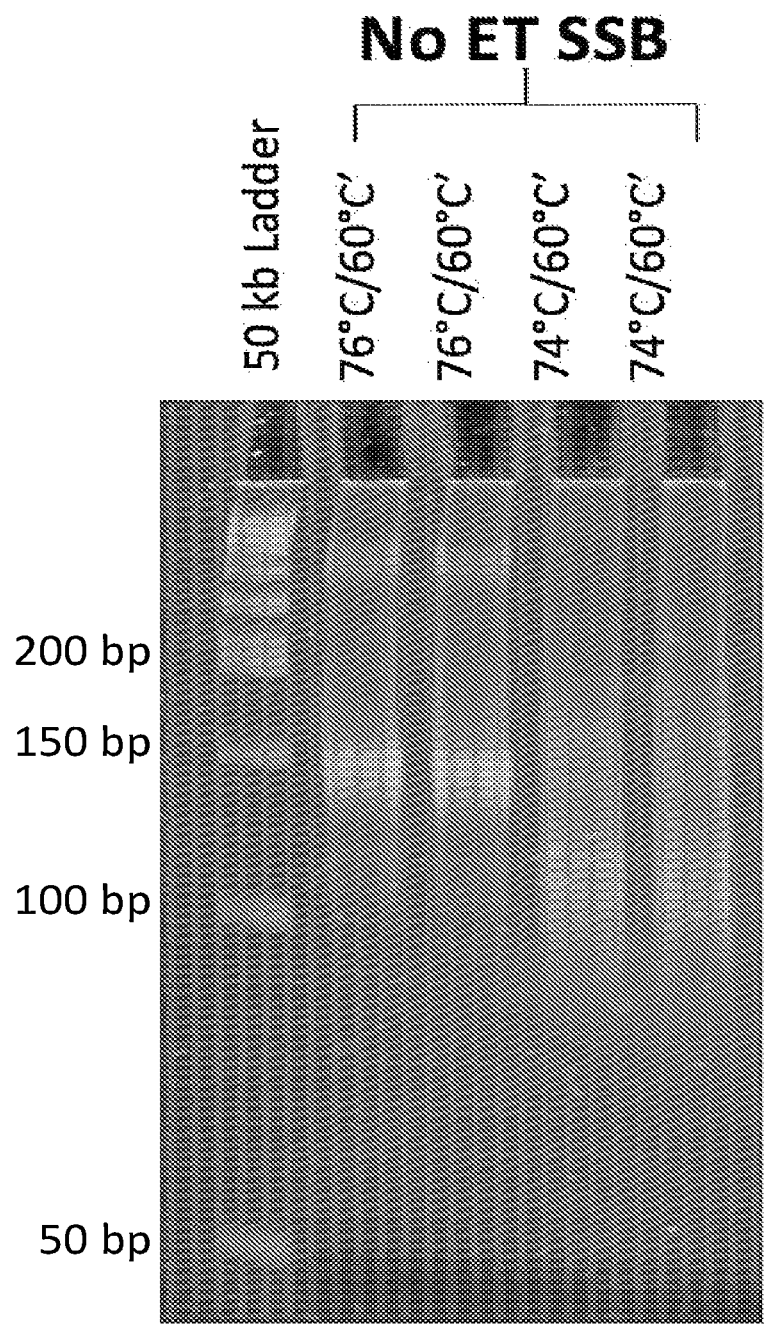
Figure 17A:
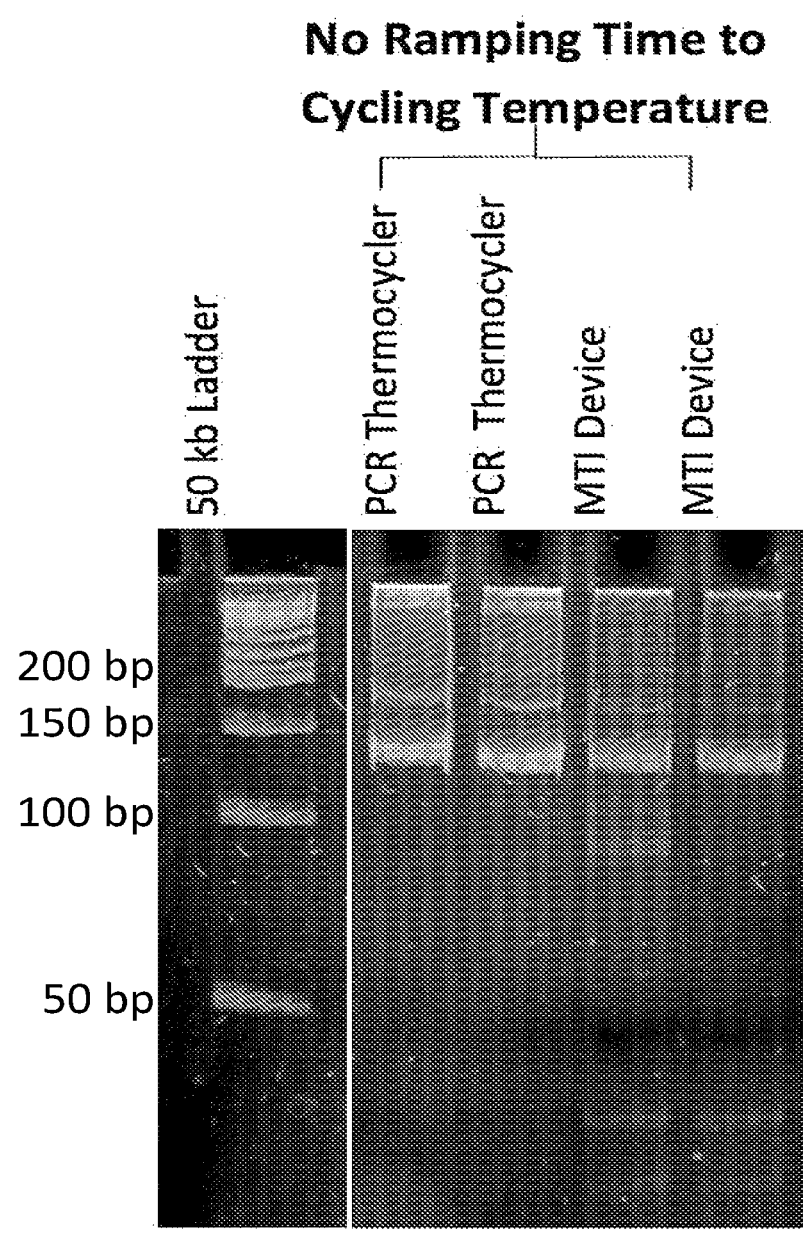
FIGS. 17A and 17B represent photos of acrylamide gels illustrating amplification of a target with precise temperature control and/or rapid ramping parameters as required in a typical PCR thermocycler.
Figure 17B:
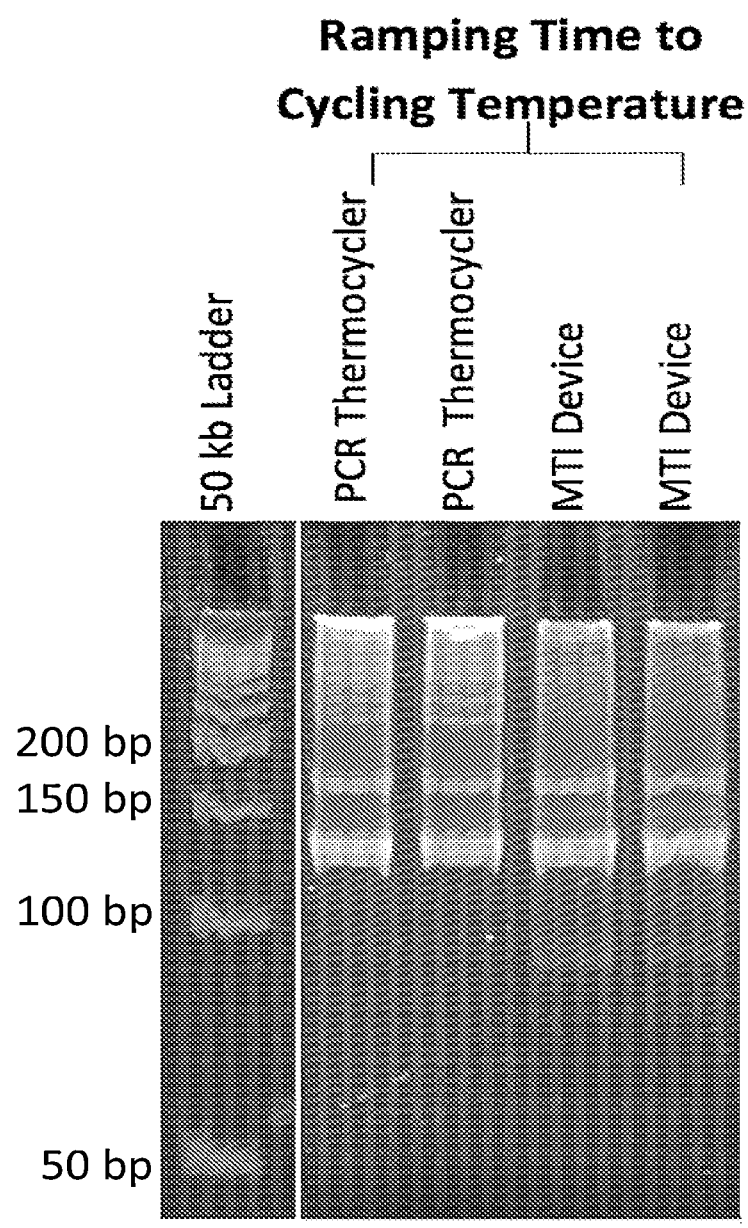
Figure 18:
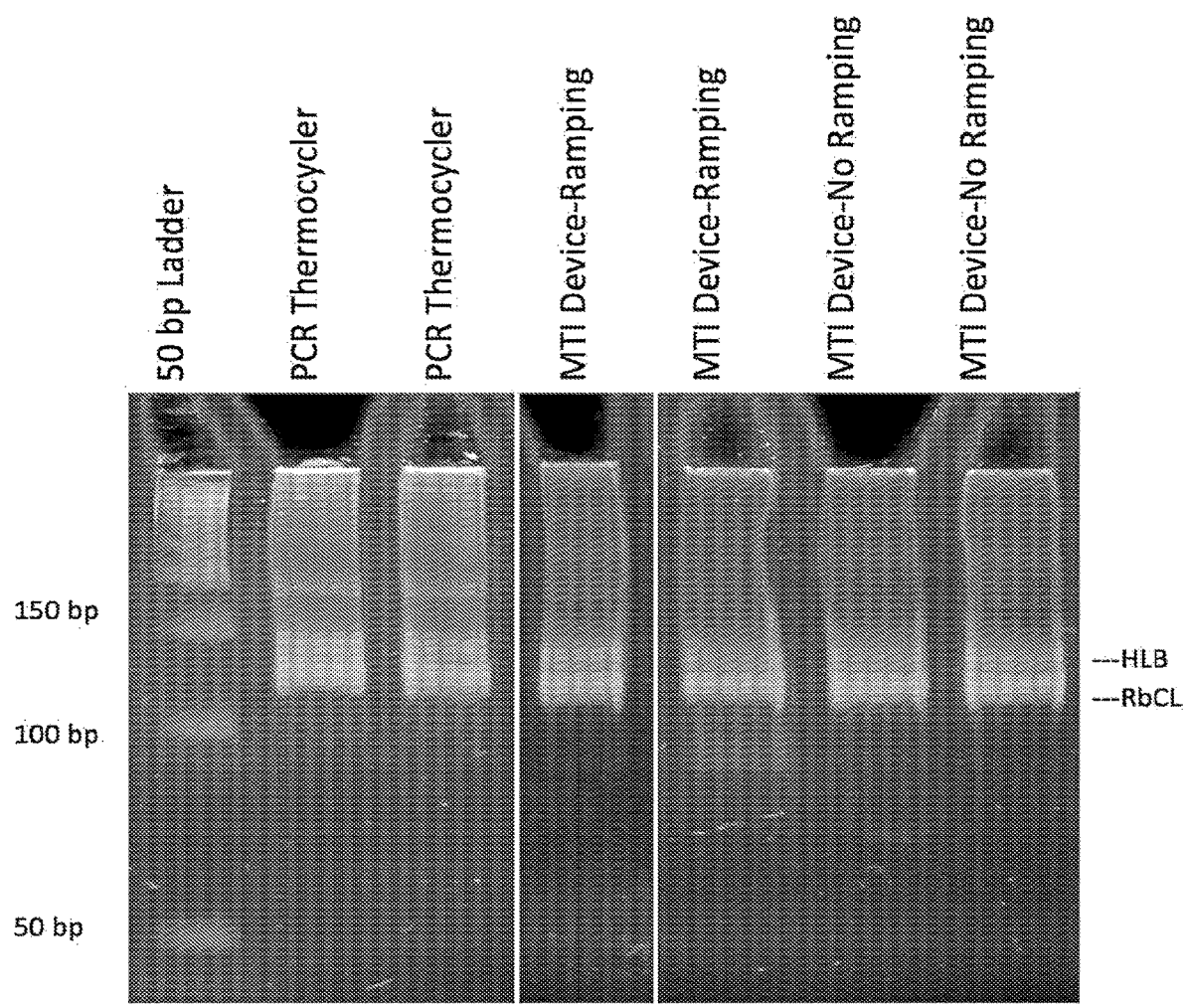
FIG. 18 is a photo of an acrylamide gel illustrating amplification of a target Rbcl amplified in the low cost heater without ramping or precise temperature control.

Referring now to FIG. 18, multiplexed OPCRar reactions according to one embodiment of the present invention containing two primer sets in MTI's thermal resistor-based low cost amplification device as described above: 1) hyvl_For and hyvl_Rev primers specific for a C. Liberibacter DNA target and 2) primers rbcl_(Ribulose-1,5-bisphosphate carboxylase oxygenase) For and rbcl_Rev specific for a citrus house keeping gene rbcL.amplification product are illustrated in the gel. The reaction products resulting from PCR amplification as described and performed in a low cost heater without ramping (e.g. 5 deg/second in PCR device) and without precise temperature control were run on a gel. We tested the RbCL internal positive control with HLB primers in the PCR thermocycler and the MTI Device (with ramping or no ramping program). We performed a 40 µl reaction with purified HLB sample. The PCR thermocycler conditions were the following: Initial Melt: 85° C. for 2 minutes, Cycling between denaturation of 80° C. for 10 seconds and annealing of 60° C. for 10 seconds. The MTI Device amplification conditions were the following: Initial Melt: 90° C. for 2 minutes, cycling between denaturation of 82° C. for 10 seconds and annealing of 59° C. for 20 seconds. We discovered without ramping it was still able to amplify up both HLB and RbCL primer sequences. HLB product around.about.147 bp and RbCL product.about.140 bp. The MTI Device for both conditions was comparable to the PCR Thermocycler amplified product. The forward primer for this reaction is ccagccttga togttacaaa gggcgatgct acaacatt (SEQ ID NO 9) (Tm of about 73.9 C (10% DMSO, 76/60 C) and the reverse primer iscatgttagta acagaacctt cttcaaaaag gtctaacggg taa (SEQ ID NO 10) (Tm of about 71.2 C (10% DMSO, 76/60 C). OPCRar reactions were conducted with or without the inclusion of ramp times in the temperature dwell times (as described for FIGS. 16 and 17) as indicated. 40 µl reactions were conducted using purified citrus leaf DNA from a C. Liberibacter infected tree. The PCR Thermocycler control conditions were as follows: Initial Melt: 85° C. for 2 minutes, 40 cycles of 80° C. for 10 seconds and 60° C. for 10 seconds. The MTI Device amplification conditions were as follows: Initial Melt: 90° C. for 2 minutes, 40 cycles of 82° C. for 10 seconds and 59° C. for 20 seconds. The results revealed without the inclusion of ramp times in the dwell time calculation, the MTI device was able to amplify up both C. Liberibacter and rbcL sequences. The C. Liberibacter product is approximately 147 bp (HLB) and rbcL (RbCL) product is approximately 140 bp.

All primer melting temperatures (Tm) calculated using IDT OligoAnalyzer 3.1 (Integrated DNA Technologies, Inc., Coralville, Iowa) using the Primer 3 Tm calculating software where salt, dNTP, Mg, primer concentration parameters are considered using the following parameters:

Oligonucleotide Concentration: 0.25 µM; Na.sup.+ Concentration: 50 mM; Mg.sup.++ Concentration=2.5 mM; dNTPs Concentration=0.25 µM. Symbol "a" means adenine, "g" means guanine, "c" means cytosine, "t" means thymine, "u" means uracil, "r" means purine, "y" means pyrimidine, "m" means amino, "k" means keto, "n" means any of a or g or c or t/u, unknown, or other.

(SEQ ID NO 1)
   ACCESSION NUMBER: CY087034
   TYPE: Viral RNA
   LENGTH: 1010
   ORGANISM: Influenza A Virus (H1N1)
Other INFORMATION: Matrix Protein 2 (M2) and Matrix Protein 1 (M1) Genes
(SEQ ID NO 2)
   TYPE: Forward Primer
   NAME: FP3
   LENGTH: 46
   Tm: mean 75° C.
(SEQ ID NO 3)
   TYPE: Reverse Primer
   NAME: RP3
   LENGTH: 40
   Tm: mean 77.8° C.
(SEQ ID NO 4)
   TYPE: Reverse Primer
   NAME: RP4
   LENGTH: 46
   Tm: mean 74.7° C.
(SEQ ID NO 5)
   TYPE: Forward Primer
   NAME: UniAfCDC
   LENGTH: 22
   Tm: mean 65.0° C.
(SEQ ID NO 6)
   TYPE: Reverse Primer
   NAME: UniArCDC
   LENGTH: 24
   Tm: mean 66.6° C.
(SEQ ID NO 7) FAM-tgcagtcctc gctcactggg cacg-BHQ
   TYPE: TaqMan Probe
   NAME: UniApCDC
   LENGTH: 24
   Tm: 73.4° C.
(SEQ ID NO 8)
   ACCESSION NUMBER: AB505957
   TYPE: Chloroplast DNA
   LENGTH: 1326
ORGANISM: *Citrus sinensis* OTHER INFORMATION: RbcL, Ribulose-1,5-Bisphosphate Carboxylase/Oxygenase Large Subunit
(SEQ ID NO 9)
   TYPE: Forward Primer
   NAME: rbcL_For
   LENGTH: 38
   Tm: 73.9° C.

(SEQ ID NO 10)
  TYPE: Reverse Primer
  NAME: rbcL_Rev
  LENGTH: 43
  Tm: 71.2° C.
(SEQ ID NO 11)
  ACCESSION NUMBER: From EU523377
  TYPE: Bacterial DNA
  LENGTH: 890
  Organism: Candidatus Liberibacter Asiaticus OTHER INFORMATION: Elongation Factor Ts
(SEQ ID NO 12)
  TYPE: Forward Primer
  NAME: NBEU523377-F-57
  LENGTH: 57
  Tm: 75.8° C.
(SEQ ID NO 13) [Biotin-5]tcttcgtatc ttcatgcttc tccttctgag ggtttaggat cgattggtgt tcttgta
  TYPE: Biotinylated Forward Primer
  NAME: EU523377-F-57
  LENGTH: 57
  Tm: 75.8° C.
(SEQ ID NO 14)
  TYPE: Forward Primer
  NAME: HLBForSh
  LENGTH: 47
  Tm: 75.6° C.
(SEQ ID NO 15)
  TYPE: Reverse Primer
  NAME: EU523377-R-56
  LENGTH: 56
  Tm: 75.8° C.
(SEQ ID NO 16)
  TYPE: Reverse Primer
  NAME: HLBRevSh
  LENGTH: 49
  Tm: 75.5° C.
(SEQ ID NO 17)
  Target: Candidatus Liberibacter Asiaticus 16S Ribosomal RNA TYPE: Forward Primer (Underlined), Contains 5' Detection Sequence
  NAME: HLBas-P2
  LENGTH: 39
  Tm: 62.7° C.
(SEQ ID NO 18)
  Target: Candidatus Liberibacter Asiaticus 16S Ribosomal RNA TYPE: Reverse Primer (Underlined), Contains 5' T7 Promoter
  NAME: HLBr-P1
  LENGTH: 56
  Tm: 64.5° C.
(SEQ ID NO 19)
  TYPE: Forward Primer
  NAME: hyvl_For
  LENGTH: 45
  Tm: 72.2° C.
(SEQ ID NO 20)
  TYPE: Reverse Primer
  NAME: hyvl_Rev
  LENGTH: 51
  Tm: 70.9° C.

Although the invention has been described in detail with particular reference to the described embodiments, other embodiments can achieve the same results. Variations and modifications of the present invention will be obvious to those skilled in the art and it is intended to cover all such modifications and equivalents. The entire disclosures of all patents and publications cited above are hereby incorporated by reference.

What is claims is:

1. A method for amplifying a target nucleic acid sequence contained in a sample, the method comprising:
   contacting, in a reaction chamber, the sample with an amplification reaction mixture necessary for an amplification reaction, said amplification reaction mixture comprising a primer complementary to the target nucleic acid sequence;
   regulating a temperature of the amplification reaction between a denaturation temperature and an annealing temperature during a plurality of temperature cycles, wherein each temperature cycle is completed in a cycle time of 30 seconds or less, and wherein the regulating comprises applying heat to the reaction chamber; and
   amplifying the target nucleic acid sequence.

2. The method of claim 1, wherein the difference between the denaturation temperature and the annealing temperature is no greater than about 20° C.

3. The method of claim 1, wherein upon reaching the denaturation temperature or the annealing temperature, the temperature is maintained for about 15 second or less, 10 seconds or less, or 5 seconds or less.

4. The method of claim 1, wherein upon reaching the denaturation temperature or the annealing temperature, the temperature is immediately varied to the other temperature.

5. The method of claim 1, wherein the annealing temperature is no less than 50° C.

6. The method of claim 1, wherein the target nucleic acid sequence is a single stranded or double stranded DNA or RNA.

7. The method of claim 1, wherein the length of the target nucleic acid sequence is less than 1000 bp.

8. The method of claim 1, wherein the amplification reaction mixture comprises a pair of primers which bind to opposite strands of the target nucleic acid sequence.

9. The method of claim 8, wherein each primer in the pair of primers has a length and a GC content so that the melting temperature is ≥65° C.

10. The method of claim 8, wherein each primer in the pair of primers has a length of between 35-70 base pairs.

11. The method of claim 8, wherein each primer in the pair of primers has a length of between 40-47 base pairs.

12. The method of claim 1, wherein the amplification reaction mixture comprises: a monovalent cation; a divalent cation; dNTPs; DNA polymerase; a nucleic acid destabilizing agent comprising DMSO, formamide, or Betaine; a single stranded binding protein; or combinations thereof.

13. The method of claim 12, wherein the divalent cation is a salt comprising magnesium, manganese, copper, zinc, or any combination thereof.

14. The method of claim 12, wherein the monovalent cation is a salt comprising one or more of sodium, potassium, lithium, rubidium, cesium, ammonium, or any combination thereof.

15. The method of claim 12, wherein the DNA polymerase is a thermostable DNA polymerase.

16. The method of claim 12, wherein the nucleic acid destabilizing agent is at a concentration between 8 and 15 volume percent.

17. The method of claim 1, wherein the amplification reaction mixture comprises a single stranded binding protein.

18. The method of claim 17, wherein the single stranded binding protein is a thermal stable single stranded binding protein or non-thermal stable single stranded binding protein.

19. The method of claim 1, wherein the regulating comprises maintaining the denaturation temperature for about 5 seconds to about 15 seconds and maintaining the annealing temperature for about 5 seconds to about 15 seconds.

20. The method of claim 1, wherein the amplification reaction mixture comprises a DNA polymerase with strand displacement activity.

21. The method of claim 1, wherein during each temperature cycle, the denaturation temperature is maintained for a first time period and the annealing temperature is maintained for a second time period, wherein the first and second time periods differ from each other.

22. The method of claim 1, wherein the length of the target nucleic acid sequence is less than 500 bp.

23. The method of claim 1, wherein the regulating comprises applying the heat to a surface of the reaction chamber.

24. The method of claim 1, further comprising applying the heat using a heating element.

* * * * *

SEQUENCE LISTING

```
Sequence total quantity: 28
SEQ ID NO: 1            moltype = DNA  length = 1010
FEATURE                 Location/Qualifiers
variation               993
                        note = n is a, c, g, or t
variation               1002
                        note = n is a, c, g, or t
source                  1..1010
                        mol_type = genomic DNA
                        organism = Influenza A virus
SEQUENCE: 1
taaagatgag tcttctaacc gaggtcgaaa cgtacgttct ttctatcatc ccgtcaggcc    60
ccctcaaagc cgagatcgcg cagagactgg aaagtgtctt tgcaggaaag aacacagatc   120
ttgaggctct catggaatgg ctaaagacaa gaccaatctt gtcacctctg actaagggaa   180
ttttaggatt tgtgttcacg ctcaccgtgc ccagtgagcg aggactgcag cgtagacgct   240
ttgtccaaaa tgccctaaat gggaatgggg acccgaacaa catggataga gcagttaaac   300
tatacaagaa gctcaaagga gaaataacgt tccatgggc caaggaggtg tcactaagct   360
ttcaactggt gcacttgcca gttgcatggg cctcatatac aacaggatgg gaacagtgac   420
cacagaagct gcttttggtc tagtgtgtgc cacttgtgaa cagattgctg attcacagca   480
tcggtctcac agacaaatgg ctactaccac caatccacta atcaggcatg aaaacagaat   540
ggtgctggct agcactacgg caaaggctat ggaacagatg gctggatcga gtgaacaggc   600
agcagaggcc atggaggttg ctaatcagac taggcagatg gtacatgcaa tgagaactat   660
tgggactcat cctagctcca gtgctggtct gaaagatgac cttcttgaaa atttgcaggc   720
ctaccagaag cgaatgggag tgcagatgca gcgattcaag tgatcctctc gtcattgcag   780
caaatatcat tgggatcttg cacctgatat tgtggattac tgatcgtctt tttttcaaat   840
gtatttatcg tcgctttaaa tacggtttga aaagagggcc ttctacggaa ggagtgcctg   900
agtccatgag ggaagaatat caacaggaac agcagagtgc tgtggatgtt gacgatgtc   960
attttgtcaa catagagcta gagtaataga cgnttttgtcc anaatgccct              1010

SEQ ID NO: 2            moltype = DNA  length = 46
FEATURE                 Location/Qualifiers
misc_feature            1..46
                        note = forward primer designed for SEQ ID NO 1
source                  1..46
```

```
                        mol_type = other DNA
                        organism = synthetic construct
SEQUENCE: 2
ywctcatgga rtggctaaag acaagaccra tcctgtcacc tctgac              46

SEQ ID NO: 3            moltype = DNA   length = 40
FEATURE                 Location/Qualifiers
misc_feature            1..40
                        note = reverse primer designed for SEQ ID NO 1
source                  1..40
                        mol_type = other DNA
                        organism = synthetic construct
SEQUENCE: 3
agggcattyt ggacaaakcg tctacgytgc agtccycgyt                     40

SEQ ID NO: 4            moltype = DNA   length = 46
FEATURE                 Location/Qualifiers
misc_feature            1..46
                        note = reverse primer for SEQ ID NO 1
source                  1..46
                        mol_type = other DNA
                        organism = synthetic construct
SEQUENCE: 4
tttggrtctc cattyccatt tagggcatty tggacaaakc gtctat              46

SEQ ID NO: 5            moltype = DNA   length = 22
FEATURE                 Location/Qualifiers
misc_feature            1..22
                        note = forward primer UniAfCDC for SEQ ID NO 1
source                  1..22
                        mol_type = other DNA
                        organism = synthetic construct
SEQUENCE: 5
gaccratcct gtcacctctg ac                                        22

SEQ ID NO: 6            moltype = DNA   length = 24
FEATURE                 Location/Qualifiers
misc_feature            1..24
                        note = reverse primer UniArCDC designed for SEQ ID NO 1
source                  1..24
                        mol_type = other DNA
                        organism = synthetic construct
SEQUENCE: 6
agggcattyt ggacaaakcg tcta                                      24

SEQ ID NO: 7            moltype = DNA   length = 24
FEATURE                 Location/Qualifiers
misc_feature            1..24
                        note = TAQman probe UniApCDC
source                  1..24
                        mol_type = other DNA
                        organism = synthetic construct
SEQUENCE: 7
tgcagtcctc gctcactggg cacg                                      24

SEQ ID NO: 8            moltype = DNA   length = 1326
FEATURE                 Location/Qualifiers
source                  1..1326
                        mol_type = genomic DNA
                        organism = Citrus sinensis
SEQUENCE: 8
tgttggattc aaggccggtg ttaaagatta taaattgact tattatactc ctgactatgt   60
aaccaaagat actgatatct tggcagcatt ccgagtaact cctcagcccg gagttccacc  120
cgaggaagcg gggctgcgga tagctgcgga atcttctact ggtacctgga cagctgtgtg  180
gaccgatggg cttaccagcc ttgatcgtta caagggcga tgctacaaca ttgagcccgt   240
tgctggagaa gagaatcaat atatatgtta tgtagcttac ccgttagacc ttttgaaga   300
aggttctgtt actaacatgt ttacttccat tgtgggtaat gtatttggtt tcaaagcact   360
gcgcgctcta cgtctagagg atctactaat ccctcctgcg tatactaaaa cttccaagg    420
cccgcctcac ggcatccaag ttgagagaga taattgaac aagtatggcc gtccctcgtt   480
gggatgtact attaaaccta aactgggtt atccgcgaag aattatggta gggcggttta    540
tgaatgtcta cgtggtggac ttgactttac caaagatgat gagaacgtga actcccaacc   600
atttatgcgt tggagggacc gttcttatt ttgtgcggaa gctctttata aagcgcaagc     660
tgaaacaggt gaaatcaaag gtcattactt gaatgctact gcaggacat gcgaagaaat    720
gctaaaaagg gctgtctttg ccagagagtt gggagttcct atcgtaatgc atgactactt    780
aacaggggga ttcaccgcaa atactacctt ggctcattat tgccgagata atggtctact    840
tcttcacatc caccgtgcaa tgcatgcagt tattgataga cagaagaatc atggtatgca    900
ctttcgtgta ctagctaaag ctttgcgtct gtctggtgga gatcatattc acgccggtac    960
agtagtaggt aaacttgagg gggaaagaga cataaccttg ggatttgttg atttactacg   1020
tgatgatttt gttgaaaaag atcgaagccg cggtatttat ttcactcaag attgggtctc    1080
```

-continued

```
tataccaggt gttatacctg tggcttccgg gggtattcac gtttggcata tgcctgcgtt  1140
gacagagatc tttggagatg attccgtatt acaatttggt ggaggaactt taggacaccc  1200
ttggggaaat gcacccggcg ctgtagctaa tcgagtagct ctagaagcat gtgtacaagc  1260
tcgtaatgaa ggacgcgatc ttgctcgtga aggtaatgaa attatccggg aggctagcaa  1320
atggag                                                            1326

SEQ ID NO: 9            moltype = DNA  length = 38
FEATURE                 Location/Qualifiers
misc_feature            1..38
                        note = forward primer rbcL_For
source                  1..38
                        mol_type = other DNA
                        organism = synthetic construct
SEQUENCE: 9
ccagccttga tcgttacaaa gggcgatgct acaacatt                         38

SEQ ID NO: 10           moltype = DNA  length = 43
FEATURE                 Location/Qualifiers
misc_feature            1..43
                        note = reverse primer rbcL_Rev
source                  1..43
                        mol_type = other DNA
                        organism = synthetic construct
SEQUENCE: 10
catgttagta acagaacctt cttcaaaaag gtctaacggg taa                   43

SEQ ID NO: 11           moltype = DNA  length = 890
FEATURE                 Location/Qualifiers
misc_feature            1..890
                        note = Candidatus Liberibacter asiaticus
source                  1..890
                        mol_type = genomic DNA
                        organism = unidentified
SEQUENCE: 11
atgagtaagg tatctgctgt tgcggtaaag gagttacgtg ggaaaactgg tgcaggtatc  60
ttggactgca agaatgccct tttggaggct aagggtgata gtgaattagc gattgatatt  120
ttgcgcacta aaggagctat ggcagctagt aagagagagg gtagaaaggt ttcagagggg  180
cttataggaa ttgctcgtga tggatataag aaggcatcga ttgtagaagt caatgttgag  240
accgatagtt tggcaaaaaa cactgatttt cagagtcttg tttctaatat tgcgggtatt  300
gctctttcca ccgatggttc tttggacaat gttcttgcga tgccatttga ccatagtggg  360
attactgtgg gggatggaat taagcagcag attgctatca ccggtgaatg tattaagctg  420
aggcgttccg ctcttctgtg tgtttcggaa ggggtcatct cttcgtatct tcatgcttct  480
ccttctgagg gtttaggatc gattggtgtt cttgtagcgt tgcagtcttc tgcggaagat  540
aaggaattgc tttctgcgat tggagagaag attgcagtgc atgtaatgct ggcttctcct  600
tcggtgattt ctgtgcagat gcttgatcct tctattgttg ctaataaacg tgcccattac  660
atgacagaag cacttgattc tgggaaatca ggtaatattg ttgaaaagat cgtaaatgga  720
aagatgcaaa gcttttgtaa ggaatgtgtt cttttgcatc aggggtttgt tgttgatcct  780
tccaaaactg tatcagattt tttgaaagaa tctgaaaaat caatcggtgc ttctattgaa  840
gttgttggtg tatctcattt tgttgtgggt aaagaaaatg atgatggtta            890

SEQ ID NO: 12           moltype = DNA  length = 57
FEATURE                 Location/Qualifiers
misc_feature            1..57
                        note = forward primer NBEU523377-F-57
source                  1..57
                        mol_type = other DNA
                        organism = synthetic construct
SEQUENCE: 12
tcttcgtatc ttcatgcttc tccttctgag ggtttaggat cgattggtgt tcttgta     57

SEQ ID NO: 13           moltype = DNA  length = 57
FEATURE                 Location/Qualifiers
misc_feature            1..57
                        note = biotinylated forward primer EU523377-F-57
source                  1..57
                        mol_type = other DNA
                        organism = synthetic construct
SEQUENCE: 13
tcttcgtatc ttcatgcttc tccttctgag ggtttaggat cgattggtgt tcttgta     57

SEQ ID NO: 14           moltype = DNA  length = 47
FEATURE                 Location/Qualifiers
misc_feature            1..47
                        note = forward primer HLBForSh
source                  1..47
                        mol_type = other DNA
                        organism = synthetic construct
SEQUENCE: 14
cgattggtgt tcttgtagcg ttgcagtctt ctgcggaaga taaggaa               47
```

```
SEQ ID NO: 15              moltype = DNA  length = 56
FEATURE                    Location/Qualifiers
misc_feature               1..56
                           note = reverse primer EU523377-R-56
source                     1..56
                           mol_type = other DNA
                           organism = synthetic construct
SEQUENCE: 15
tgcttctgtc atgtaatggg cacgtttatt agcaacaata aaggatcaa gcatct     56

SEQ ID NO: 16              moltype = DNA  length = 49
FEATURE                    Location/Qualifiers
misc_feature               1..49
                           note = reverse primer HLBRevSh
source                     1..49
                           mol_type = other DNA
                           organism = synthetic construct
SEQUENCE: 16
aacaatagaa ggatcaagca tctgcacaga atcaccgaa ggagaagcc              49

SEQ ID NO: 17              moltype = DNA  length = 39
FEATURE                    Location/Qualifiers
misc_feature               1..39
                           note = Forward Primer (underlined), contains 5' detection
                            sequence HLBas-P2
source                     1..39
                           mol_type = other DNA
                           organism = synthetic construct
SEQUENCE: 17
gatgcaaggt cgcatatgag gagcgcgtat gcaatacga                        39

SEQ ID NO: 18              moltype = DNA  length = 56
FEATURE                    Location/Qualifiers
misc_feature               1..56
                           note = Reverse Primer (underlined), contains 5' T7 promoter
                            HLBr-P1
source                     1..56
                           mol_type = other DNA
                           organism = synthetic construct
SEQUENCE: 18
aattctaata cgactcacta tagggagaag ggcgttatcc cgtagaaaaa ggtaga     56

SEQ ID NO: 19              moltype = DNA  length = 45
FEATURE                    Location/Qualifiers
misc_feature               1..45
                           note = forward primer hyvI_For
source                     1..45
                           mol_type = other DNA
                           organism = synthetic construct
SEQUENCE: 19
ggccgtttta acacaaaaga tgaatatcat agatggggta gtcaa                 45

SEQ ID NO: 20              moltype = DNA  length = 51
FEATURE                    Location/Qualifiers
misc_feature               1..51
                           note = reverse primer hyvI_Rev
source                     1..51
                           mol_type = other DNA
                           organism = synthetic construct
SEQUENCE: 20
cggccatttt agataaatca atttgttcta gttagatac atcaatttgt t           51

SEQ ID NO: 21              moltype = DNA  length = 46
FEATURE                    Location/Qualifiers
misc_feature               1..46
                           note = forward primer
source                     1..46
                           mol_type = other DNA
                           organism = synthetic construct
SEQUENCE: 21
gttcttgtag cgttgcagtc ttctgcggaa gataaggaat tgcttt                46

SEQ ID NO: 22              moltype = DNA  length = 49
FEATURE                    Location/Qualifiers
misc_feature               1..49
                           note = reverse primer
source                     1..49
                           mol_type = other DNA
```

```
                        organism = synthetic construct
SEQUENCE: 22
gggcacgttt attagcaaca atagaaggat caagcatctg cacagaaat          49

SEQ ID NO: 23           moltype = DNA  length = 48
FEATURE                 Location/Qualifiers
misc_feature            1..48
                        note = forward primer
source                  1..48
                        mol_type = other DNA
                        organism = synthetic construct
SEQUENCE: 23
cttgtagcgt tgcagtcttc tgcggaagat aaggaattgc tttctgcg           48

SEQ ID NO: 24           moltype = DNA  length = 51
FEATURE                 Location/Qualifiers
misc_feature            1..51
                        note = reverse primer
source                  1..51
                        mol_type = other DNA
                        organism = synthetic construct
SEQUENCE: 24
cacgtttatt agcaacaata gaaggatcaa gcatctgcac agaaatcacc g        51

SEQ ID NO: 25           moltype = DNA  length = 49
FEATURE                 Location/Qualifiers
misc_feature            1..49
                        note = forward primer
source                  1..49
                        mol_type = other DNA
                        organism = synthetic construct
SEQUENCE: 25
ggtgttcttg tatcgttgca gtcttctgcg gaagataagg aattgcttt          49

SEQ ID NO: 26           moltype = DNA  length = 54
FEATURE                 Location/Qualifiers
misc_feature            1..54
                        note = reverse primer
source                  1..54
                        mol_type = other DNA
                        organism = synthetic construct
SEQUENCE: 26
gtaatgggca cgtttattag caacgataga aggatcaagc aactgcacag aaat    54

SEQ ID NO: 27           moltype = DNA  length = 48
FEATURE                 Location/Qualifiers
misc_feature            1..48
                        note = forward primer
source                  1..48
                        mol_type = other DNA
                        organism = synthetic construct
SEQUENCE: 27
cttgtatcgt tgcagtcttc tgcggaagat aaggaattgc tttctgcg           48

SEQ ID NO: 28           moltype = DNA  length = 53
FEATURE                 Location/Qualifiers
misc_feature            1..53
                        note = reverse primer
source                  1..53
                        mol_type = other DNA
                        organism = synthetic construct
SEQUENCE: 28
ggcacgttta ttagcaacga tagaaggatc aagcatctgc acagaaatca ccg     53
```